United States Patent
Telfort et al.

(10) Patent No.: US 10,828,007 B1
(45) Date of Patent: Nov. 10, 2020

(54) ACOUSTIC SENSOR WITH ATTACHMENT PORTION

(71) Applicant: Masimo Corporation, Irvine, CA (US)

(72) Inventors: Valery G. Telfort, Montreal (CA);
Ehsan Masoumi, Montreal (CA);
Dimitar Dimitrov, Saint-Laurent (CA);
Phi Trang, Montreal (CA)

(73) Assignee: Masimo Corporation, Irvine, CA (US)

( * ) Notice: Subject to any disclaimer, the term of this patent is extended or adjusted under 35 U.S.C. 154(b) by 137 days.

(21) Appl. No.: 14/512,286

(22) Filed: Oct. 10, 2014

Related U.S. Application Data

(60) Provisional application No. 61/889,644, filed on Oct. 11, 2013, provisional application No. 62/027,599, filed on Jul. 22, 2014.

(51) Int. Cl.
*A61B 7/04* (2006.01)
*A61B 7/00* (2006.01)
*A61B 5/00* (2006.01)

(52) U.S. Cl.
CPC .......... *A61B 7/003* (2013.01); *A61B 5/6833* (2013.01); *A61B 7/04* (2013.01)

(58) Field of Classification Search
CPC ....... A61B 5/6833; A61B 5/6832; A61B 7/04; A61B 7/045; A61B 2562/0204; A61B 5/683–6834; A61B 2560/04; A61B 2560/0406; A61B 2560/0412; A61B 2560/0425
See application file for complete search history.

(56) References Cited

U.S. PATENT DOCUMENTS

| | | | |
|---|---|---|---|
| 2,699,465 A * | 1/1955 | Hamilton | A61B 5/024 330/1 R |
| 3,399,467 A | 9/1968 | Ravin | |
| 3,682,161 A | 8/1972 | Alibert | |
| 3,867,925 A * | 2/1975 | Ersek | A61B 7/02 181/131 |

(Continued)

FOREIGN PATENT DOCUMENTS

| | | |
|---|---|---|
| CA | 2490438 | 1/2004 |
| CA | 2262236 | 4/2008 |

(Continued)

OTHER PUBLICATIONS

US 8,740,816 B2, 06/2014, Telfort et al. (withdrawn)

(Continued)

*Primary Examiner* — David J. McCrosky
(74) *Attorney, Agent, or Firm* — Knobbe Martens Olson & Bear LLP

(57) ABSTRACT

According to certain described aspects, an acoustic sensor is employed in a variety of beneficial ways to provide improved physiological monitoring, among other advantages. In various embodiments, the acoustic sensor may include an attachment sub-assembly including a deformable portion that enables improved coupling to a patient. Additionally, the acoustic sensor may include an adhesive layer that, in combination with the deformable portion, enables even, robust, and secure attachment of the sensor to the patient. In various embodiments, an acoustic coupler having a semi-spherical shape is provided to further improve coupling of acoustic signals from the patient to the sensor.

8 Claims, 36 Drawing Sheets

(56) References Cited

U.S. PATENT DOCUMENTS

| | | | |
|---|---|---|---|
| 3,951,230 A | 4/1976 | Littmann | |
| 3,991,304 A | 11/1976 | Hillsman | |
| 4,127,749 A | 11/1978 | Atoji et al. | |
| 4,254,302 A | 3/1981 | Walshe | |
| 4,326,143 A | 4/1982 | Guth et al. | |
| 4,401,125 A * | 8/1983 | Taylor | A61B 7/02 |
| | | | 181/131 |
| 4,413,202 A | 11/1983 | Krempl et al. | |
| 4,537,200 A | 8/1985 | Widrow | |
| 4,576,179 A | 3/1986 | Manus et al. | |
| 4,578,613 A | 3/1986 | Dorogusker et al. | |
| 4,634,917 A | 1/1987 | Dvorksy et al. | |
| 4,653,498 A | 3/1987 | New, Jr. et al. | |
| 4,672,976 A | 6/1987 | Kroll | |
| 4,805,633 A | 2/1989 | Kotani et al. | |
| 4,827,943 A | 5/1989 | Bornn et al. | |
| 4,871,046 A | 10/1989 | Turner | |
| 4,884,809 A | 12/1989 | Rowan | |
| 4,924,876 A | 5/1990 | Cameron | |
| 4,947,853 A * | 8/1990 | Hon | A61B 5/022 |
| | | | 600/459 |
| 4,947,859 A | 8/1990 | Brewer et al. | |
| 4,960,118 A | 10/1990 | Pennock | |
| 4,960,128 A | 10/1990 | Gordon et al. | |
| 4,964,408 A | 10/1990 | Hink et al. | |
| 4,982,738 A | 1/1991 | Griebel | |
| 5,003,605 A | 3/1991 | Phillipps et al. | |
| 5,033,032 A | 7/1991 | Houghtaling | |
| 5,036,857 A | 8/1991 | Semmlow et al. | |
| 5,041,187 A | 8/1991 | Hink et al. | |
| 5,069,213 A | 12/1991 | Polczynski | |
| 5,078,151 A | 1/1992 | Laballery | |
| 5,140,992 A | 8/1992 | Zuckerwar et al. | |
| 5,143,078 A | 9/1992 | Mather et al. | |
| 5,163,438 A | 11/1992 | Gordon et al. | |
| 5,269,314 A | 12/1993 | Kendall et al. | |
| 5,278,627 A | 1/1994 | Aoyagi et al. | |
| 5,319,355 A | 6/1994 | Russek | |
| 5,333,106 A | 7/1994 | Lanpher et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| 5,394,877 A * | 3/1995 | Orr | A61B 5/0408 |
| | | | 600/459 |
| 5,406,952 A | 4/1995 | Barnes et al. | |
| D359,546 S | 6/1995 | Savage et al. | |
| 5,428,193 A * | 6/1995 | Mandiberg | A61B 7/02 |
| | | | 181/131 |
| 5,431,170 A | 7/1995 | Mathews | |
| D361,840 S | 8/1995 | Savage et al. | |
| D362,063 S | 9/1995 | Savage et al. | |
| 5,448,996 A | 9/1995 | Bellin et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,539,831 A | 7/1996 | Harley | |
| 5,561,275 A | 10/1996 | Savage et al. | |
| 5,562,002 A | 10/1996 | Lalin | |
| 5,564,108 A | 10/1996 | Hunsaker et al. | |
| 5,578,799 A | 11/1996 | Callahan et al. | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| 5,730,140 A | 3/1998 | Fitch | |
| D393,830 S | 4/1998 | Tobler et al. | |
| 5,738,106 A | 4/1998 | Yamamori et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,812,678 A | 9/1998 | Scalise et al. | |
| 5,823,950 A | 10/1998 | Diab et al. | |
| 5,825,895 A | 10/1998 | Grasfield et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,912,656 A | 6/1999 | Tham et al. | |
| 5,919,134 A | 7/1999 | Diab | |
| 5,921,941 A * | 7/1999 | Longobardo | A61B 7/02 |
| | | | 600/528 |
| 5,934,925 A | 8/1999 | Tobler et al. | |
| 5,940,182 A | 8/1999 | Lepper, Jr. et al. | |
| 5,977,538 A | 11/1999 | Unger et al. | |
| 5,987,343 A | 11/1999 | Kinast | |
| 5,989,193 A | 11/1999 | Sullivan | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,048,323 A * | 4/2000 | Hon | A61B 5/4356 |
| | | | 600/588 |
| 6,067,462 A | 5/2000 | Diab et al. | |
| 6,081,735 A | 6/2000 | Diab et al. | |
| 6,083,156 A | 7/2000 | Lisiecki | |
| 6,088,607 A | 7/2000 | Diab et al. | |
| 6,106,481 A | 8/2000 | Cohen | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,168,568 B1 | 1/2001 | Gavriely | |
| 6,184,521 B1 | 2/2001 | Coffin, IV et al. | |
| 6,206,830 B1 | 3/2001 | Diab et al. | |
| 6,210,344 B1 | 4/2001 | Perin et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,248,083 B1 | 6/2001 | Smith et al. | |
| 6,253,097 B1 | 6/2001 | Aronow et al. | |
| 6,256,523 B1 | 7/2001 | Diab et al. | |
| 6,261,237 B1 | 7/2001 | Swanson et al. | |
| 6,263,222 B1 | 7/2001 | Diab et al. | |
| 6,271,760 B1 | 8/2001 | Watanabe et al. | |
| 6,275,594 B1 | 8/2001 | Senoo et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,295,365 B1 | 9/2001 | Ota | |
| 6,301,493 B1 | 10/2001 | Marro et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |

(56) References Cited

U.S. PATENT DOCUMENTS

| | | |
|---|---|---|
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,014 B1 | 6/2002 | Toda |
| 6,415,033 B1 | 7/2002 | Halleck et al. |
| 6,423,013 B1 | 7/2002 | Bakker et al. |
| 6,430,437 B1 | 8/2002 | Marro |
| 6,430,525 B1 | 8/2002 | Weber et al. |
| 6,438,238 B1 | 8/2002 | Callahan |
| 6,463,311 B1 | 10/2002 | Diab |
| 6,470,199 B1 | 10/2002 | Kopotic et al. |
| 6,486,588 B2 | 11/2002 | Doron et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,560,470 B1 | 5/2003 | Pologe |
| 6,571,113 B1 | 5/2003 | Fein et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,702,755 B1 | 3/2004 | Stasz et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,074 B1 | 4/2004 | Kästle |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,816,744 B2 | 11/2004 | Garfield et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,937,736 B2 | 8/2005 | Toda |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,954,971 B1 | 10/2005 | Bryant et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,020,508 B2 | 3/2006 | Stivoric et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,035,684 B2 | 4/2006 | Lee |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,110,804 B2 | 9/2006 | Baumer et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,246,069 B1 | 7/2007 | O'Hanlon et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,270,126 B2 | 9/2007 | Wallace et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,148 B2 | 4/2008 | Narimatsu |
| 7,368,855 B2 | 5/2008 | Orten |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |

(56) References Cited

U.S. PATENT DOCUMENTS

| | | |
|---|---|---|
| 7,469,157 B2 | 12/2008 | Diab et al. |
| 7,469,158 B2 | 12/2008 | Cutler et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,515,044 B2 | 4/2009 | Welch et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,625,117 B2 | 12/2009 | Haslett et al. |
| 7,647,083 B2 | 1/2010 | Al-Ali et al. |
| D609,193 S | 2/2010 | Al-Ali et al. |
| 7,662,105 B2 | 2/2010 | Hatlestad |
| 7,668,588 B2 | 2/2010 | Kovacs |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,783,056 B2 | 8/2010 | Wilmink |
| 7,791,155 B2 | 9/2010 | Diab |
| 7,801,581 B2 | 9/2010 | Diab |
| 7,806,226 B2 | 10/2010 | Drummond et al. |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,860,553 B2 | 12/2010 | Govari et al. |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,903,825 B1 | 3/2011 | Melanson |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,940,937 B2 | 5/2011 | Smith |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,976,480 B2 | 7/2011 | Grajales et al. |
| 7,988,637 B2 | 8/2011 | Diab |
| 7,988,688 B2 | 8/2011 | Webb et al. |
| 7,990,382 B2 | 8/2011 | Kiani |
| 7,991,165 B2 | 8/2011 | Kassel et al. |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,092,396 B2 | 1/2012 | Bagha et al. |
| 8,108,039 B2 | 1/2012 | Saliga et al. |
| RE43,169 E | 2/2012 | Parker |
| 8,116,841 B2 | 2/2012 | Bly et al. |
| 8,118,620 B2 | 2/2012 | Al-Ali et al. |
| 8,121,673 B2 | 2/2012 | Tran |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,241,223 B2 | 8/2012 | Gavriely et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,291 B2 | 9/2012 | Bridger et al. |
| 8,265,723 B1 | 9/2012 | McHale et al. |
| 8,274,360 B2 | 9/2012 | Sampath et al. |
| 8,275,140 B2 | 9/2012 | Smith |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| 8,320,576 B1 | 11/2012 | Abbruscato |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani |
| 8,396,228 B2 | 3/2013 | Bilan |
| 8,399,822 B2 | 3/2013 | Al-Ali |
| 8,401,602 B2 | 3/2013 | Kiani |
| 8,403,865 B2 | 3/2013 | Halperin et al. |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |

(56) References Cited

U.S. PATENT DOCUMENTS

| | | |
|---|---|---|
| 8,437,825 B2 | 5/2013 | Dalvi et al. |
| 8,449,469 B2 | 5/2013 | Benet et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,491,489 B2 | 7/2013 | Shin et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,517,981 B2 | 8/2013 | Zornow |
| 8,523,781 B2 | 9/2013 | Al-Ali |
| 8,526,665 B2 | 9/2013 | Lutz et al. |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,595 B2 | 2/2014 | Basinger |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,189 B2 | 4/2014 | Shennib |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiana |
| 8,740,792 B1 | 6/2014 | Kiana et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali et al. |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,961,413 B2 | 2/2015 | Teller et al. |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |

(56) References Cited

U.S. PATENT DOCUMENTS

| | | | |
|---|---|---|---|
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,411,936 B2 | 8/2016 | Landrum et al. |
| 9,436,645 B2 | 9/2016 | Al-Ali et al. |
| 9,439,599 B2 * | 9/2016 | Thompson ............ A61B 5/6833 |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani et al. |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 9,955,937 B2 * | 5/2018 | Telfort .................. A61B 7/026 |
| 10,098,610 B2 | 10/2018 | Al-Ali et al. |
| 10,342,497 B2 | 7/2019 | Al-Ali et al. |
| 10,349,895 B2 | 7/2019 | Telfort et al. |
| 10,357,209 B2 | 7/2019 | Al-Ali |
| 2003/0135087 A1 | 7/2003 | Hickle et al. |
| 2003/0149349 A1 | 8/2003 | Jensen |
| 2003/0196660 A1 | 10/2003 | Haveri |
| 2004/0133087 A1 | 7/2004 | Ali et al. |
| 2004/0215094 A1 | 10/2004 | Baumer et al. |
| 2004/0228494 A1 | 11/2004 | Smith |
| 2005/0033128 A1 | 2/2005 | Ali |
| 2005/0065417 A1 | 3/2005 | Ali |
| 2006/0047215 A1 | 3/2006 | Newman et al. |
| 2006/0059324 A1 | 3/2006 | Simske et al. |
| 2006/0094943 A1 | 5/2006 | Van Slyke |
| 2006/0161054 A1 | 7/2006 | Reuss et al. |
| 2006/0184052 A1 | 8/2006 | Iwasawa |
| 2006/0190051 A1 | 8/2006 | Gerber et al. |
| 2006/0198533 A1 | 9/2006 | Wang |
| 2006/0264767 A1 | 11/2006 | Shennib |
| 2007/0016030 A1 | 1/2007 | Stringer |
| 2007/0049837 A1 | 3/2007 | Shertukde et al. |
| 2007/0056582 A1 | 3/2007 | Wood et al. |
| 2007/0058818 A1 | 3/2007 | Yoshimine |
| 2007/0106179 A1 | 5/2007 | Bagha et al. |
| 2007/0147639 A1 | 6/2007 | Richardson et al. |
| 2007/0165872 A1 | 7/2007 | Bridger et al. |
| 2007/0167855 A1 | 7/2007 | Shin et al. |
| 2007/0173730 A1 | 7/2007 | Bikko |
| 2007/0208262 A1 | 9/2007 | Kovacs |
| 2007/0255153 A1 * | 11/2007 | Kumar ................ A61B 5/6833 |
| | | 600/515 |
| 2007/0282174 A1 | 12/2007 | Sabatino |
| 2007/0282478 A1 | 12/2007 | Al-Ali et al. |
| 2008/0039735 A1 | 2/2008 | Hickerson |
| 2008/0076972 A1 | 3/2008 | Dorogusker et al. |
| 2008/0077026 A1 | 3/2008 | Banet et al. |
| 2008/0077435 A1 | 3/2008 | Muradia |
| 2008/0093157 A1 | 4/2008 | Drummond et al. |

(56) References Cited

U.S. PATENT DOCUMENTS

| | | |
|---|---|---|
| 2008/0097249 A1 | 4/2008 | Pool et al. |
| 2008/0139953 A1 | 6/2008 | Baker et al. |
| 2008/0143496 A1 | 6/2008 | Linjama |
| 2008/0188733 A1 | 8/2008 | Al-Ali et al. |
| 2008/0188760 A1 | 8/2008 | Al-Ali |
| 2008/0219464 A1 | 9/2008 | Smith |
| 2008/0251313 A1 | 10/2008 | Knight et al. |
| 2008/0281219 A1 | 11/2008 | Glickman et al. |
| 2009/0076363 A1 | 3/2009 | Bly et al. |
| 2009/0093687 A1 | 4/2009 | Telfort et al. |
| 2009/0170664 A1 | 7/2009 | Shirasaki et al. |
| 2009/0247924 A1 | 10/2009 | Lamego et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0299157 A1 | 12/2009 | Telfort et al. |
| 2009/0299742 A1 | 12/2009 | Toman et al. |
| 2009/0316925 A1 | 12/2009 | Eisenfeld et al. |
| 2010/0004518 A1 | 1/2010 | Vo et al. |
| 2010/0030040 A1 | 2/2010 | Poeze et al. |
| 2010/0069725 A1 | 3/2010 | Al-Ali |
| 2010/0090901 A1 | 4/2010 | Smith et al. |
| 2010/0094096 A1 | 4/2010 | Petruzzelli et al. |
| 2010/0204996 A1 | 8/2010 | Zeng et al. |
| 2010/0261979 A1 | 10/2010 | Kiani |
| 2010/0274099 A1* | 10/2010 | Telfort ............ A61B 5/6843 600/300 |
| 2010/0305416 A1* | 12/2010 | Bedard ............ A61B 5/6833 600/309 |
| 2010/0317936 A1 | 12/2010 | Al-Ali et al. |
| 2011/0001605 A1 | 1/2011 | Kiani et al. |
| 2011/0028802 A1 | 2/2011 | Addison |
| 2011/0034831 A1 | 2/2011 | Christensen et al. |
| 2011/0082711 A1 | 4/2011 | Poeze et al. |
| 2011/0087083 A1 | 4/2011 | Poeze et al. |
| 2011/0105854 A1 | 5/2011 | Kiani et al. |
| 2011/0125060 A1 | 5/2011 | Telfort et al. |
| 2011/0172561 A1 | 7/2011 | Kiani et al. |
| 2011/0172967 A1 | 7/2011 | Al-Ali et al. |
| 2011/0196211 A1 | 8/2011 | Al-Ali |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0213273 A1 | 9/2011 | Telfort et al. |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0279963 A1* | 11/2011 | Kumar ............ A61B 5/6833 361/679.31 |
| 2011/0288383 A1 | 11/2011 | Diab |
| 2011/0288431 A1 | 11/2011 | Alshaer et al. |
| 2011/0301444 A1 | 12/2011 | Al-Ali |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0116175 A1 | 5/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0230523 A1 | 9/2012 | Ehrlund |
| 2012/0232427 A1 | 9/2012 | Bakema et al. |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0302894 A1 | 11/2012 | Diab et al. |
| 2012/0302920 A1 | 11/2012 | Bridger et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0338461 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0090567 A1 | 4/2013 | Al-Ali et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |

(56) References Cited

U.S. PATENT DOCUMENTS

| | | |
|---|---|---|
| 2014/0303520 A1 | 10/2014 | Telfort et al. |
| 2014/0309506 A1 | 10/2014 | Lamego et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiana |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2014/0371548 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0099998 A1* | 4/2015 | Christensen ......... A61B 5/6833 600/586 |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0103874 A1 | 4/2018 | Lee et al. |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |

(56) References Cited

U.S. PATENT DOCUMENTS

| | | |
|---|---|---|
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0153446 A1 | 6/2018 | Kiani |
| 2018/0206815 A1 | 7/2018 | Telfort |
| 2018/0289337 A1 | 10/2018 | Al-Ali et al. |
| 2019/0142344 A1 | 5/2019 | Telfort et al. |

FOREIGN PATENT DOCUMENTS

| | | | |
|---|---|---|---|
| EP | 0716628 | | 12/1998 |
| EP | 0659058 | | 1/1999 |
| EP | 0956820 | A1 | 11/1999 |
| EP | 1518442 | | 3/2005 |
| EP | 2 014 234 | | 1/2009 |
| EP | 1207536 | | 2/2010 |
| EP | 2391273 | | 12/2011 |
| EP | 2488106 | | 8/2012 |
| EP | 2488978 | | 8/2012 |
| EP | 2710959 | | 3/2014 |
| EP | 2765909 | | 8/2014 |
| FR | 2 847 796 | | 6/2004 |
| GB | 2358546 | | 7/2001 |
| JP | 60059900 | | 4/1985 |
| JP | 01-309872 | | 12/1989 |
| JP | H04-317637 | A | 11/1992 |
| JP | H07-152553 | A | 6/1995 |
| JP | 10-155755 | | 6/1998 |
| JP | 2001-50713 | | 2/2001 |
| JP | 2003-329719 | | 11/2003 |
| JP | 2005-522292 | A | 7/2005 |
| JP | 2005-531230 | A | 10/2005 |
| JP | 2012-513872 | | 6/2012 |
| JP | 2013-508029 | | 3/2013 |
| JP | 2013-508030 | | 3/2013 |
| WO | WO 1994/005207 | | 3/1994 |
| WO | WO 1994/013207 | | 6/1994 |
| WO | WO 1995/029632 | | 11/1995 |
| WO | WO 1999/053277 | | 10/1999 |
| WO | WO 2000/010462 | | 3/2000 |
| WO | WO 2001/034033 | | 5/2001 |
| WO | WO 2001/87005 | | 11/2001 |
| WO | WO 2001/097691 | | 12/2001 |
| WO | WO 2002/003042 | | 1/2002 |
| WO | WO 2001/078059 | | 3/2002 |
| WO | WO 2002/024067 | | 7/2002 |
| WO | WO 2003/058646 | | 7/2003 |
| WO | WO 2003/087737 | | 10/2003 |
| WO | WO 2004/000111 | | 12/2003 |
| WO | WO 2004/004411 | | 1/2004 |
| WO | WO 2004078038 | A1 * | 9/2004 ........... A61B 5/0408 |
| WO | WO 2005/096931 | | 10/2005 |
| WO | WO 2005/099562 | | 10/2005 |
| WO | WO 2008/017246 | | 2/2008 |
| WO | WO 2008/148172 | | 12/2008 |
| WO | WO 2009/137524 | | 11/2009 |
| WO | WO 2009/155593 | | 12/2009 |
| WO | WO 2010/078168 | | 7/2010 |
| WO | WO 2011/047211 | | 4/2011 |
| WO | WO 2011/047213 | | 4/2011 |
| WO | WO 2011/047216 | | 8/2011 |
| WO | WO 2011/047207 | | 9/2011 |
| WO | WO 2011/047209 | | 3/2012 |
| WO | WO 2013/056141 | | 4/2013 |

OTHER PUBLICATIONS

US 8,845,543 B2, 09/2014, Diab et al. (withdrawn)
U.S. Appl. No. 12/905,384, filed Oct. 2010, Al-Ali et al.
U.S. Appl. No. 12/905,449, filed Oct. 2010, Al-Ali et al.
U.S. Appl. No. 12/905,489, filed Oct. 2010, Weber et al.
U.S. Appl. No. 13/152,259, filed Jun. 2011, Kiani.
U.S. Appl. No. 13/554,908, filed Jul. 2012, Telfort et al.
Analog Devices, 12-Bit Serial Input Multiplying D/A Converter, Product Data Sheet, 2000.
Avago Technologies, "HCNR200 and HCNR201, High-Linearity Analog Optocouplers," Data Sheet, Avago Technologies, Nov. 18, 2008.
Eldor et al., "A device for monitoring ventilation during anesthesia; the paratracheal audible respiratory monitor", Canadian Journal of Anesthesia, 1990, vol. 9, No. 1, p. 95-98.
EP Office Action dated Mar. 5, 2013 in application No. 10779086.7.
EP Office Action dated May 18, 2011 in application No. 03711767.8.
European Search Report for Application No. 13185148.7 dated Dec. 6, 2013.
Images showing tear down of a Measurement Specialties' stethoscope, Images taken on Sep. 7, 2007, in 38 pages.
International Preliminary Report on Patentability (IPRP) in PCT/US2010/052754, dated Apr. 26, 2012.
International Preliminary Report on Patentability dated Apr. 15, 2014 for PCT Application No. PCT/US2012/060084.
International Preliminary Report on Patentability in PCT/US2010/052763 dated Apr. 17, 2012 in 9 pages.
International Search Report & Written Opinion for PCT/US2010/052756, dated Feb. 6, 2012; 17 pages.
International Search Report & Written Opinion, PCT Application PCT/US2010/052758, dated Feb. 10, 2011; 12 pages.
International Search Report & Written Opinion, PCT Application PCT/US2010/058981, dated Feb. 17, 2011; 11 pages.
International Search Report and Written Opinion for PCT/US2009/042902, dated Dec. 8, 2009.
International Search Report and Written Opinion in PCT/US2010/052754 dated Jul. 27, 2011.
International Search Report and Written Opinion in PCT/US2010/052763, dated May 13, 2011.
International Search Report and Written Opinion in PCT/US2010052760 dated Mar. 8, 2011 in 11 pages.
International Search Report and Written Opinion issued in PCT Application No. PCT/US2009/069287, dated Jun. 30, 2010.
International Search Report, PCT Application PCT/CA2003/000536, dated Dec. 11, 2003; 2 pages.
Office Action in Japanese Application No. 2011-544508 dated Apr. 30, 2014.
PCT Invitation to Pay Fees and Initial Search Report in PCT/US2009/069287, dated Apr. 21, 2010.
PCT Invitation to Pay Fees and Initial Search Report in PCT/US2010/052754, dated Mar. 15, 2011.
PCT Invitation to Pay Fees and Initial Search Report in PCT/US2010/052756, dated Oct. 5, 2011.
Sierra et al., Monitoring Respiratory Rate Based on Tracheal Sounds. First Experiences, Proceedings of the 26th Annual Int'l Conf. of the IEEE EMBS (Sep. 2004), 317-320.
WelchAllyn OEM Technologies, ECG ASIC, ECG 3-lead, 5-lead, 12-lead and RESP Signal Processing, ECG ASIC Part No. 000.91163 (2001).
White, "Advanced Compression Techniques, Tips & Tricks", Part 1 and Part 2, Dec. 2000 and Jan. 2001 in 7 pages.
International Search Report and Written Opinion in PCT/US2009/042902 dated Dec. 8, 2009 in 19 pages.
International Search Report and Written Opinion in PCT/US2010/052756 dated Feb. 6, 2012 in 16 pages.
International Search Report and Written Opinion in PCTUS2010/052760 dated Mar. 8, 2011 in 10 pages.
EP Office Action dated Jul. 11, 2016 for application No. 10779086.7.
White, "Advanced Compression Techniques, Tips & Tricks", Part 1 and Part 2, Dec. 2000 and Jan. 2001 in 11 pages.
International Search Report and Written Opinion in PCT/US2009/042902 dated Aug. 12, 2009 in 19 pages.
International Search Report and Written Opinion in PCT/US2010/052756 dated Feb. 6, 2012 in 15 pages.
International Search Report and Written Opinion in PCTUS2010/052760 dated Mar. 8, 2011 in 9 pages.
Office Action for European Patent Application No. 13185148.7 dated Apr. 4, 2017.

(56) References Cited

OTHER PUBLICATIONS

Oversampling by Wikipedia, the free encyclopedia, pub. Online Oct. 7, 2012 at "https://wikipedia.org/w/index.php?title=Oversampling&oldid=516454012", accessed Sep. 3, 2015.

Pseudorandom noise by Wikipedia, the free encyclopedia, pub. Online Jul. 25, 2012 at "https://wikipedia.org/w/index.php?title=Pseudorandom_noise&oldid=504121479", accessed Sep. 3, 2015.

Noise generator by Wikipedia, the free encyclopedia, pub. Online May 6, 2012 at "https://wikipedia.org/w/index.php?title=Noise_generator&oldid=490897729", accessed Sep. 3, 2015.

Office Action for EP Application No. 10779086.7 dated May 12, 2017.

Office Action for EP Application No. 13185148.7 dated Nov. 7, 2017.

EP Office Action dated Oct. 16, 2018 in application No. 10773191.1.

EP Office Action dated Dec. 10, 2018 in application No. 10779086.7.

Office Action in European Application No. 12784142.7 dated Apr. 10, 2018 in 5 pages.

Office Action for Application No. 13185148.7 dated Jun. 7, 2018.

Office Action for Application No. 13185148.7 dated Apr. 4, 2019.

\* cited by examiner

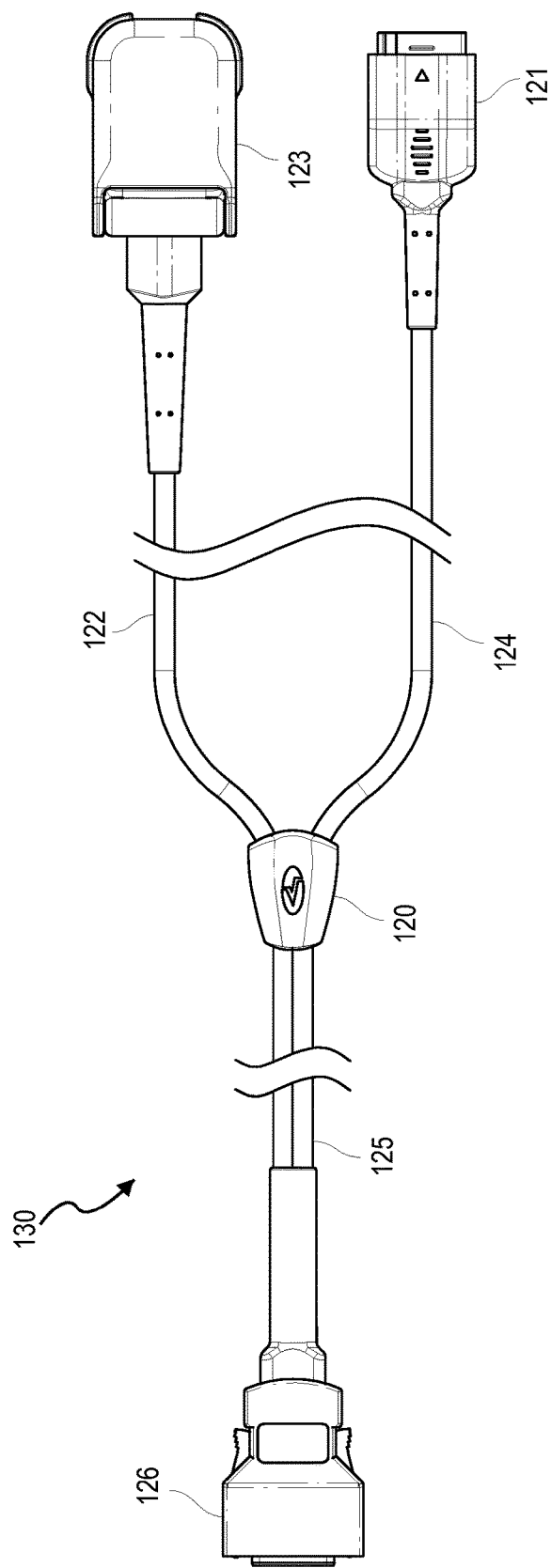
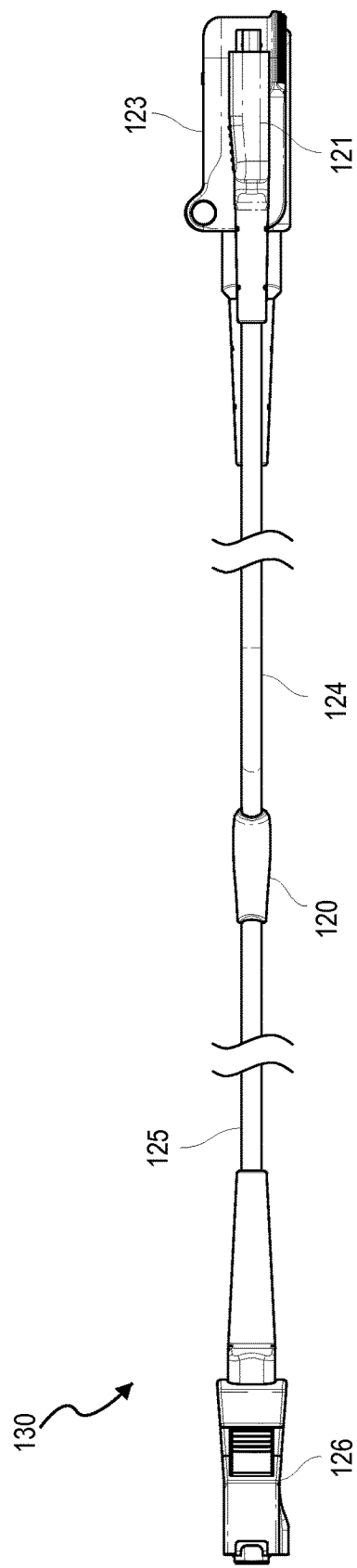
FIG. 1D
FIG. 1E

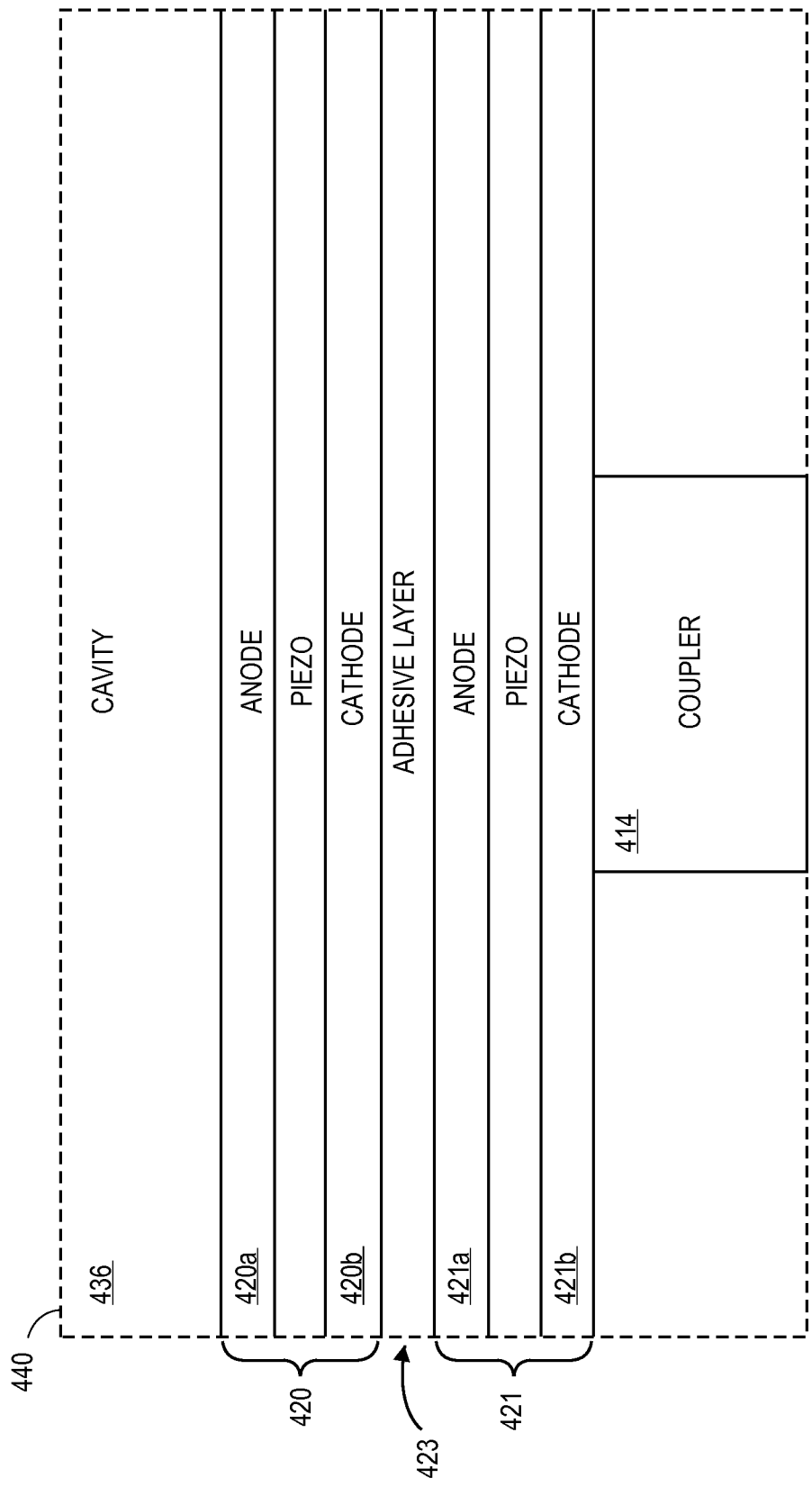

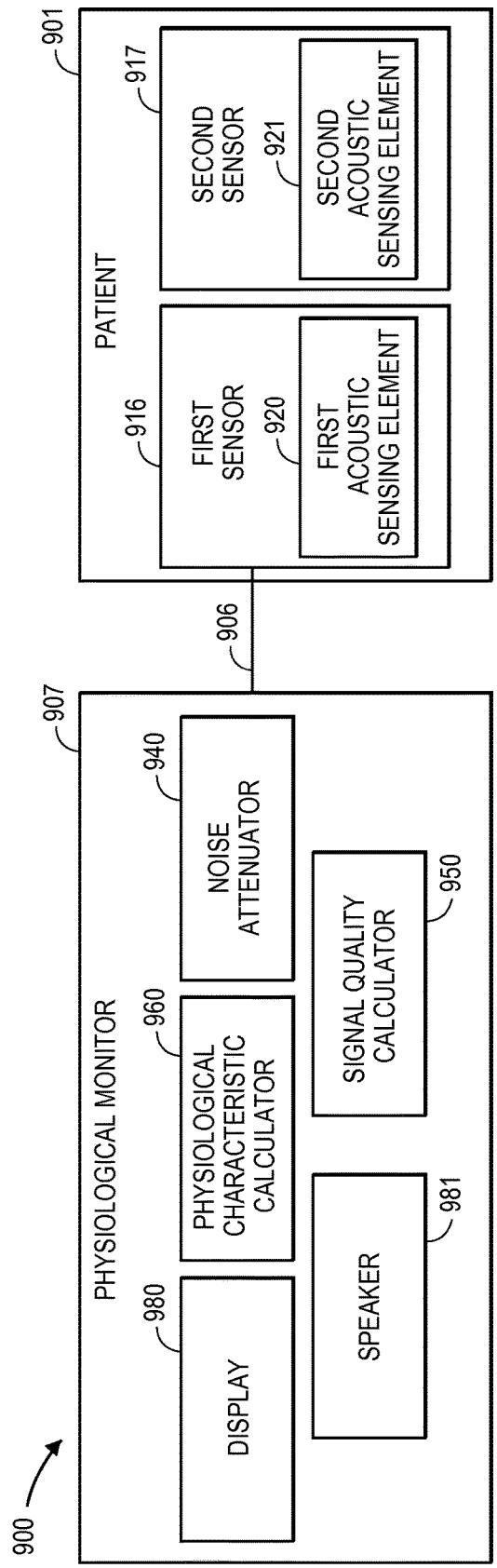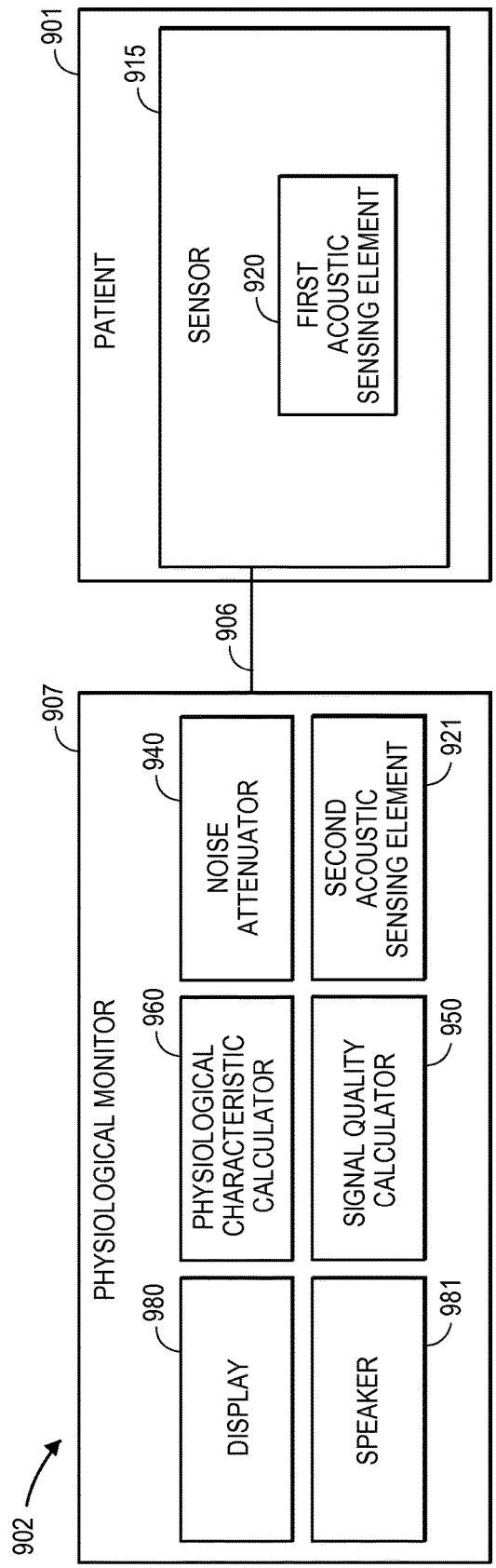

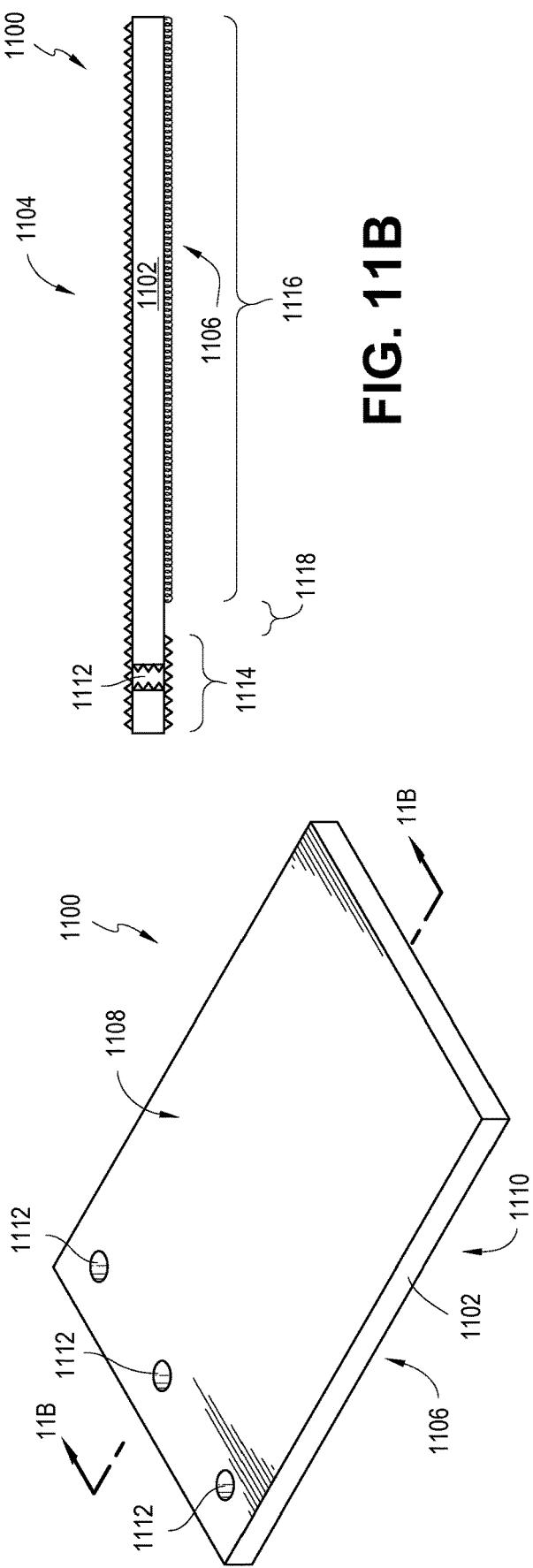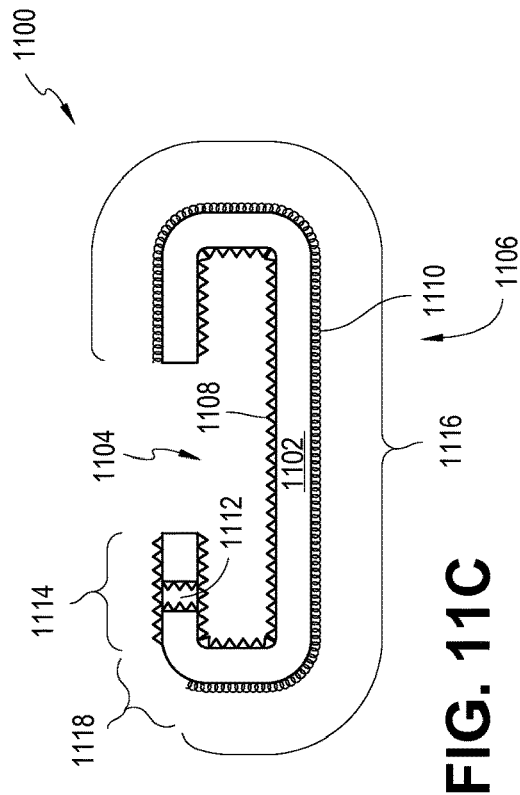
FIG. 11A
FIG. 11B
FIG. 11C

ACOUSTIC SENSOR WITH ATTACHMENT PORTION

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

This application claims benefit of U.S. Provisional Patent Application No. 61/889,644, filed Oct. 11, 2013, titled "ACOUSTIC SENSOR WITH ATTACHMENT PORTION," and also claims benefit of U.S. Provisional Patent Application No. 62/027,599, filed Jul. 22, 2014, titled "ACOUSTIC SENSOR WITH ATTACHMENT PORTION." The entire disclosure of each of the above items is hereby made part of this specification as if set forth fully herein and incorporated by reference for all purposes, for all that it contains.

This application also relates to the following U.S. patent applications:

| App. No. | Filing Date | Title | Attorney Docket |
| --- | --- | --- | --- |
| 12/044,883 | Mar. 8, 2008 | SYSTEMS AND METHODS FOR DETERMINING A PHYSIOLOGICAL CONDITION USING AN ACOUSTIC MONITOR | MCAN.014A |
| 12/904,836 | Oct. 14, 2010 | BIDIRECTIONAL PHYSIOLOGICAL INFORMATION DISPLAY | MCAN.019A1 |
| 12/904,823 | Oct. 14, 2010 | BIDIRECTIONAL PHYSIOLOGICAL INFORMATION DISPLAY | MCAN.019A2 |
| 12/643,939 | Dec. 21, 2009 | ACOUSTIC SENSOR ASSEMBLY | MCAN.030A |
| 12/904,931 | Oct. 14, 2010 | ACOUSTIC RESPIRATORY MONITORING SENSOR HAVING MULTIPLE SENSING ELEMENTS | MCAN.033A |
| 12/904,890 | Oct. 14, 2010 | ACOUSTIC RESPIRATORY MONITORING SENSOR HAVING MULTIPLE SENSING ELEMENTS | MCAN.033A2 |
| 12/904,938 | Oct. 14, 2010 | ACOUSTIC RESPIRATORY MONITORING SENSOR HAVING MULTIPLE SENSING ELEMENTS | MCAN.033A3 |
| 12/904,907 | Oct. 14, 2010 | ACOUSTIC PATIENT SENSOR | MCAN.033A4 |
| 12/904,789 | Oct. 14, 2010 | ACOUSTIC RESPIRATORY MONITORING SYSTEMS AND METHODS | MCAN.034A |
| 12/904,775 | Oct. 14, 2010 | PULSE OXIMETRY SYSTEM WITH LOW NOISE CABLE HUB | MCAN.035A |
| 12/905,036 | Oct. 14, 2010 | PHYSIOLOGICAL ACOUSTIC MONITORING SYSTEM | MCAN.046A |
| 61/547,007 | Oct. 13, 2011 | PHYSIOLOGICAL ACOUSTIC MONITORING SYSTEM | MCAN.046P1 |
| 13/099,263 | May 2, 2011 | REFLECTIVE NON-INVASIVE SENSOR | MASIMO.800A |
| 14/030,268 | Sep. 18, 2013 | ACOUSTIC PATIENT SENSOR COUPLER | MCAN.054A |

The entire disclosure of each of the above items is hereby made part of this specification as if set forth fully herein and incorporated by reference for all purposes, for all that it contains. Many of the embodiments described herein are compatible with embodiments described in the above related applications. Moreover, some or all of the features described herein can be used or otherwise combined with many of the features described in the applications listed above.

BACKGROUND

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

Due in large part to the above attributes, piezoelectric membranes are particularly suited for the capture of acoustic waves and the conversion thereof into electric signals and, accordingly, have found application in the detection of body sounds. However, there is still a need for a reliable acoustic sensor, particularly one suited for measuring bodily sounds in noisy environments.

SUMMARY

Embodiments of an acoustic sensor and physiological monitoring system described herein are configured to provide accurate and robust measurement of bodily sounds under a variety of conditions, such as in noisy environments or in situations in which stress, strain, or movement can be imparted onto the sensor with respect to a patient.

According to certain described aspects, an acoustic sensor is employed in a variety of beneficial ways to provide improved physiological monitoring, among other advantages. In various embodiments, the acoustic sensor may include an attachment sub-assembly including a deformable portion that enables improved coupling to a patient. Additionally, the acoustic sensor may include an adhesive layer that, in combination with the deformable portion, enables even, robust attachment of the sensor to the patient. In an embodiment, the adhesive layer is coupled to the deformable portion at a middle portion of the adhesive layer such that the adhesive layer may securely attach the sensor to the patient. In various embodiments, an acoustic coupler having a semi-spherical shape is provided to further improve coupling of acoustic signals from the patient to the sensor.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIG. 1D is a top view illustrating an embodiment of a multi-sensor cable.

FIG. 1E is a side view of the multi-sensor cable of FIG. 1D.

FIG. 4B shows a cross-sectional schematic drawing of a portion of the first and second stacked sensing elements of FIG. 4A.

FIG. 9A is a block diagram of an embodiment of an acoustic physiological monitoring system with first and second acoustic sensing elements disposed in separate acoustic sensors.

FIG. 9B is a block diagram of an embodiment of an acoustic physiological monitoring system with an acoustic sensor that includes a first acoustic sensing element, and a physiological monitor unit that includes a second acoustic sensing element.

FIG. 11A a perspective view of a sensing element according to an embodiment of the disclosure usable with sensor embodiments of the present disclosure.

FIG. 11B is a cross-sectional view of the sensing element of FIG. 11A along the line 11B-11B.

FIG. 11C is a cross-sectional view of the sensing element of FIGS. 11A-11B shown in a wrapped configuration.

DETAILED DESCRIPTION

Various embodiments will be described hereinafter with reference to the accompanying drawings. These embodiments are illustrated and described by example only, and are not intended to be limiting.

Overview

In various embodiments, an acoustic sensor configured to operate with a physiological monitoring system includes an acoustic signal processing system that measures and/or determines any of a variety of physiological parameters of a medical patient. For example, in an embodiment, the physiological monitoring system includes an acoustic monitor. The acoustic monitor may be an acoustic respiratory monitor which can determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases the acoustic signal processing system monitors other physiological sounds, such as heart rate to help with probe off detection, heart sounds (S1, S2, S3, S4, and murmurs), and change in heart sounds such as normal to murmur or split heart sounds indicating fluid overload. Moreover, the acoustic signal processing system may (1) use a second probe over the chest for additional heart sound detection; (2) keep the user inputs to a minimum (example, height); and/or (3) use a Health Level 7 (HL7) interface to automatically input patient demography.

In certain embodiments, the physiological monitoring system includes an electrocardiograph (ECG or EKG) that measures and/or determines electrical signals generated by the cardiac system of a patient. The ECG includes one or more sensors for measuring the electrical signals. In some embodiments, the electrical signals are obtained using the same sensors used to obtain acoustic signals.

In still other embodiments, the physiological monitoring system includes one or more additional sensors used to determine other desired physiological parameters. For example, in some embodiments, a photoplethysmograph sensor determines the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In other embodiments, a capnograph determines the carbon dioxide content in inspired and expired air from a patient. In other embodiments, other sensors determine blood pressure, pressure sensors, flow rate, air flow, and fluid flow (first derivative of pressure). Other sensors may include a pneumotachometer for measuring air flow and a respiratory effort belt. In certain embodiments, these sensors are combined in a single processing system which processes signal output from the sensors on a single multi-function circuit board.

Figure 1A:
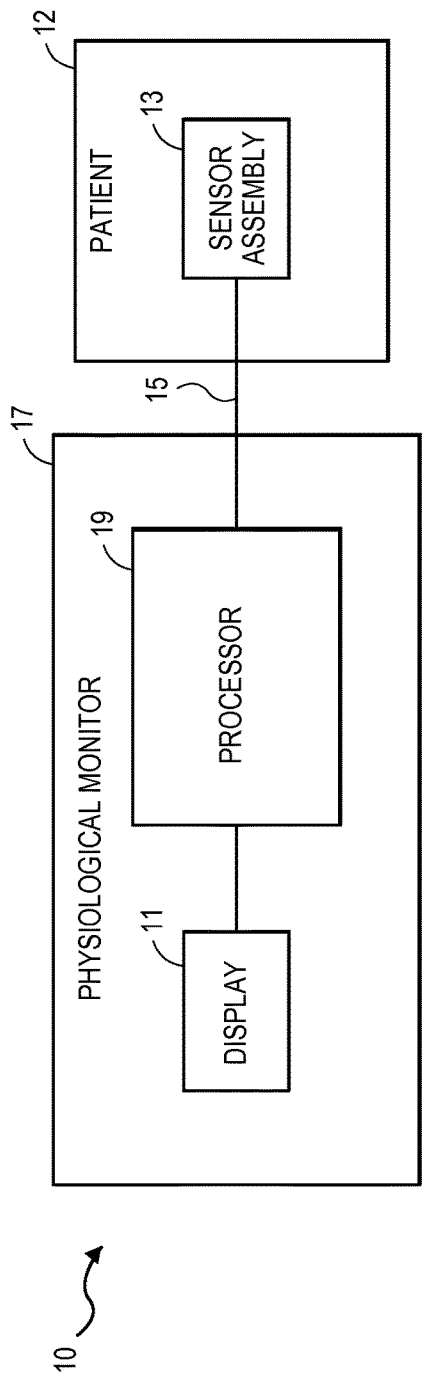
FIGS. 1A-B are block diagrams illustrating physiological monitoring systems in accordance with embodiments of the disclosure.
Figure 1B:
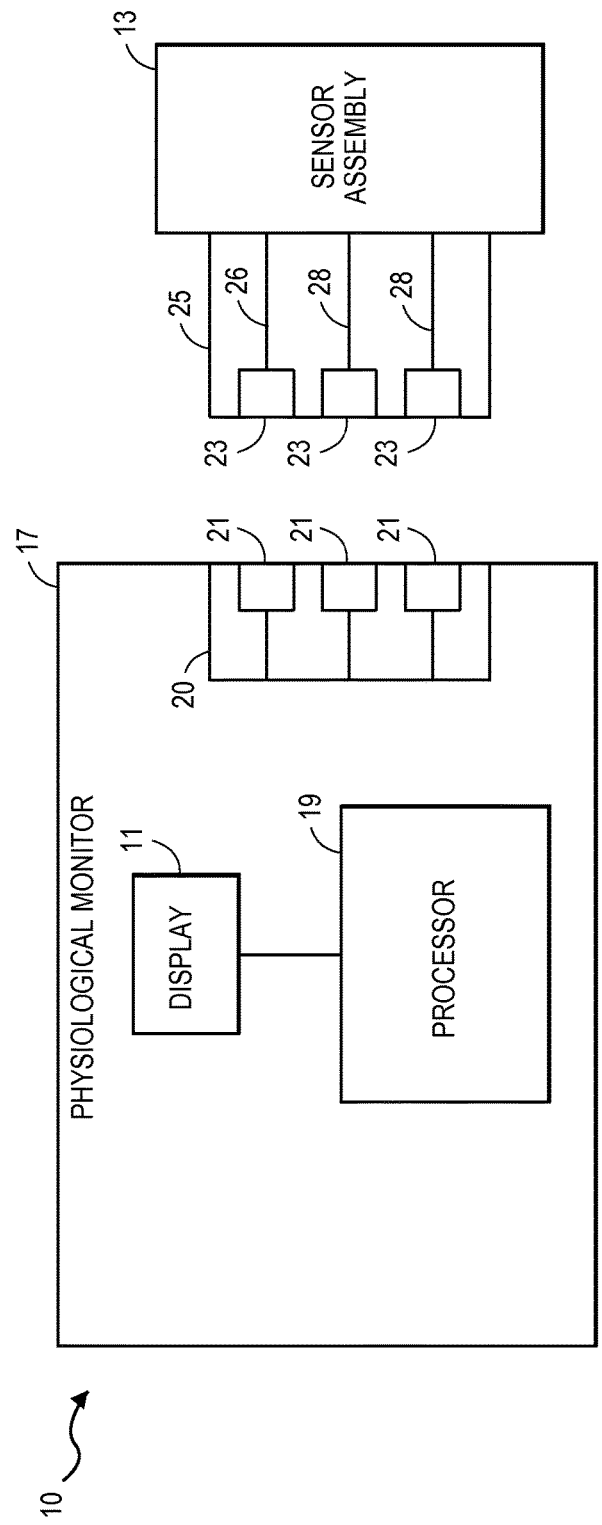
Figure 1C:
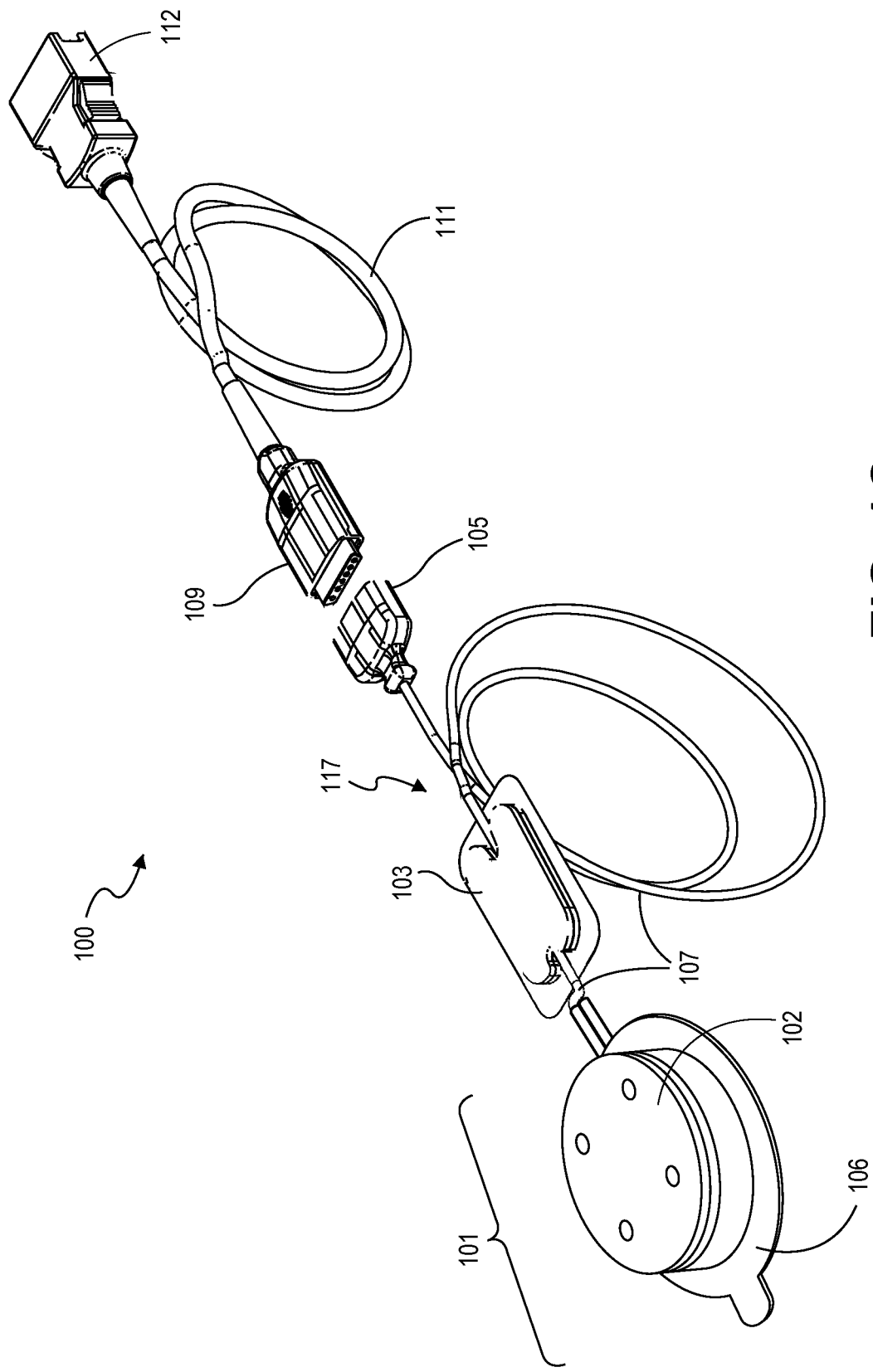
FIG. 1C is a top perspective view illustrating portions of a sensor system in accordance with an embodiment of the disclosure.

Referring to the drawings, FIGS. 1A through 1C illustrate example patient monitoring systems, sensors, and cables that can be used to provide acoustic physiological monitoring of a patient, such as respiratory monitoring. FIGS. 2A-11C illustrate embodiments of sensors, components, and systems, such as those incorporating attachment assemblies, acoustic couplers having spherical caps, and/or multiple acoustic sensing elements that provide certain beneficial results, including improved and/or efficient patient coupling, enhanced signal-to-noise ratio (SNR), electrical shielding and noise compensation, for example. Embodiments of FIGS. 2A-11C can be implemented at least in part using the systems and sensors described in FIGS. 1A through 10.

Turning to FIG. 1A, an embodiment of a physiological monitoring system 10 is shown. In the physiological monitoring system 10, a medical patient 12 is monitored using one or more sensor 13, each of which transmits a signal over a cable 15 or other communication link or medium to a physiological monitor 17. The physiological monitor 17 includes a processor 19 and, optionally, a display 11. The one or more sensors 13 include sensing elements such as, for example, acoustic piezoelectric devices, electrical ECG leads, pulse oximetry sensors, or the like. The sensors 13 can generate respective signals by measuring a physiological parameter of the patient 12. The signals are then processed by one or more processors 19. The one or more processors 19 then communicate the processed signal to the display 11. In an embodiment, the display 11 is incorporated in the physiological monitor 17. In another embodiment, the display 11 is separate from the physiological monitor 17. In one embodiment, the monitoring system 10 is a portable monitoring system. In another embodiment, the monitoring system 10 is a pod, without a display, that is adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include at least two acoustic sensors. In still another embodiment, the one or more sensors 13 include at least two acoustic sensors and one or more ECG sensors, pulse oximetry sensors, bioimpedance sensors, capnography sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13.

As shown in FIG. 1B, the acoustic sensor 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors 103, one or more additional cables 115 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly.

FIG. 1C illustrates an embodiment of a sensor system 100 including a sensor 101 suitable for use with any of the physiological monitors shown in FIGS. 1A and 1B. The sensor system 100 includes a sensor 101, a sensor cable 117, a patient anchor 103 attached to the sensor cable 117 (including cable sections 107), and a connector 105 attached to the sensor cable 117. The sensor 101 includes a housing or attachment sub-assembly 102 configured to house certain componentry of the sensor 101 and an adhesive portion 106 configured to attach the sensor 101 to the patient. The sensor 101 can be removably attached to an instrument cable as described below with respect to FIGS. 1D through 1E. The sensor 101 can be removably attached to an instrument cable 111 via an instrument cable connector 109. The instrument cable 111 can be attached to a physiological monitor (not shown) via connector 112.

The component or group of components between the sensor 101 and the monitor in any particular embodiment may be referred to generally as a cabling apparatus. For example, where one or more of the following components are included, such components or combinations thereof may be referred to as a coupling apparatus: the sensor cable 117, the connector 105, the cable connector 109, the instrument cable 111, and/or the connector 112. It should be noted that one or more of these components may not be included, and that one or more other components may be included between the sensor 101 and the monitor, forming the cabling apparatus.

The acoustic sensor 101 can further include circuitry for detecting and transmitting information related to biological sounds to the physiological monitor. These biological sounds can include heart, breathing, and/or digestive system sounds, in addition to many other physiological phenomena. The acoustic sensor 101 in certain embodiments is a biological sound sensor, such as the sensors described herein. In some embodiments, the biological sound sensor is one of the sensors such as those described in U.S. patent application Ser. No. 12/044,883, filed Mar. 7, 2008, which is incorporated in its entirety by reference herein (the '883 Application). In other embodiments, the acoustic sensor 101 is a biological sound sensor such as those described in U.S. Pat. No. 6,661,161 or U.S. patent application Ser. No. 12/643,939, filed on Dec. 21, 2009 (the '939 Application), both of which are incorporated by reference herein in their entirety. Other embodiments include other suitable acoustic sensors. For example, in certain embodiments, compatible acoustic sensors can be configured to provide a variety of auscultation functions, including live and/or recorded audio output (e.g., continuous audio output) for listening to patient bodily or speech sounds. Examples of such sensors and sensors capable of providing other compatible functionality can be found in U.S. patent application Ser. No. 12/904,789, entitled ACOUSTIC RESPIRATORY MONITORING SYSTEMS AND METHODS, filed on Oct. 14, 2010, which is incorporated by reference herein in its entirety.

In an embodiment, the acoustic sensor 101 includes one or more sensing elements (not shown), such as, for example, a piezoelectric device or other acoustic sensing device. Where a piezoelectric membrane is used, a thin layer of conductive metal can be deposited on each side of the film as electrode coatings, forming electrical poles. The opposing surfaces or poles may be referred to as an anode and cathode, respectively. Each sensing element can generate a voltage potential across the electrical poles that is responsive to vibrations generated by the patient.

The housing or attachment sub-assembly 102 according to certain embodiments houses and/or is coupled to a frame (not shown) or other support structure configured to support various components of the sensor 101. In an embodiment, the one or more sensing elements can be wrapped in tension around the frame. For example, the sensing elements can be positioned across an acoustic cavity disposed on the bottom surface of the frame. Thus, the sensing elements according to some embodiments are free to respond to acoustic waves incident upon them, resulting in corresponding induced voltages across the poles of the sensing elements. In another embodiment, the one or more sensing elements can generally be flat and held in tension across an acoustic cavity disposed on the bottom surface of the frame while the ends of the one or more sensing elements are sandwiched between components of the sensor 101 and the frame.

Additionally, the sensor 101 can include an acoustic coupler (not shown), which can advantageously improve the coupling between the source of the signal to be measured by the sensor (e.g., the patient's body) and the sensing element. The acoustic coupler of one embodiment includes a bump positioned to apply pressure to the sensing element so as to bias the sensing element in tension. For example, the bump can be positioned against the portion of the sensing element that is stretched across the cavity of the frame. In certain embodiments, the coupler can also advantageously provide electrical decoupling or insulation between the electrical components of the sensor and the skin of the patient. In an embodiment, the portion of the acoustic coupler that comes in contact with the patient comprises a spherical cap that may extend across a substantial portion, or substantially all, of a side of the frame and/or the sensor 101.

The adhesive portion 106 of the sensor 101 can include, for example, a layer or portion of patient adhesive (e.g., in some embodiments, tape, glue, a suction device, etc.). The adhesive portion 106 can be used to secure the sensor 101 to a patient's skin. The adhesive portion 106 and the attachment sub-assembly 102 can couple the frame, sensing element, and the coupler, to the patient and can beneficially bias the sensor 101 in tension against the patient's skin and/or reduce stress on the connection between the patient adhesive and the skin.

While an example sensor system 100 has been provided, embodiments described herein are compatible with a variety of sensors and associated components. For example, compatible acoustic couplers, support frames, attachment subassemblies, sensing elements, and other components are described in greater detail below and in the '939 Application.

FIGS. 1D and 1E depict an example dual sensor cable 130 that can be connected to the sensor 101 via the cable 111 as well as to another sensor. The dual sensor cable 130 can replace the single instrument cable 111 of FIG. 1C. The dual sensor cable 130 includes a connector 121 that can couple with the connector 105 of the sensor 101. Likewise, the dual sensor cable 130 includes a connector 123 that can connect to another sensor, such as a pulse oximetry sensor, other optical sensor, ECG sensor, or the like. In another embodiment, the dual sensor cable 130 connects to a second acoustic sensor.

The connector 121 is coupled with a cable section 124, and the connector 123 is also coupled with a cable section 122. These cable sections 122, 124 combine together in a junction 120 to form a single dual cable section 125 that terminates in a monitor connector 126. The junction 120 can be a piece of molded plastic or the like that joins the two cable sections 122, 124 together without electrically coupling the two cables. The monitor connector 126 can connect to a physiological monitor, enabling both sensors connected to the dual sensor cable 130 to provide physiological parameter data to the physiological monitor.

Advantageously, in certain embodiments, the dual sensor cable 130 is smaller than existing dual sensor cables that have extensive electrical decoupling or isolation circuitry inside. Isolation or decoupling circuitry can be included in dual sensor or multiple sensor patient cables to reduce or prevent ground loops from forming in a patient and thereby reduce or prevent electric shock to a patient, as described in U.S. application Ser. No. 12/904,775, filed Oct. 14, 2010, titled "Pulse Oximetry System with Low Noise Cable Hub," the disclosure of which is hereby incorporated by reference in its entirety. However, such circuitry is not included in the dual sensor cable 130 because decoupling can advantageously be performed by the sensor itself, as will be set forth more fully herein. As a result, the dual sensor cable 130 can be less bulky than the cable described in the '775 application while still providing the benefits of multiple sensor monitoring. In other embodiments, the dual sensor cable 130 can also be adapted to interface with more than two sensors, such as any of the sensors described herein.

Examples of Improving Signal-to-Noise Ratio Using Multiple Sensors

Figure 2A:
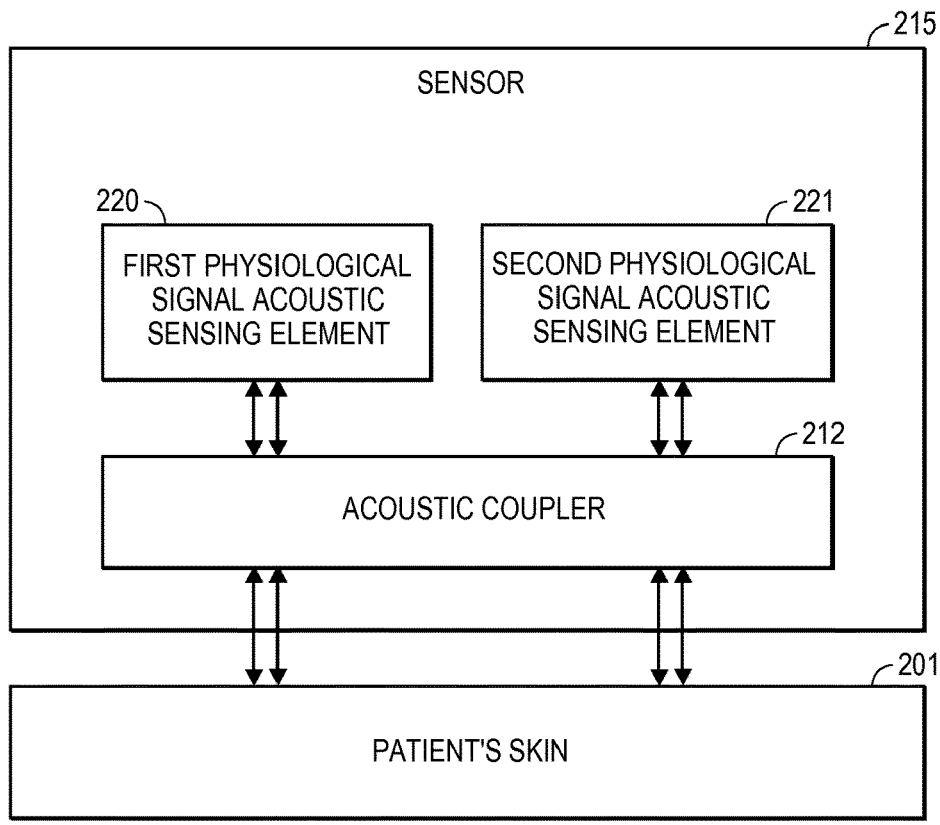
FIGS. 2A-2B are block diagrams of example embodiments of patient sensors that including first and second physiological signal acoustic sensing elements and at least one acoustic coupler for acoustically coupling both of the first and second physiological signal acoustic sensing elements to a patient's body.

FIG. 2A is a block diagram of an embodiment of a patient sensor 215 that includes first and second physiological signal acoustic sensing elements 220, 221. The sensing elements 220, 221 are generally adapted to detect physiological sounds from a patient 201, and can be any of the sensing elements described herein, such as piezoelectric membranes.

Figure 10:
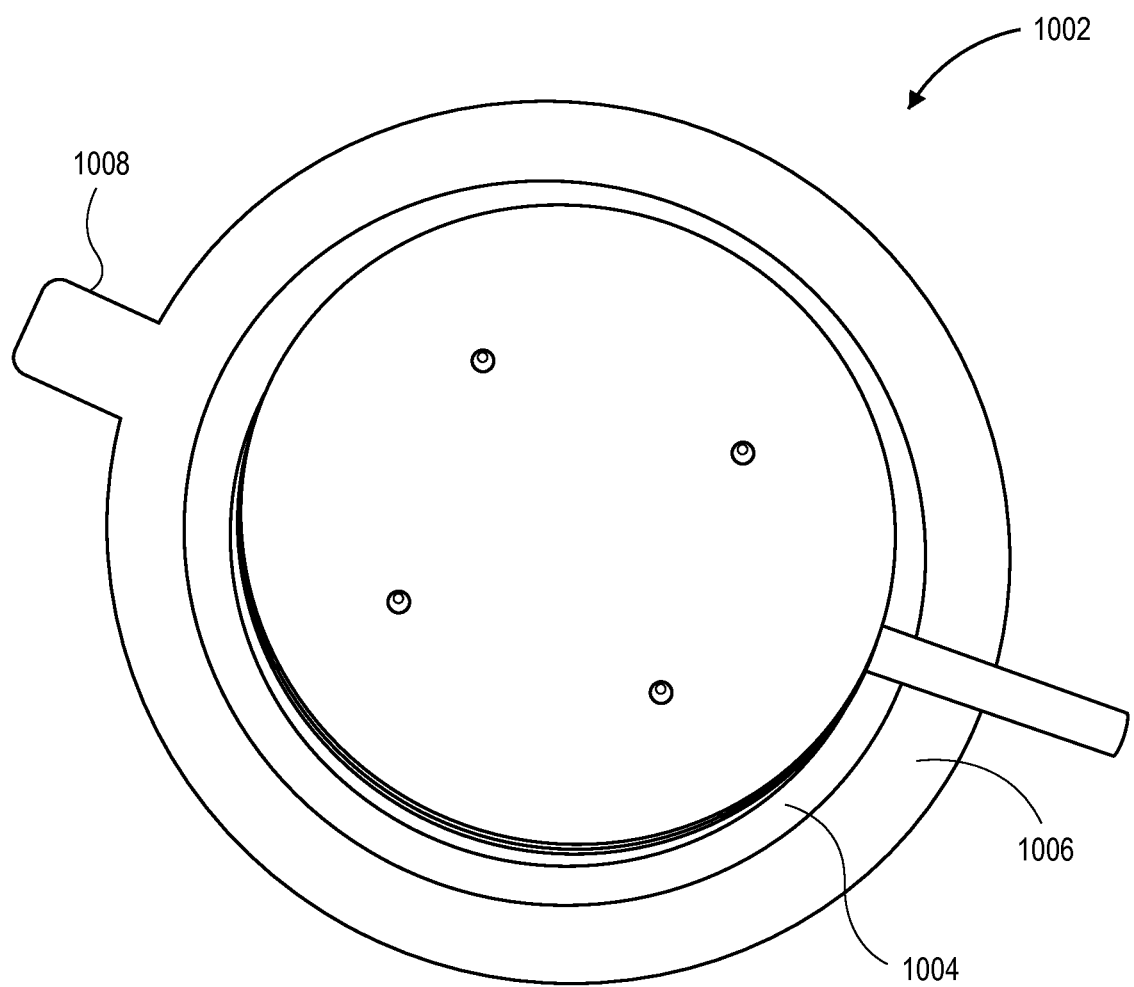
FIG. 10 is a top perspective view illustrating a sensor in accordance with an embodiment of the disclosure.

The patient sensor 215 can also include at least one acoustic coupler for acoustically coupling the first and second physiological signal acoustic sensing elements 220, 221 to a patient's body 201. In FIG. 2, both acoustic sensing elements 220, 221 are acoustically coupled to the patient. As shown in FIG. 10, the acoustic coupling can be achieved using a single acoustic coupler 212 for both sensing elements.

According to one configuration, the acoustic sensing elements 220, 221 are supported in a stacked configuration on a sensor frame (not shown) or other support. Example stacked configurations are described below with respect to FIGS. 3B, 4A-4B, 5E, and 6J-6M.

Figure 2B:
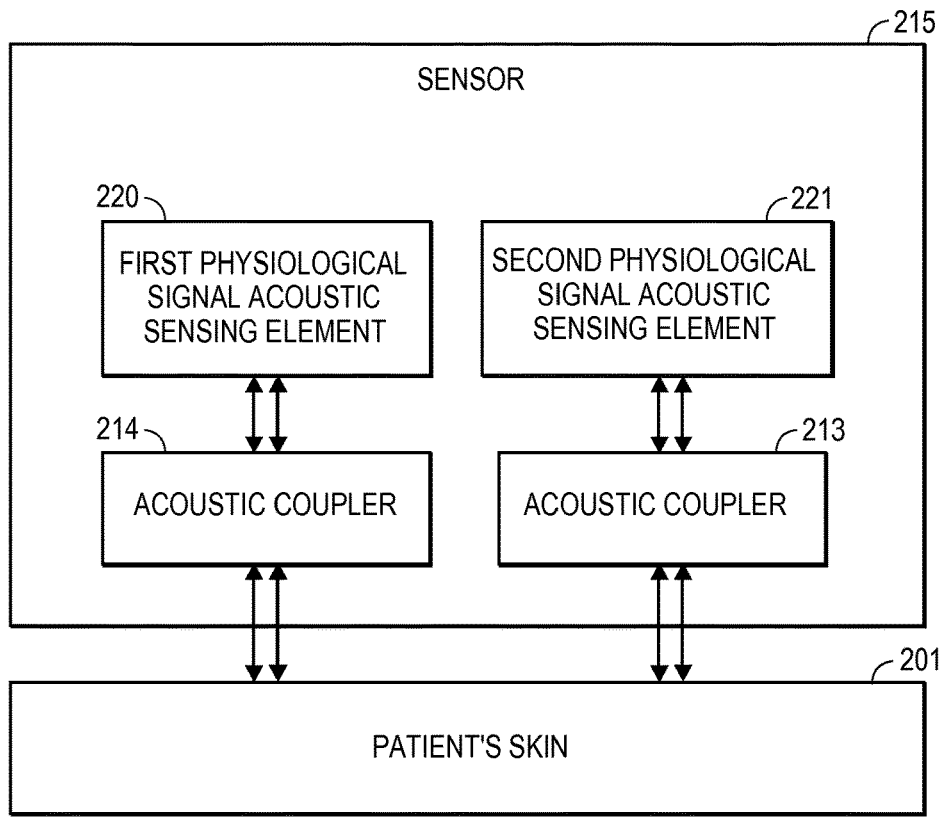

As shown in FIG. 2B, first and second acoustic couplers 213, 214 can be used in alternative embodiments. The acoustic couplers 213, 214 can be similar, for example, to the others described herein. In some embodiments, the acoustic sensing elements 220, 221 are supported in a side-by-side configuration on a frame. In some embodiments, one sensing element may not be acoustically coupled to the patient with an acoustic coupler. In other embodiments, no acoustic coupler is included.

In some embodiments, the acoustic coupler, or couplers, 213, 214 are designed to provide a substantially equal amount of coupling between each of the sensing elements 220, 221 and the patient's body 201, though this is not required. Example acoustic couplers compatible with the sensor 215 are described in greater detail throughout the disclosure.

As described, the first and second physiological signal acoustic sensing elements 220, 221 can be specially adapted to detect physiological sounds from a patient. However, the signals output by the acoustic sensing elements 220, 221 may also include noise (e.g., random noise, white Gaussian noise, etc.) from a variety of sources, which decreases the signal-to-noise ratio (SNR) of the signals.

The SNR of these signals can be improved, however, by collecting the desired physiological signal from more than one acoustic sensing element, and then combining (e.g., summing, subtracting, averaging, etc.) the respective outputs from the acoustic sensing elements in a manner that tends to reinforce the physiological signal components of the signals while tending to cancel or reduce the noise components of the signals. For example, the sensor 215, monitor, or other intermediate component, can include a noise attenuator which performs the combining of the signals from the sensing elements 220, 221 to achieve the improved SNR signal. Some embodiments of this approach are illustrated in FIGS. 3A-3B, 4A-4B and 6A-6M. Additional examples of combining signals from multiple sensing elements to achieve improved SNR and/or filter out ambient noise (or other types of noise) may be found in, for example, the application Ser. No. 12/904,931, titled Acoustic Respiratory Monitoring Sensor Having Multiple Sensing Elements, and filed Oct. 14, 2010, which was incorporated by reference herein above.

Generally, where sensors, sensing elements, couplers, etc., are described throughout the disclosure as being coupled to the patient's body, this may mean that one or more of the acoustic couplers are directly coupled to the patient's skin or other body part, such as where an acoustic coupler 212 is directly coupled to the skin 201 and transmits acoustic signals to one or more sensing elements 220, 221 as shown in FIG. 2A. However, this is not necessarily the case. For example, in some embodiments, the entire sensor, including couplers, where used, and/or sensing elements may be spaced from the patient's body and still receive acoustic signals emanating from the patient.

Figure 3A:
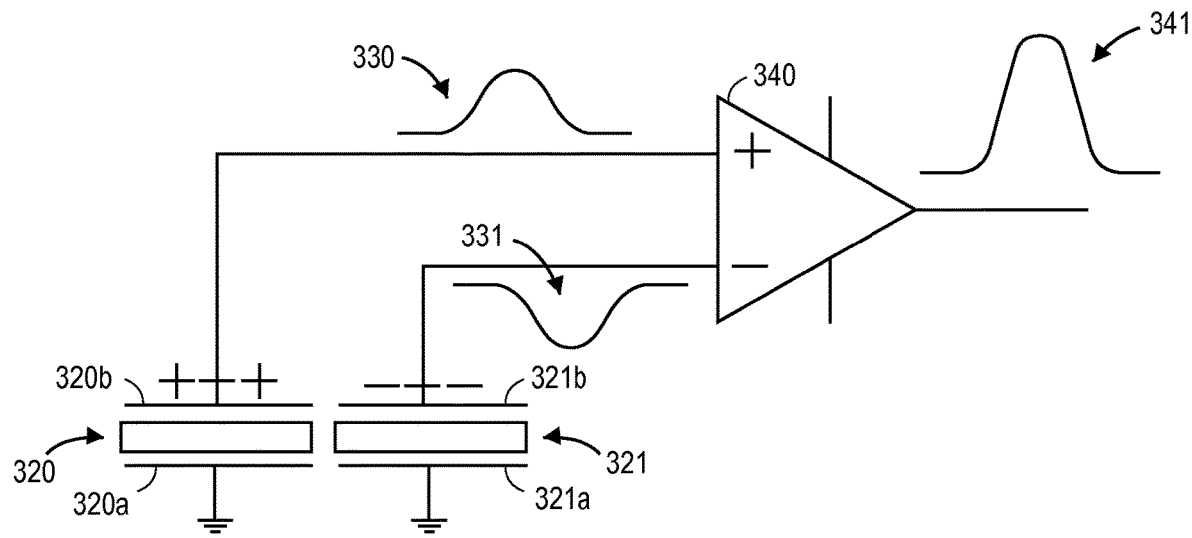
FIG. 3A is a schematic illustration of an embodiment of a circuit for improving signal-to-noise ratio by combining physiological signals from two or more acoustic sensing elements.

FIG. 3A is a schematic illustration of an embodiment of a circuit for improving signal-to-noise ratio by combining physiological signals from two or more acoustic sensing elements 320, 321. The two acoustic sensing elements 320, 321 may be acoustically coupled to the patient's body. In some embodiments, each of the first and second physiological signal acoustic sensing elements 320, 321 is a piezoelectric film, each having an anode and a cathode. The acoustic sensing elements 320, 321 detect physiological sounds from the patient's body and generate electrical waveforms corresponding to the physiological sounds. Example compatible piezoelectric films are described herein, with respect to FIGS. 4A-4B, 5A-5E, and 11A-11C, for example. Additional examples of compatible piezo electric films may be found in, for example, the '931 Application.

In FIG. 3A, the piezoelectric films 320, 321 are configured so as to generate output signals where the physiological signal components are 180° or approximately 180° out of phase. For example, in FIG. 3, the acoustic sensing elements 320, 321 generate voltage waveforms 330, 331 in response to physiological sounds from the patient. In the figure, the voltage waveform 330 is a positive pulse, while the voltage waveform 331 is a negative pulse, 180° out of phase from the positive pulse 330. Each of the physiological signal acoustic sensing elements 320, 321 is communicatively coupled to a sensing circuit 340. For example, the sensing circuit 340 may comprise or be referred to as a noise attenuator. Other example noise attenuators are described below with respect to FIGS. 7, 8, and/or 9A-9B, for example. In the illustrated embodiment, the sensing circuit 340 is a difference amplifier, though other sensing circuits 340 can be used.

In some embodiments, the 180° phase shift between the outputs from the two piezoelectric films 320, 321 is achieved by differentially connecting the piezoelectric films to the difference amplifier 340. For example, the cathode 320b of the first piezoelectric film 320 can be connected to the non-inverting terminal of the difference amplifier, while the anode 321a of the second piezoelectric film 321 can be connected to the inverting terminal of the difference amplifier 340. The anode 320a and the cathode 321b of the first and second films 320, 321, respectively, can be connected to ground (or be otherwise operatively coupled or coupled to a common potential). In some embodiments, the 180° phase shift is facilitated by mounting the two piezoelectric films 320, 321 such that one is flipped with respect to the other. For example, the two piezoelectric films 320, 321 can be mounted such that the cathode of one of the films faces toward the patient's body, while the anode of the other film faces toward the patient's body.

Since, in some embodiments, the physiological signal component of the second voltage waveform 331 is substantially a negative copy of the physiological signal component of the first voltage waveform 330, when these two waveforms 330, 331 are subtracted by the sensing circuit 340, they combine constructively, as indicated by the output waveform 341 from the sensing circuit 340. However, the outputs from the first and second piezoelectric films 320, 321 may also each include a noise component (not illustrated in the waveforms 330, 331). If the noise in the outputs from the piezoelectric films is random or otherwise uncorrelated, then at least a portion of the noise will tend to be combined destructively by the sensing circuit 340. Thus, the sensing circuit 340 can amplify the physiological signal component from the first and second piezoelectric films 320, 321 while attenuating random noise. The result in certain embodiments is that the physiological signal is emphasized while the random noise component of the output signals from the piezoelectric films 320, 321 is deemphasized.

For example, in one embodiment, the physiological signal is at least approximately doubled while the noise component is increased but less than doubled. The noise component might not double due to the random or uncorrelated nature of the noise, resulting in some portions of the noise combining additively while others combine negatively. Because the increase in the physiological signal can be greater than the increase in the noise, the sensor assembly configuration shown in FIG. 3A can improve signal to noise ratio (SNR).

Figure 3B:
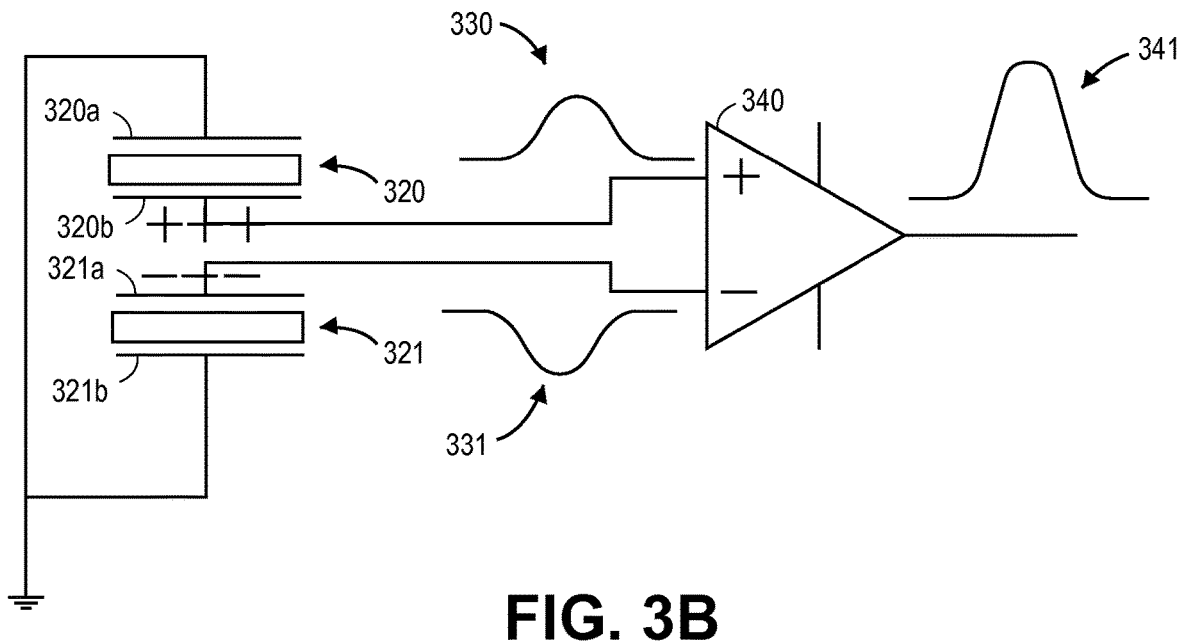
FIG. 3B is a schematic illustration of an embodiment of a circuit for improving signal-to-noise ratio by combining physiological signals from two or more acoustic sensing elements arranged in a stacked configuration.

While the configuration of FIG. 3A shows sensing elements 320, 321 in a side-by-side configuration, other configurations are possible. For example, FIG. 3B illustrates an embodiment of a circuit for improving signal-to-noise ratio where the sensing elements 320, 321 are in a stacked configuration with respect to one another. As described in further detail below with respect to FIGS. 4A-5B, the first sensing element 320 may be wrapped around a frame, and the second sensing element 321 may be wrapped around the first sensing element 320 and the frame.

Similar to the sensor configuration of FIG. 3A, the cathode 320b of the first piezoelectric film 320 can be connected to the non-inverting terminal of the sensing circuit 340, while the anode 321a of the second piezoelectric film 321 can be connected to the inverting terminal of the sensing circuit 340. Thus, in the illustrated embodiment the inner electrodes 320b, 321a of the first and second sensing elements 320, 321 generally face one another in the stacked configuration. The inner electrodes 320b, 321a are shown connected to the terminals of the sensing circuit 340, while the outer electrodes 320a, 321b are connected to ground.

Depending on the embodiment, the configuration shown in FIG. 3B can provide similar improved SNR advantages as described above with respect to FIG. 3A. In addition, as described herein (e.g., with respect to FIGS. 4A-5E, and 6J-6M), such a configuration can also provide enhanced electrical shielding. For example, the outer electrodes 320a, 321b of the sensing elements 320, 321, respectively, can be used to shield the inner electrodes 320b, 321a from electrical noise. As used herein, the terms "shield," "shielding," and the like, in addition to having their ordinary meaning, can mean reducing or attenuating noise, rather than completely eliminating noise. However, in some embodiments, the terms "shield," "shielding," and the like can also mean completely eliminating noise.

Generally, a variety of different sensing circuits 340 can be used in the embodiments of FIGS. 3A-3B and in generally any of the embodiments described herein where appropriate. Moreover, depending on the sensing circuit 340 used, the electrodes can be connected in a number of arrangements to achieve a similar SNR improvement. For example, a similar result could be obtained by connecting either both anodes or both cathodes, of the piezoelectric films 320, 321 to the inputs of a summing amplifier instead of a sensing circuit. In such embodiments, the physiological signal components of the outputs from the piezoelectric films can be approximately in phase and, therefore, can combine constructively when added by the summing amplifier. Still, at least a portion of random noise from the two output signals from the piezoelectric films 320, 321 will combine destructively, thereby attenuating noise and improving SNR. In some embodiments, more than two physiological signal acoustic sensing elements are used, and their inputs are summed together by, for example, a summing amplifier, a digital signal processor, etc. In some embodiments, one or more of the outer electrodes 320a, 321b can be operatively coupled to the sensing circuit 340, and one or more of the inner electrodes 320b, 321a are connected to ground. In yet other embodiments, the sensing circuit 340 comprises a coupling junction coupling together one or more of the electrodes of the respective sensing elements 320, 321.

Moreover, the number and arrangement of the sensing elements 320, 321 can vary according to certain aspects. For example, in some embodiments, more than two physiological signal acoustic sensing elements 320, 321 are used, and their inputs are summed together by, for example, a summing amplifier, a digital signal processor, etc. A variety of configurations including more than two sensing elements are possible. For example, in one embodiment a pair of stacked sensing elements is arranged in a side-by-side configuration on a frame with respect to another pair of stacked sensing elements. In other embodiments, more than two sensing elements (e.g., 3, 4, 5 or more) are arranged in a stacked configuration. In yet other embodiments, more than two sensing elements (e.g., 3, 4, 5 or more) are arranged side-by-side with respect to one another.

Figure 4A:
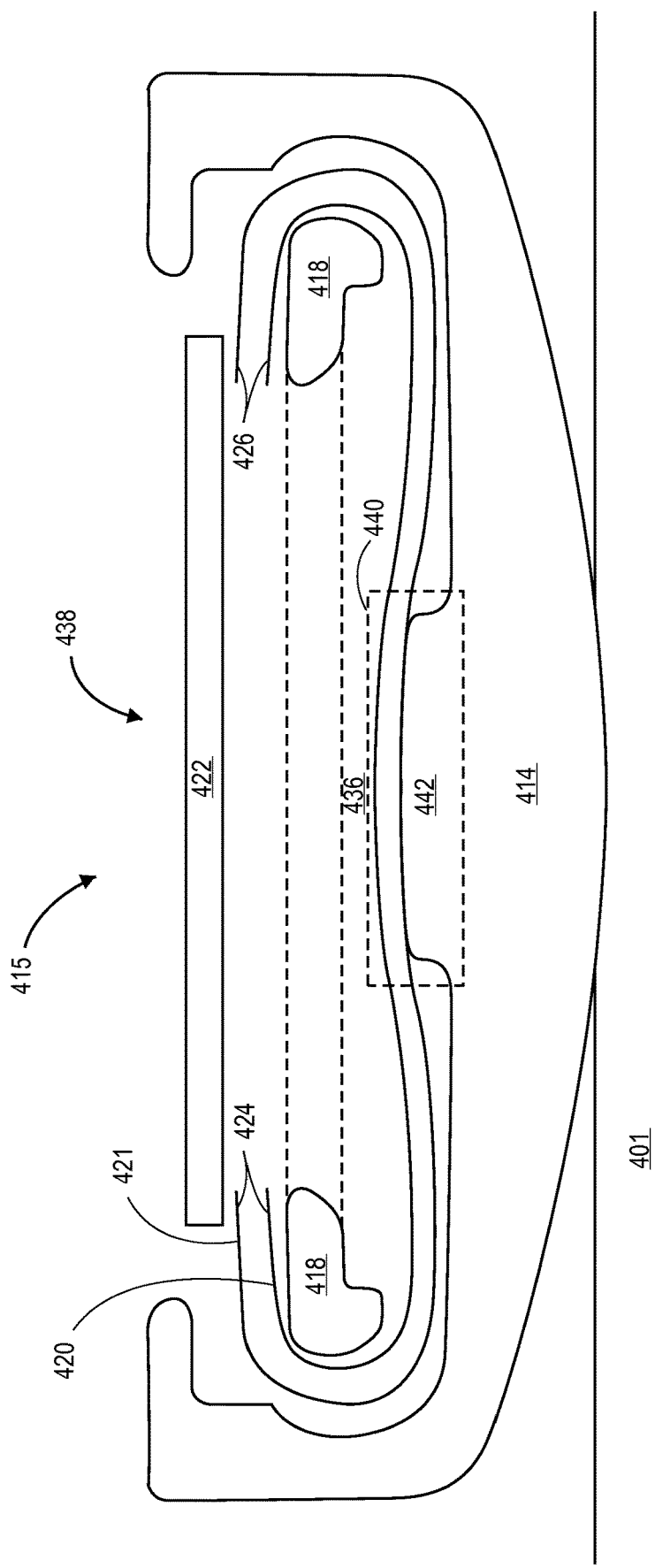
FIG. 4A is a cross-sectional schematic drawing of an embodiment of an acoustic sensor that includes first and second acoustic sensing elements in a stacked configuration.

FIG. 4A is a cross-sectional schematic drawing of an embodiment of an acoustic sensor 415 that includes first and second acoustic sensing elements 420, 421 in a stacked configuration. When connected to a sensing circuit (not shown, e.g., a difference amplifier) in the manner described above with reference to FIG. 3B, the acoustic sensor 415 can advantageously provide improved signal-to-noise ratio.

In the depicted embodiment, the first acoustic sensing element 420 is wrapped around a portion of the frame 418 and the second acoustic sensing element 421 is generally wrapped around the first acoustic sensing element 420 and also supported by the frame. In the illustrated embodiment, the physiological signal acoustic sensing elements 420, 421 are piezoelectric films. An acoustic coupler 414 acoustically couples the sensing elements 420, 421 to the patient's body 401, and can be aligned with both the first and second sensing elements 420, 421, as shown. The acoustic coupler may, in some embodiments, include an inner protrusion 442 that comes in contact with the first and second sensing elements 420, 421. In some other embodiments, an acoustic coupler 414 is not used. In the embodiment of FIG. 4A, the two piezoelectric films 420, 421 both extend over the acoustic cavity 436 of the frame 418. Thus, the films 420, 421 are free to respond to acoustic waves incident upon them, resulting in induced voltages.

In the depicted embodiment, a PCB 422 is disposed on top of the frame 418 at a position indicated by 438, and is in electrical contact with one or more of the electrodes of the first and second sensing elements 420, 421. For example, the PCB 422 can be in electrical contact with the anode and cathode of each of the sensing elements 420, 421. While other configurations are possible, first and second ends 424, 426 of the first and second sensing element 420, 421 can generally extend underneath opposite sides of the PCB 422.

The upper side of the first end 424 of the second sensing element 421 can include contacts (not shown) corresponding to electrodes of both of the sensing elements 420, 421. These contacts can be coupled to corresponding contacts on the underside of the PCB 422. Similarly, the upper side of the second end 426 of the second sensing element 421 can include contacts (not shown) corresponding to electrodes of both of the sensing elements 420, 421. These contacts can also be coupled to corresponding contacts on the underside of the PCB 422. One or more through holes or vias may be used to extend the electrodes on one or more sides of the sensing elements 420, 421 up to the upper side, enabling contact with appropriate PCB 422 contacts. Example first and second sensing elements compatible with the arrangement of FIG. 4A are described with respect to FIGS. 5A-5E. Additionally, another example piezoelectric membranes including through holes or vias are described below with respect to FIGS. 11A-11C.

While not shown for the purpose of clarity, in one embodiment, at least one additional layer (not shown) can be disposed between the sensing elements 420, 421. The additional layer can include an adhesive that adhesively couples the sensing elements 420, 421 together. This adhesive coupling can help ensure that the sensing elements 420, 421 move uniformly together in response to vibrations, reducing losses and improving the response of the sensor. The adhesive coupling can also at least partially maintain tension of one or more of the sensing elements 420, 421.

The additional layer can further be configured to insulate the sensing elements 420, 421 from one another, preventing shorts, noise and/or other undesirable electrical behavior. For example, the additional layer can include a dielectric material. In an embodiment, the adhesive described above acts as a dielectric material. Additional adhesive layers are described below with respect to FIGS. 6A-6M, and FIGS. 12A-12L, for example.

The ends of the sensing elements 420, 421 may be configured to provide improved sensor performance, reliability, etc. For example, the additional layer may extend to the ends of one or more of the sensing element 420, 421. In one embodiment, the additional layer is an adhesive layer extending to the underside of the second end 426 of the second sensing element 421, helping secure the connection between the second sensing element 421 and the PCB 422.

Depending on the embodiment, one or more of the ends of the sensing elements 420, 421 can also include a dielectric material. For example, in one embodiment, the underside of the second end 426 of the second sensing element 421 includes a dielectric material, thereby insulating the second end 426 and the PCB 422. Additionally, the electrode coatings can be configured to reduce the possibility of electrical shorts or other undesirable behavior. In one embodiment, for example, the electrode coating on the underside of the second sensing element 421 does not extend to the second end 426, thereby reducing the risk of undesirable electrical contact between the second end 426 and the top surface of the PCB 422. In another embodiment, a dielectric material is placed on the underside of the PCB 422 instead of or in addition to providing a dielectric material on the end of the sensing element 420 or 421.

A variety of other configurations are possible for the arrangement of the sensing elements 420, 421. For example, in one embodiment, the ends of the sensing elements 420, 421 which are not connected to the PCB 422 do not extend over or under the PCB 422. In another embodiment, each end of the sensing elements 420, 421 includes one electrode contact, and all four ends are thus in electrical contact with corresponding contacts on the PCB 422. This is in contrast with the arrangement described above, in which the upper side of the first and second ends 424, 426 of the second sensing element 421 each include electrode contacts for the sensing elements 420, 421.

As discussed, and as with many of the embodiments described herein, the piezoelectric films 420, 421 are shown in FIG. 4A spaced apart for clarity and ease of illustration. However, in addition to the additional layers described above, the two piezoelectric films 420, 421 can be separated by one or more mechanical supports, acoustic decouplers, shielding layers, or other layers or components. Additionally, any of these layers may be disposed between the frame 418 and the first piezoelectric film 420 and/or wrapped around the outside of the second sensing element 421.

Example Shielding Using Multiple Sensing Elements

In certain embodiments, multiple sensing elements can be employed to form an electrical noise shielding barrier, providing electrical shielding. Moreover, using the sensing elements or portions thereof to form the barrier can simplify the design of the sensor, reducing costs. For example, one or more stacked sensing elements can be configured to electrically shield the sensor. In some configurations, where the stacked sensing elements are piezoelectric films, the inner, facing electrodes of the films in the stack are used to communicate voltage signals generated by the piezoelectric elements to the sensing circuitry of the sensor (and/or monitor). The outer electrodes of the films in the stack can advantageously be configured to shield the inner electrodes from electrical noise. Generally, throughout the disclosure, the term "inner" refers to the sensing element surface and/or electrode coating which is facing the other sensing element in the active region of the stack (e.g., across the acoustic cavity). Conversely, the term "outer" refers to the sensing element surface and/or electrode which is facing away from the other sensing element in the active region of the stack.

The electrical noise shielding barrier can electrically shield the electrical poles of the sensing element from external electrical noises. In some embodiments the outer portions of the sensing element form a Faraday cage or shield around the inner portions. Thus, the outer portions can distribute external electrical noise substantially equally to the electrical poles of the piezoelectric sensing element. The shield can act to reduce the effect of noise on the sensing element from sources such as external static electrical fields, electromagnetic fields, and the like.

Using a second sensing element to form an electrical shielding barrier can also help to reduce costs by reducing the complexity involved in constructing the sensor and reducing material costs. For example, such embodiments may not include one or more shielding layers which are physically separate from the sensing elements (e.g., copper shielding layers), reducing manufacturing costs associated with purchasing and handling such components. However, certain aspects of shielding barriers formed from multiple sensing elements described herein are compatible with shielding barriers formed from separate layers and aspects thereof. Example shielding barriers including those formed from separate shielding layers are described throughout the '939 application, including, without limitation, paragraphs [0120]-[0146] and FIGS. 2D-2E of the '939 application which are incorporated by reference herein.

FIG. 4B shows a partial cross-sectional schematic drawing of a portion 440 of the first and second stacked piezoelectric films 420, 421 of FIG. 4A. As shown, each of the first and second piezoelectric films 420, 421 respectively include an anode 420a, 421a and a cathode 420b, 421b on opposing sides of the films 420, 421. In some embodiments, the films 420, 421 include one of the piezoelectric films described in the present disclosure.

As shown, the films 420, 421 are disposed with respect to each other in a stacked configuration such that the cathode 420b of the first film 420 is facing the anode 421a of the second film 421. Thus, these two inner electrodes 420b, 421a of the stack are generally sandwiched between the anode 420a of the first film 420 and the cathode 421b of the second film 421, which form the outer electrodes of the stack. The inner electrodes 420b, 421a can be operationally coupled to a sensing circuit (e.g., a differential amplifier) in the manner shown in FIG. 11B, advantageously providing improved signal-to-noise-ratio in some embodiments.

In addition, the outer electrodes 420a, 421b of the films 420, 421 can be configured to form layers of an electrical noise shielding barrier, providing the additional benefit of electrically shielding the sensor from external electrical noises. The electrical noises shielded (or at least partially shielded) can include electromagnetic interference (EMI) from various sources, such as 50 or 60 Hz (AC) noise, noise from other medical devices, and so forth. In some embodiments for example, the outer electrodes 420a, 421b of the first and second films 420, 421 form a barrier around the inner electrodes 420b, 421a of the first and second films 420, 421. Thus, a significant amount of external electrical noise is not directly incident on the inner electrodes 420b, 421a. The outer electrodes 420a, 421b can, for example, distribute at least a portion of the external electrical noise substantially equally to the inner electrodes 420b, 421a, which form the electrical poles of the sensor. For example, because the outer electrodes 420a, 421b may share a common potential (e.g., ground), noise incident on either of the outer electrodes 420a, 421b can be distributed equally to each electrode 420a, 421b. The equally distributed noise can then be capacitively coupled to the inner electrodes 420b, 421a.

Thus, in certain embodiments, because the noise is equally distributed, the noise signal components on the inner electrodes 420b, 421a will be substantially in phase. The physiological signal components can be substantially out of phase, on the other hand, due to the differential orientation of the inner electrodes 420b, 421a with respect to one another in some implementations. The noise signals can advantageously be removed or substantially removed, such as through a common-mode rejection technique as described herein. In certain embodiments, at least some of the external electrical noise is shunted or otherwise directed to ground instead of, or in addition to, being equally distributed to the inner electrodes 420b, 421a.

A variety of alternative configurations are possible. For example, more than two sensing elements (e.g., 2, 3, 4, 5 or more) may be arranged to provide electrical shielding and/or improved signal-to-noise ratio in some embodiments. Moreover, the particular polarities of the sensing elements 420, 421 of FIG. 4B are not intended to be limiting. In another embodiment, one or more of the sensing elements 420, 421 are flipped. For example, the sensing elements 420, 421 are flipped such that the anode 420a of the first sensing element 420 faces the cathode 421b of the second sensing element 421.

Additionally, shielding barriers formed using stacked sensing elements 420, 421 can provide improved coupling of bodily sounds to the sensor, improving sensor operation (e.g., sensor sensitivity, measurement reliability, etc.). Generally, portions of both the shielding barrier and the sensing element will tend to vibrate in response to the patient sounds. Thus, an uneven mechanical response between the shielding barrier and the sensing element may result in lost signal, affecting sensor performance. For example, shielding barriers including layers that are physically separate from the sensing element can be, in some cases, relatively stiffer than the sensing element. This can limit movement of the sensing element in response to vibrations, producing a corresponding limiting affect on sensor sensitivity. In contrast, where electrodes of the sensing elements are used as shielding layers, the shielding barrier and the sensing element are generally formed from the same type material and integrally connected. Thus, the sensor may be relatively more responsive to vibrations, improving sensor operation.

Moreover, each of the outer electrode shield layers in the stacked configuration can be evenly spaced from the respective inner electrode sensor poles, particularly across the mechanically active portions of the sensor (e.g., across the frame cavity 436 of FIG. 4A). The capacitance between the shield layer and sensor pole on a first side of the sensing element stack can be very highly matched (e.g., substantially equal to) with the capacitance between the shield layer and sensor pole on the opposing side of the stack. Thus, a stacked sensing element configuration can provide a more even distribution of external electrical noise to the poles of the sensing element, improving noise rejection.

According to certain aspects, the physical configuration of the electrodes of the first and second films 420, 421 can be tailored to provide improved electrical shielding. For example, the outer electrodes 420*b*, 421*a* can be plated using a material selected to provide enhanced shielding. Although other materials may be used, in one embodiment, the outer electrodes 420*b*, 421*a* are plated with silver ink. Moreover, in certain embodiments, the outer electrode coatings of the piezoelectric stack cover a greater portion of the surface area of the respective piezoelectric films than the inner electrode coatings. For example, the outer electrode coatings may cover a significantly larger portion of the surface area of the respective piezoelectric films than the inner electrode coatings. In certain embodiments, for example, the outer electrodes generally envelope or surround the inner electrodes or a substantial portion thereof when the films 420, 421 are in a stacked configuration. Thus, the amount of surface area of the inner electrodes which is exposed to electrical noise is reduced due to the mechanical and/or electrical barrier created by the surrounding outer electrodes.

Figure 5A:
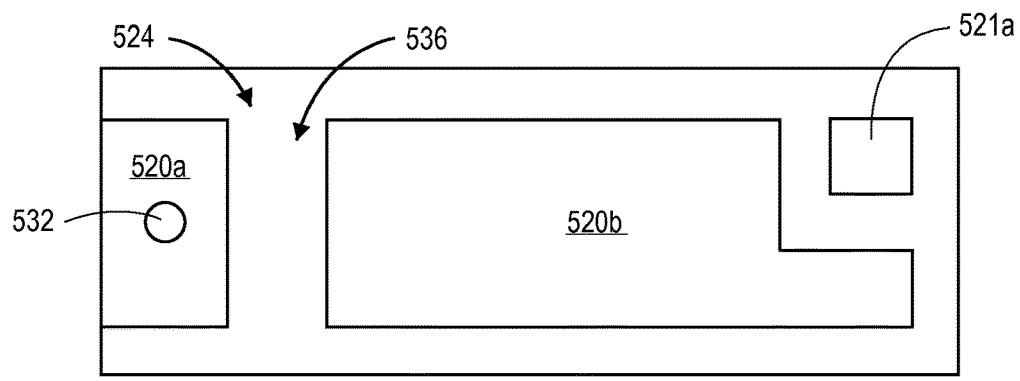
FIGS. 5A-5D show views of example acoustic sensing elements having electrode coating configurations tailored for use in a stacked configuration.
Figure 5B:
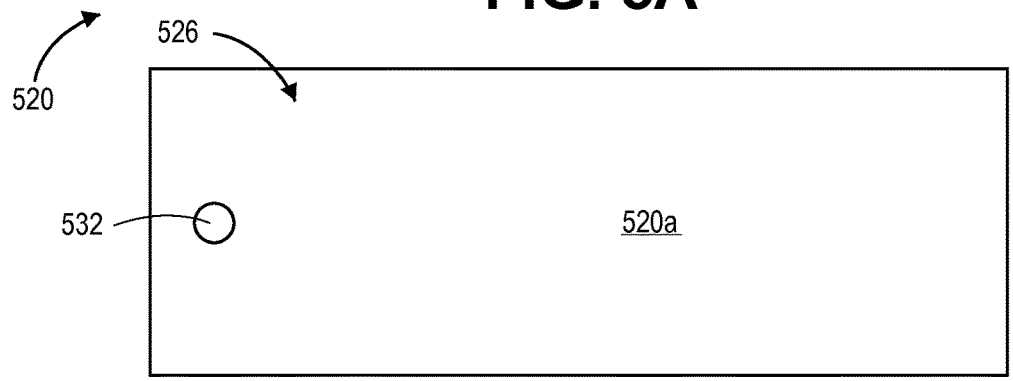
Figure 5C:
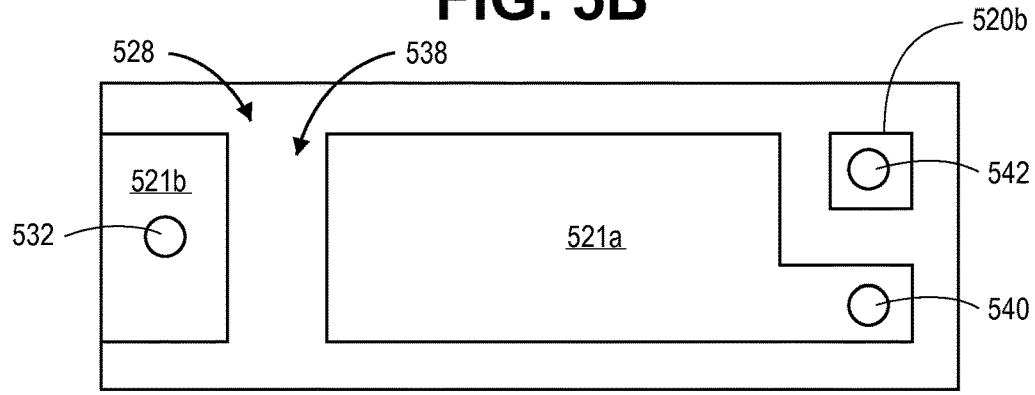
Figure 5D:
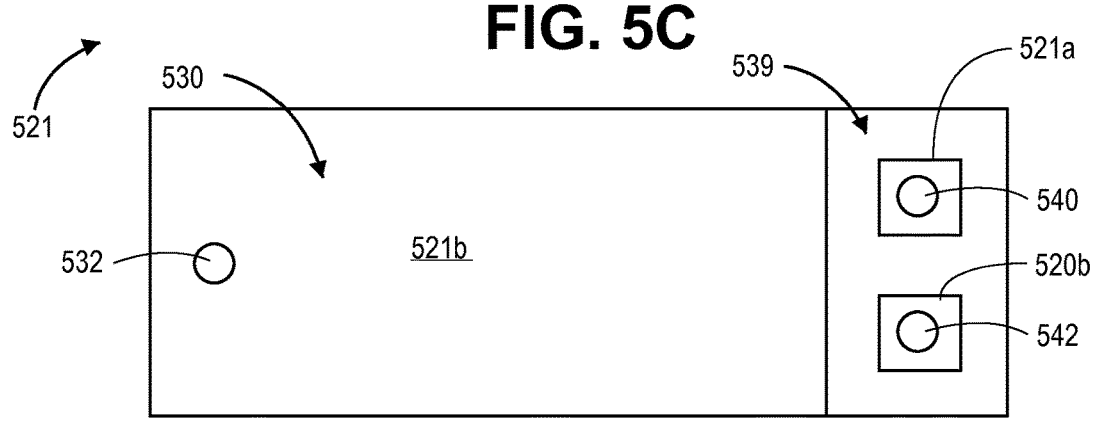

FIGS. 5A-5D illustrate example sensing elements 520, 521 having electrode coating configurations tailored for use in a stacked configuration. FIGS. 5A-5B show example first and second (e.g., inner and outer) surfaces 524, 526 of a first example acoustic sensing element 520. FIGS. 5C-5D show example first and second (e.g., inner and outer) surfaces 528, 530 of a second acoustic sensing element 521. While the films 520, 521 are shown in an unfolded configuration for the ease of illustration, the second sensing element 521 may be wrapped around the first sensing element 520 on a frame as shown in FIG. 4A. Thus, the sensing elements 520, 521 are also referred to as the interior and exterior sensing elements, respectively.

The interior sensing element 520 includes an anode electrode coating 520*a* on the outer surface 526 which extends via a through hole 532 to a portion on one end the end of the inner surface 524. The inner surface 524 of the interior sensing element 520 also includes a cathode coating 520*b*. The exterior sensing element 521 includes an cathode electrode coating 521*b* on the outer surface 530 which extends via a through hole 532 to a portion on one end of the inner surface 528. The inner surface 528 of the exterior sensing element 521 also includes an anode electrode coating 521*a*.

The outer surface 530 of the exterior sensing element 521 includes electrode contact 521*a* which extends via a through hole 540 to the anode electrode coating 521*a* on the inner surface 528. The outer surface 530 of the exterior sensing element 521 also includes electrode contact 520*b* which extends via a through hole 542 to the cathode electrode coating 520*b* on the inner surface 536 of the interior sensing element 520.

Accordingly, the outer surface 530 of the exterior sensing element 521 includes contacts for each of: a common connection to the anode coating 520*a* and cathode coating 521*b*, a connection to the cathode coating 520*b*, and a connection to the anode coating 521*a*.

Figure 5E:
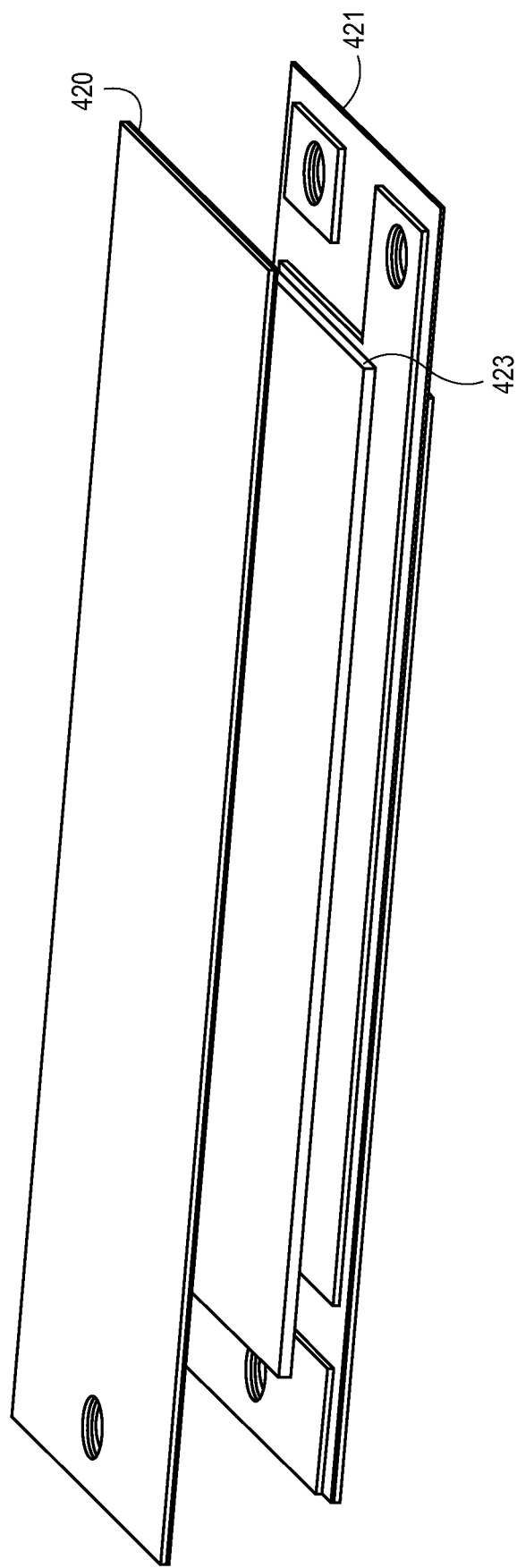
FIG. 5E shows a perspective view of the example acoustic sensing elements of FIGS. 5A-5D in a stacked configuration.

FIG. 5E shows a perspective view of the example acoustic sensing elements of FIGS. 5A-5D described above, in a stacked configuration as shown and described with reference to FIGS. 4A-4B above. The first sensing element 420 (corresponding to the interior sensing element 520 of FIGS. 5A-5B) is shown at the top of the stack. The second sensing element 421 (corresponding to the interior sensing element 521 of FIGS. 5C-5D) is shown at the bottom of the stack. In middle of the stack is shown the adhesive layer 423. As described above with reference to FIGS. 4A-4B, the stacked sensing elements may be, in an embodiment, wrapped around the frame 418 such that electrical contacts on the outer surface of the exterior sensing element come in contact with electrical contacts on the underside of the PCB 422. In another embodiment, and as described below in reference to FIG. 6M, the stacked sensing elements, as shown in FIG. 5E, may not wrap around the frame 418, but may be configured in a flat arrangement, sandwiched between the frame 481 and the PCB 422. In this embodiment, the stack of sensing elements of the FIG. 5E may be flipped, such that the electrical contacts on the outer surface of the exterior sensing element come in contact with electrical contacts on the underside of the PCB 422.

As shown in FIG. 5B, the outer electrode surface of the first (interior) film 520 covers a substantially greater percentage of the surface area of the outer surface 526 of the film 520 than do the inner electrode surfaces on the opposing, inner surface 524 of the film 520, shown in FIG. 5A. For example, in the illustrated embodiment, the outer electrode coating shown on FIG. 5B covers substantially the entire outer surface 526 area of the film 520, while the electrode coatings on the inner surface 524 form three generally rectangular coatings covering only a portion of the inner surface 524 area of the film 520. Similarly, as shown in FIGS. 5C-D, the outer electrode coatings on the outer surface 530 of the second (exterior) film 521 covers a substantially greater surface area of the outer surface 530 of film 521 than the inner electrode coating on the inner surface 528 of the film 521. For example, in certain embodiments, the electrode coating on the exterior surface of one or more of the films 520, 521 covers at least 2 percent more of the film surface area than do the interior electrodes. In other embodiments, the exterior electrodes cover at least 1, 5, 10, 15 or greater percent more of the exterior surface area than do the interior electrodes. Additionally, the exterior electrode can cover at least 90 percent of the exterior film surface in some embodiments. In other embodiments, the exterior electrode covers at least 70, 75, 80, 85, 95 or more percent of the exterior film surface.

As described with respect to FIGS. 4A-4B, the through holes 532, 540, 542 facilitate electrical contact between the respective electrodes and one or more components of the sensor (e.g., a PCB contact). Moreover, electrodes which extend to others sides through the through holes can be electrically isolated from the other electrodes on the respective films the by gaps 536, 538, 539 in the electrode coatings.

In such embodiments, where an electrode coating covers substantially the entire surface area of the piezoelectric film, or otherwise covers a significantly larger portion of the surface area of the piezoelectric film than the electrode coating on the opposing side, the electrode coating may be referred to as "flooded." Thus, the configuration of FIGS. 5A-5D generally includes un-flooded inner electrodes generally sandwiched between flooded outer electrodes. Such configurations can reduce surface area of the inner electrodes that is exposed to electrical noise, improving electrical shielding.

A wide variety of flooded electrode configurations are possible. For example, in some embodiments, the sizes and shapes of the electrode coatings may differ from the illustrated embodiment. The relative sizes of the inner electrode coatings versus the outer electrode coatings can also vary. For example, the inner electrode coatings are much smaller in relation to the outer electrode coatings than is shown.

In some alternative embodiments, the outer and inner electrode coatings are both flooded or otherwise cover about the same surface area, or the electrode coating on the inner electrode coating covers more surface area than the outer electrode. Such embodiments may, in some cases, provide relatively less shielding than embodiments where the outer electrode coatings cover more surface area than the inner electrodes, but nonetheless provide some significant amount of electrical shielding.

First Example Sensor

Figure 6A:
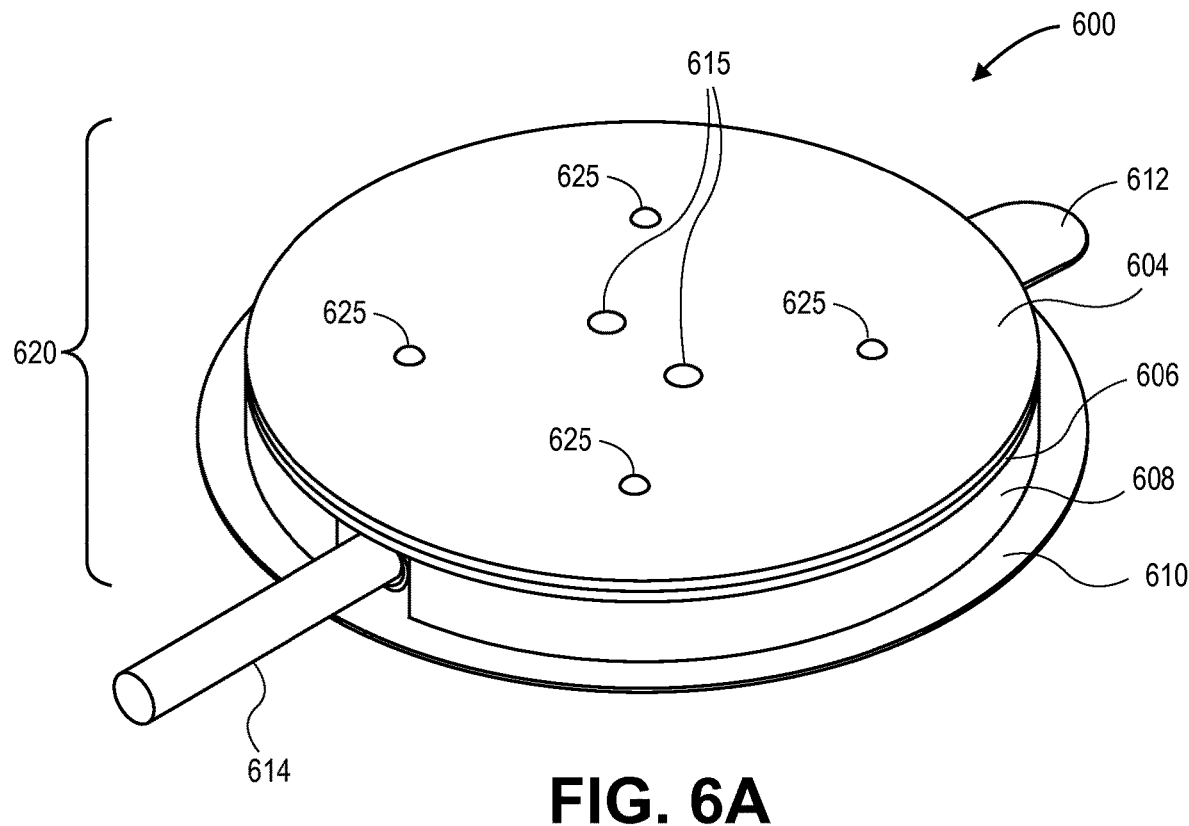
FIGS. 6A-6B are top and bottom views, respectively, of a sensor incorporating multiple sensing elements in accordance with embodiments described herein.
Figure 6B:
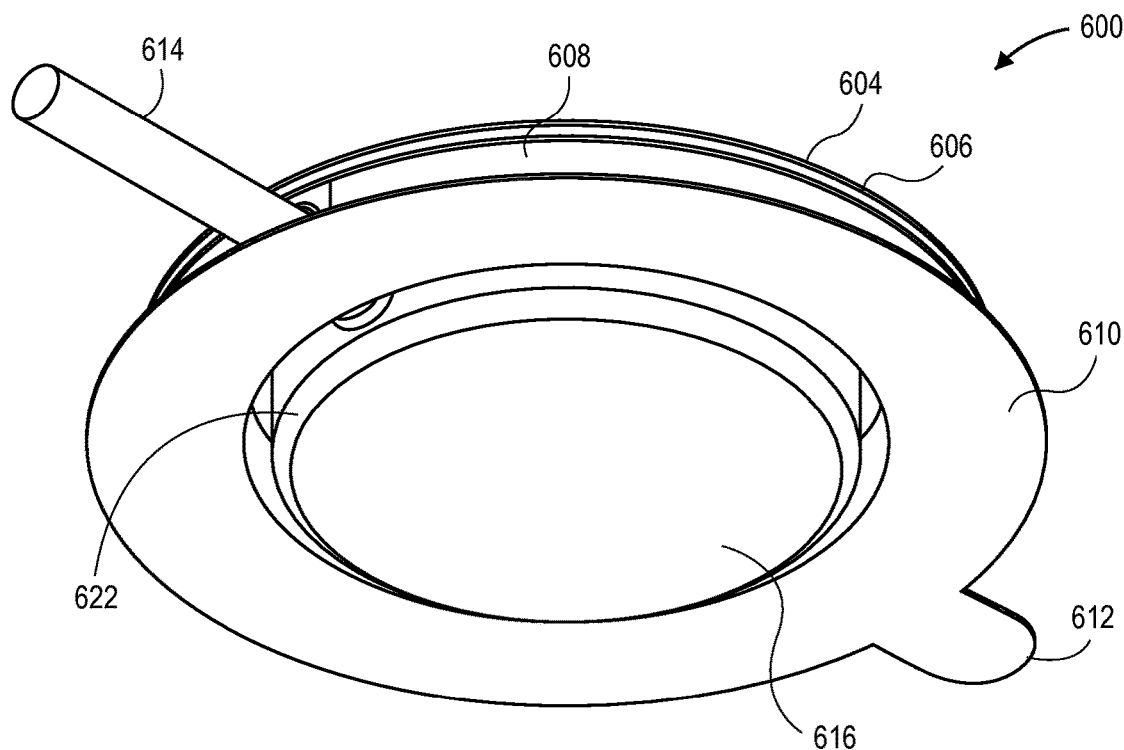

FIGS. 6A-6B are top and bottom views, respectively, of an embodiment of a sensor 600 that can detect acoustic physiological sounds from a patient and incorporating an attachment sub-assembly 620, an acoustic coupler 616 including an at least partially spherical cap, multiple sensing elements, and certain other beneficial aspects described herein. For example, the sensor 600 can provide improved SNR using the sensing elements according to techniques described above with respect to FIGS. 2A-4B. Moreover, the sensor 600 can include a stacked, multiple sensing element configuration providing enhanced shielding, compatible with the techniques described above with respect to FIGS. 4A-5E. Additionally, as is described below in reference to FIGS. 6A-6M, the sensor 600 can include a large acoustic coupler 616 with an at least partially spherical or rounded cap and a deformable attachment sub-assembly 620 that can provide enhanced patient and acoustic coupling that can provide improved SNR and coupling even when the patient moves, among other possible advantages. Although the cap may be at least partially spherical or otherwise rounded (e.g., convex), for conciseness, the remainder of this specification shall refer to the cap as being a spherical cap.

The sensor 600 is generally attachable to a patient and can be coupled to a patient monitor. For example, the sensor 600 can be used with the system 10 of FIGS. 1A-1B. Additionally, the sensor 600 may be compatible with the sensor system 100 of FIG. 10. For example, the sensor 600 may be the sensor 101 of FIG. 10, and may be attached to the patient via an adhesive portion, such as the attachment portion 106 of FIG. 10. The sensor 600 may also be referred to as an acoustic sensor.

As will be described in greater detail herein, in an embodiment, sensor 600 includes one or more sensing elements, such as, for example, one or more piezoelectric devices or other acoustic sensing devices. The sensing elements generate voltages or currents that are responsive to vibrations generated by the patient, and the sensor 600 includes circuitry to transmit the voltage generated by the sensing element to a processor for processing. In an embodiment, the sensor 600 includes circuitry for detecting and transmitting information related to biological sounds to a physiological monitor. These biological sounds may include heart, breathing, and/or digestive system sounds, in addition to many other physiological phenomena. The sensor 600 in certain embodiments is a biological sound sensor, such as the sensors described herein. In some embodiments, the biological sound sensor is one of the sensors such as those described in the '883 Application. In other embodiments, the sensor 600 is a biological sound sensor such as those described in U.S. Pat. No. 6,661,161, which is incorporated by reference herein. Other embodiments include other suitable acoustic sensors Referring now specifically to the FIGS. 6A and 6B, the sensor 600 fully assembled is shown. In various embodiments, the sensor 600 includes an attachment sub-assembly 620 and a sensor sub-assembly 622. The attachment sub-assembly 620 includes a cap 604, a cap adhesive 606, a deformable patient coupler 608 (also referred to herein as the stretchable patient coupler 608), and an adhesive portion 610. The adhesive portion 610 further includes a pull tab 612. In an embodiment, the cap 604 and cap adhesive 606 may include pressure equalization pathways 615. The sensor sub-assembly 622 includes an acoustic coupler 616 and can include other components that are further described below. A sensor cable 614 may be coupled to one or more components of the sensor 600 and may, in an embodiment, attach to the sensor sub-assembly 622 through an opening in the attachment sub-assembly 620 as shown.

Figure 6C:
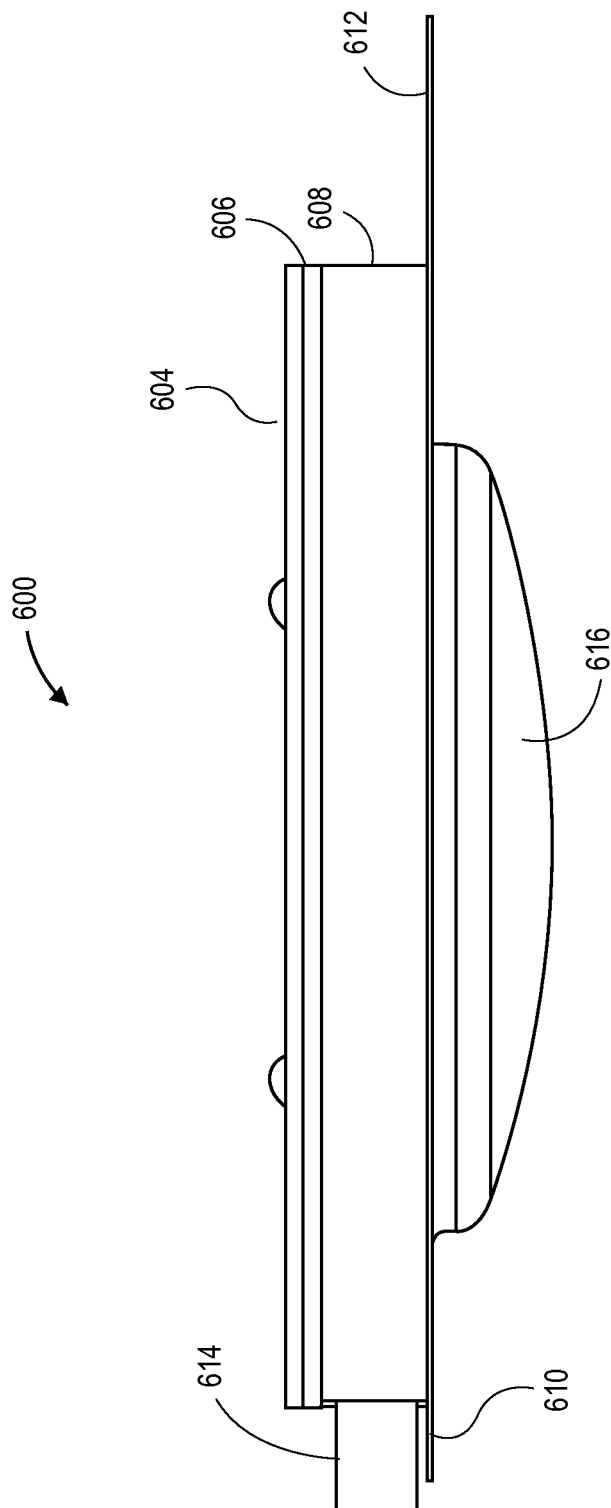
FIG. 6C shows a side view of the sensor of FIGS. 6A-6B.

FIG. 6C shows an example side view of the fully assembled sensor 600 of FIGS. 6A and 6B. As shown, the acoustic coupler 616 of the sensor sub-assembly 622 generally protrudes from a bottom side of the sensor 600, and includes a bottom portion with a spherical, semi-spherical, rounded, or otherwise convex shape (referred to hereinafter as semi-spherical for conciseness). The semi-spherical shape of the bottom portion of acoustic coupler 616 may be referred to herein as a spherical cap. In general, and as is described in further detail below, when the sensor 600 is applied to the patient, the adhesive portion 610 attaches the sensor 600 to the patient's skin and the acoustic coupler 616 is at least partially compressed into the attachment sub-assembly 620. The deformable patient coupler 608 of the illustrated embodiment comprises a deformable, elastic, and/or foam or foam-like material that may stretch and deform so as to enable substantially even and constant coupling of the sensor 600 to the patient. Additionally, the large spherical cap of the acoustic coupler 616 can advantageously enable improved coupling of acoustic signals from the patient to the sensor 600.

Figure 6D:
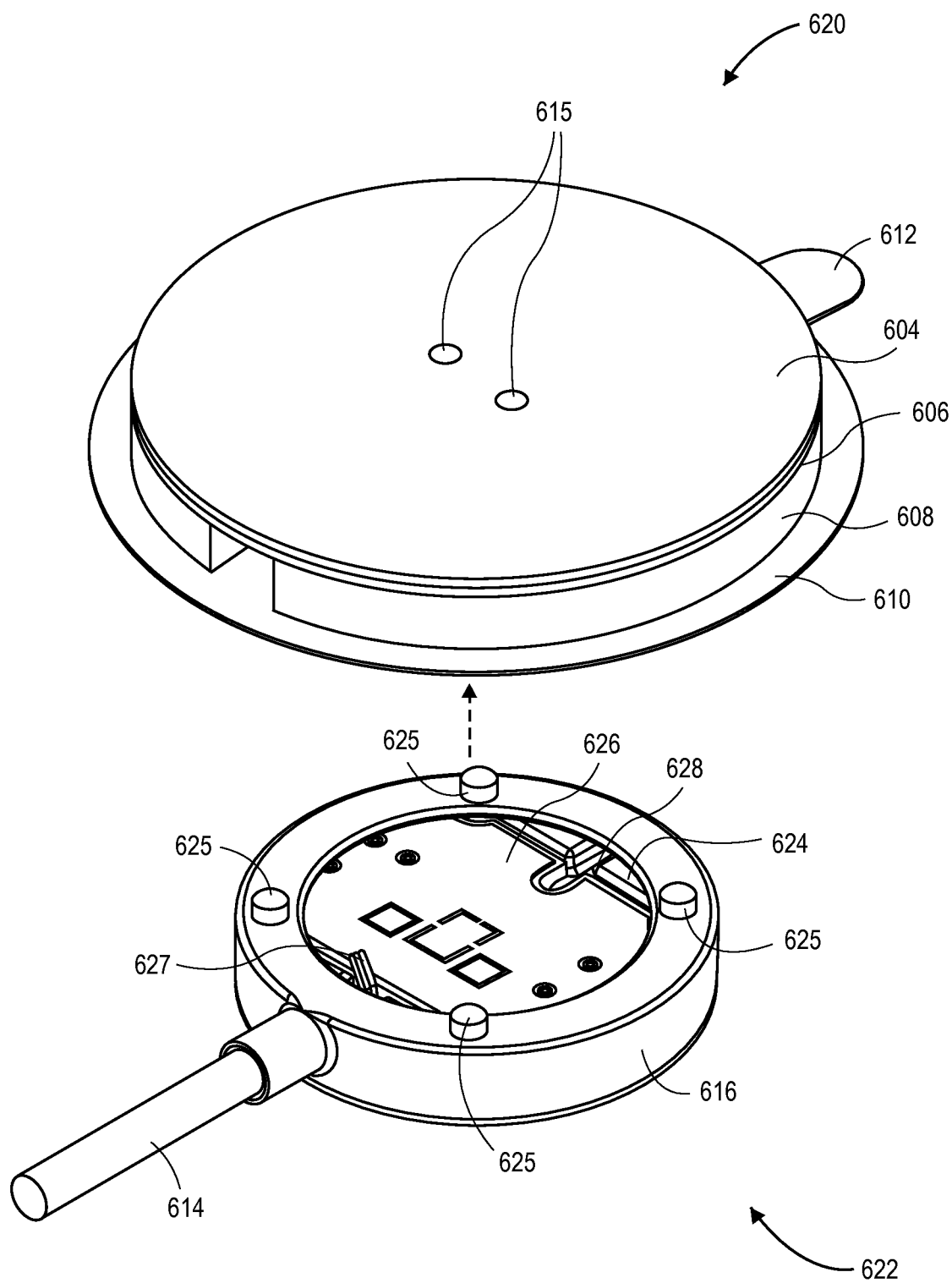
FIGS. 6D-6E are top and bottom partially-exploded, perspective views, respectively, of the sensor of FIGS. 6A-6B, in accordance with embodiments described herein.
Figure 6E:
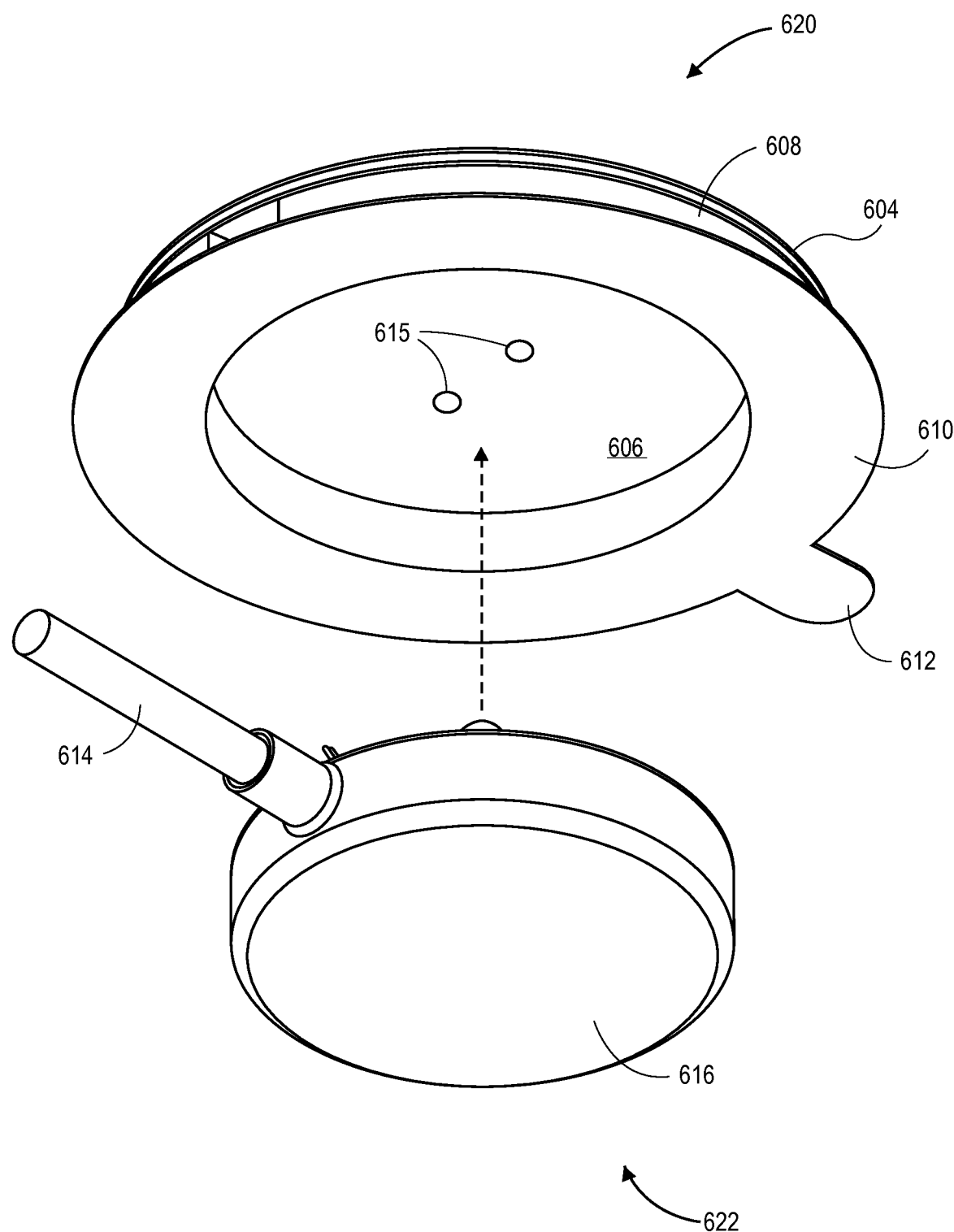

FIGS. 6D-6E show top and bottom partially-exploded, perspective views, respectively, of the sensor 600, in accordance with embodiments of the present disclosure. As shown, the sensor 600 may be composed of two sub-components or sub-assemblies, the attachment sub-assembly 620 and the sensor sub-assembly 622. In FIGS. 6D-6E, each of the attachment sub-assembly 620 and the sensor sub-assembly 622 is shown in their individual, fully assembled states. The attachment sub-assembly 620 includes each of the components mentioned above (including the cap 604, cap adhesive 606, deformable patient coupler 608, adhesive portion 610, pull tab 612, and optional pressure equalization pathways 615), while the sensor sub-assembly 622 includes the acoustic coupler 616, one or more locking posts 625, a frame 624, a printed circuit board (PCB) 626, stacked sensing elements (not shown), and an optional pressure equalization pathway 628 (among other components that are shown and described below).

Referring to FIG. 6E, indicated by the dashed arrow, during assembly the sensor sub-assembly 622 may attach to the attachment sub-assembly 620 so that it is positioned inside of a cavity defined by the underside of the cap adhesive layer 606 and the interior sidewalls of the deformable patient coupler 608. After being positioned with the cavity, the attachment sub-assembly 620 at least partially surrounds, encompasses, encases, and/or forms a shell around and/or over the top and sides of the sensor sub-assembly 622.

According to the illustrated embodiment, the top of the sensor sub-assembly 622 contacts the cap 604 of the attachment sub-assembly 620, and adheres to the cap 604 via the cap adhesive 606. In the illustrated embodiment, the sensor sub-assembly 622 is connected to the attachment sub-assembly 620 via the interface with the cap adhesive 606, but does not contact the interior sidewalls of the deformable patient coupler 608. Accordingly, the attachment sub-assembly 620 is free to move with respect to the sensor sub-assembly 622 during attachment and operation of the sensor 600 to the patient, as the deformable patient coupler 608 stretches. In particular, referring to FIG. 6C, a user may position the acoustic coupler 616 against the patient's skin and press downwards on the attachment sub-assembly 620, towards the patient. The deformable patient coupler 608 stretches in response to the pressing force, allowing the attachment sub-assembly 620 to move downwards towards the patient until the adhesive 610 comes into contact with the patient's skin, thereby adhering the sensor 600 to the patient. Moreover, while the sensor 600 is attached to the patient, the resilience of the deformable patient coupler 608 causes the deformable patient coupler 608 to exert a downward force (toward the patient) onto the top side of the sensor sub-assembly 622 via the cap 604, providing a secure attachment. The sensor sub-assembly 622, including the acoustic coupler 616, may be thereby pressed against the patient so as to allow improved coupling of the sensor sub-assembly 622 to the patient's skin. This improved coupling or increased tightness between the sensor 600 and the patient's skin can result in better acoustic coupling of the sensor 600 with the skin and therefore stronger acoustic signal pickup by the sensor 600. As a result, in certain embodiments, the sensor 600 may have an improved SNR over other acoustic sensors.

As mentioned above, in an embodiment, the frame 628 includes four locking posts 625, for example, near each of the frame's 624 four corners. The locking posts 625 are generally cylindrical in shape, although in other embodiments they are tapered, conical, or frustoconical in shape. The locking posts 625 may provide alignment and mating for corresponding guide holes (not shown) on the acoustic coupler 616 and the cap 604. In some embodiments, the outside diameter of the locking posts 625 are smaller than the inside diameter of the guide holes such that the guide holes do not contact the alignment pins when inserted. In other embodiments, the guide holes (of the acoustic coupler 616 and the cap 604) form a press-fit connection with the locking posts 625 of the frame 624. In other embodiments, the frame 624 includes one, two, three, or more locking posts 625.

In an embodiment, the locking posts 625 are formed from the same material as, and are integral with the frame 624. When the locking posts 625 are brought into contact with horns of an ultrasonic welder, they liquefy and flow to form a mushroom-shaped weld over the material directly beneath it. When the components of the sensor 600 are in place, the locking posts 625 may be flowed to lock all components into a fixed position. In other embodiments, the locking posts 625 are not formed from the same material as the frame 624. For example, in other embodiments, the locking posts 625 include clips, welds, adhesives, and/or other locks to hold the components of the sensor 600 in place when the locking posts 625 are locked into place.

In another embodiment, the attachment sub-assembly 620 is joined to the sensor sub-assembly 622 with an adhesive, for example the cap adhesive 606. In this embodiment, the cap adhesive 606 may serve to join the cap 604 to each of the deformable patient coupler 608 and the sensor sub-assembly 622. In this embodiment, the locking posts 625 may not extend to attach the attachment sub-assembly 620 to the sensor sub-assembly 622, but the attachment sub-assembly 620 may be attached to the sensor sub-assembly 622 solely by the adhesive.

As shown in FIG. 6D-6E, the acoustic coupler 616 may include a shell 616 that houses the frame 624, and which can support various components of the sensor 600 in an assembled state, including the PCB 626, and the stacked sensing elements (not shown).

As shown in FIG. 6D, the PCB 626 may include various sensor cable-to-PCB connections 627. Accordingly, the sensor cable 614 may include one or more electrically conductive wires (not shown) that may be electrically coupled to the PCB 626 to provide signals indicative of sensed acoustic information to, for example, a patient monitor.

Figure 6F:
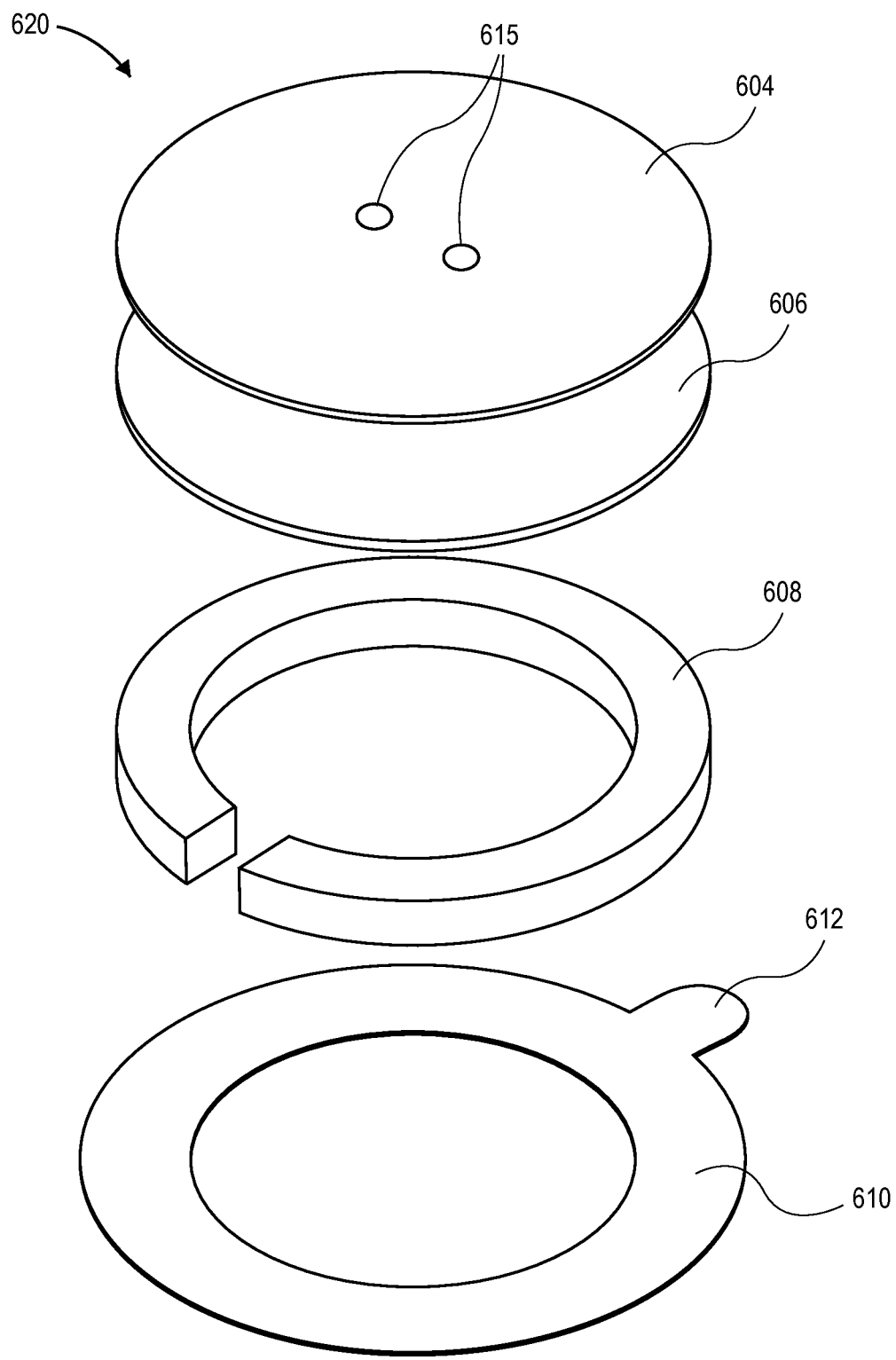
FIG. 6F is a top exploded, perspective view of an attachment sub-assembly of the sensor of FIGS. 6A-6B, in accordance with an embodiment described herein.

FIG. 6F is a top exploded, perspective view of the example attachment sub-assembly 620 of the sensor 600. As shown, and as previously described, the attachment sub-assembly 620 can include the cap 604, the cap adhesive 606, the deformable patient coupler 608, and the adhesive portion 610. The adhesive portion 610 can attach the sensor 600 to a skin surface of a patient. In an embodiment, the adhesive portion 610 includes a pull tab, such as the pull tab 612 having a generally arc-shape to facilitate removal of the sensor 600 from a patient. In various embodiments, the pull tab 612 may have any other suitable shape, and/or other components of the attachment sub-assembly 620 may include a pull tab. The pull tab 612 may be omitted in other embodiments.

Some or all of the components of the attachment sub-assembly 620 are generally coupled together using, for example, a suitable adhesive (as described below). For example, cap adhesive 606 may be used to couple the cap 604 to the deformable patient coupler 608. The cap adhesive 606 may also, in an embodiment, couple the attachment sub-assembly 620 to the sensor sub-assembly 622, as previously described. In an embodiment, the cap adhesive 606 has a generally annular shape, similar to the shape of the deformable patient coupler 608, so as to attach the cap 604 to the deformable patient coupler 608. A similar adhesive layer may be used to couple deformable patient coupler 608 to the adhesive portion 610.

In an embodiment, the cap 604 is substantially rigid (and/or not easily deformable), while the deformable patient coupler 608 is substantially deformable (or more deformable than the cap 604). For example, in an embodiment the cap 604 may be made of a substantially rigid plastic material, while that deformable patient coupler 608 may be made of a deformable plastic, rubber, and/or foam or foam-like material.

As mentioned above, and as further described below, the cap 604 and the cap adhesive 606 may include one or more pressure equalization pathways 615. In an embodiment, the pressure equalization pathways 615 may be placed in generally symmetric positions on the cap 604. However, the pressure equalization pathways are optional in other embodiments.

Figure 6G:
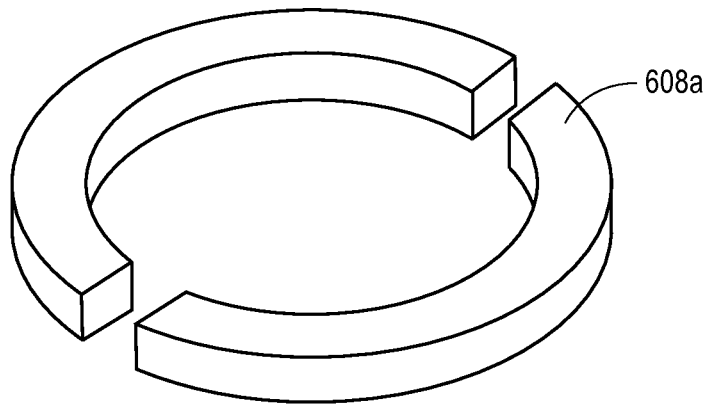
FIG. 6G shows perspective views of various embodiments of a component of the attachment sub-assembly of FIG. 6F.
Figure 6G:
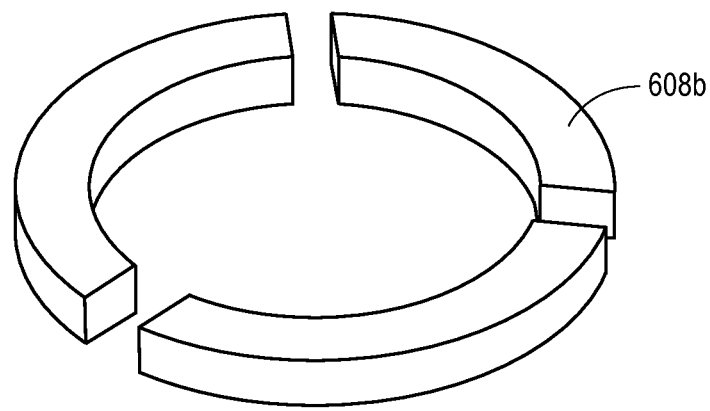
Figure 6G:
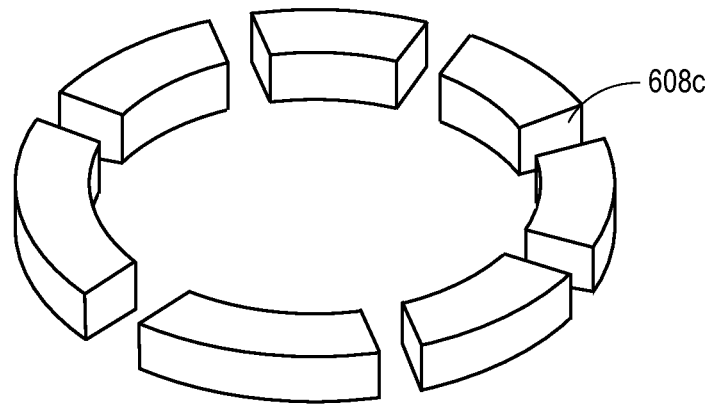

The deformable patient coupler 608 may, in an embodiment, comprise a complete annulus. In another embodiment, the deformable patient coupler 608 may include an opening, such as the opening shown in FIG. 6F, to allow, for example, connection of the sensor cable 614 to the sensor sub-assembly 622. As shown in FIG. 6G, the deformable patient coupler 608 may include any other number of openings, as shown by example deformable patient couplers 608a-608c. The openings in the example deformable patient couplers 608a-608c may facilitate, for example, ease of construction of the sensor 600, improved acoustic characteristics of the sensor 600, and/or improved coupling and/or attachment of the sensor 600 to the patient.

Figure 6H:
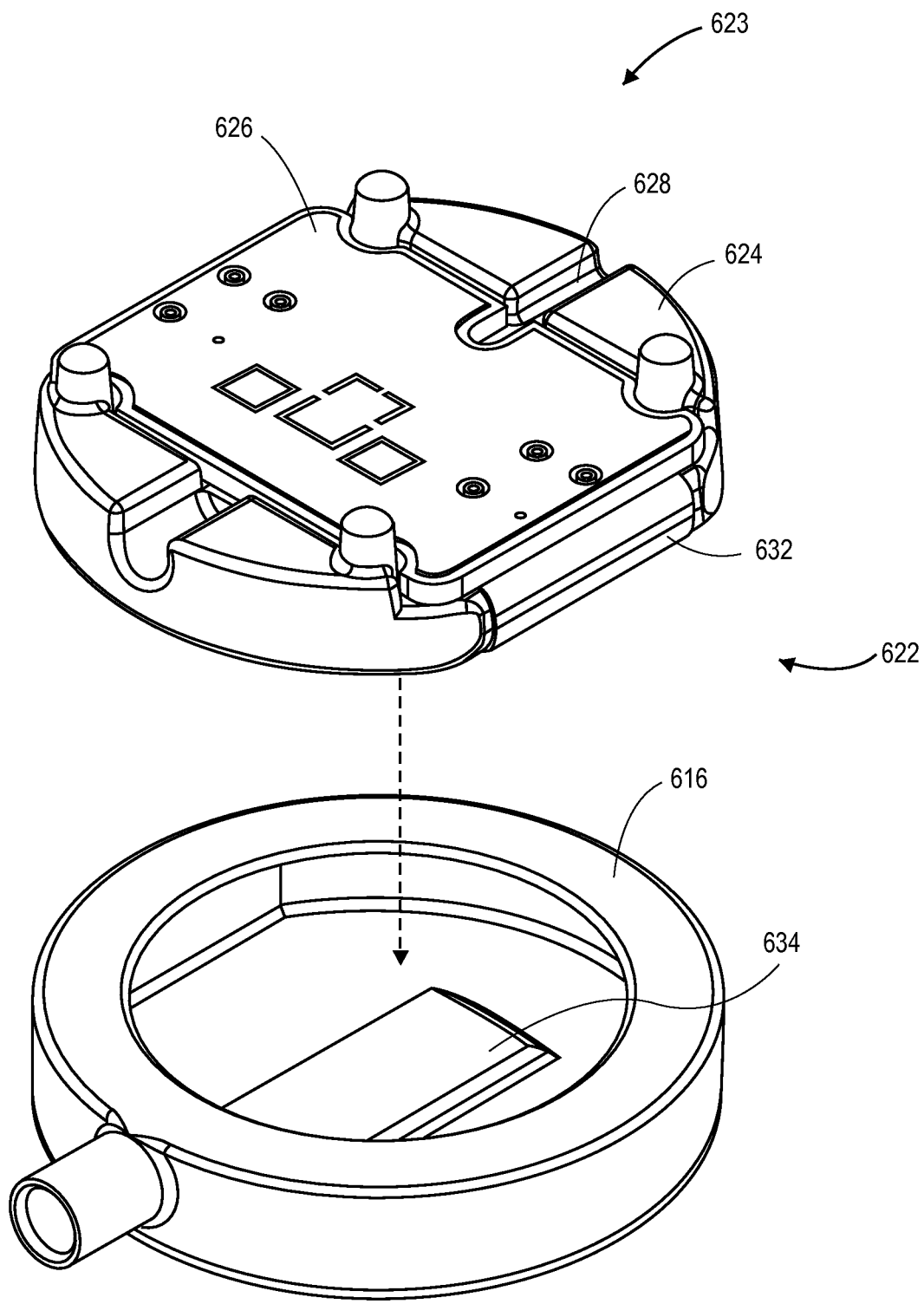
FIGS. 6H-6I are top and bottom partially-exploded, perspective views, respectively, of a sensor sub-assembly and coupler of the sensor of FIGS. 6A-6B, in accordance with embodiments described herein.
Figure 6I:
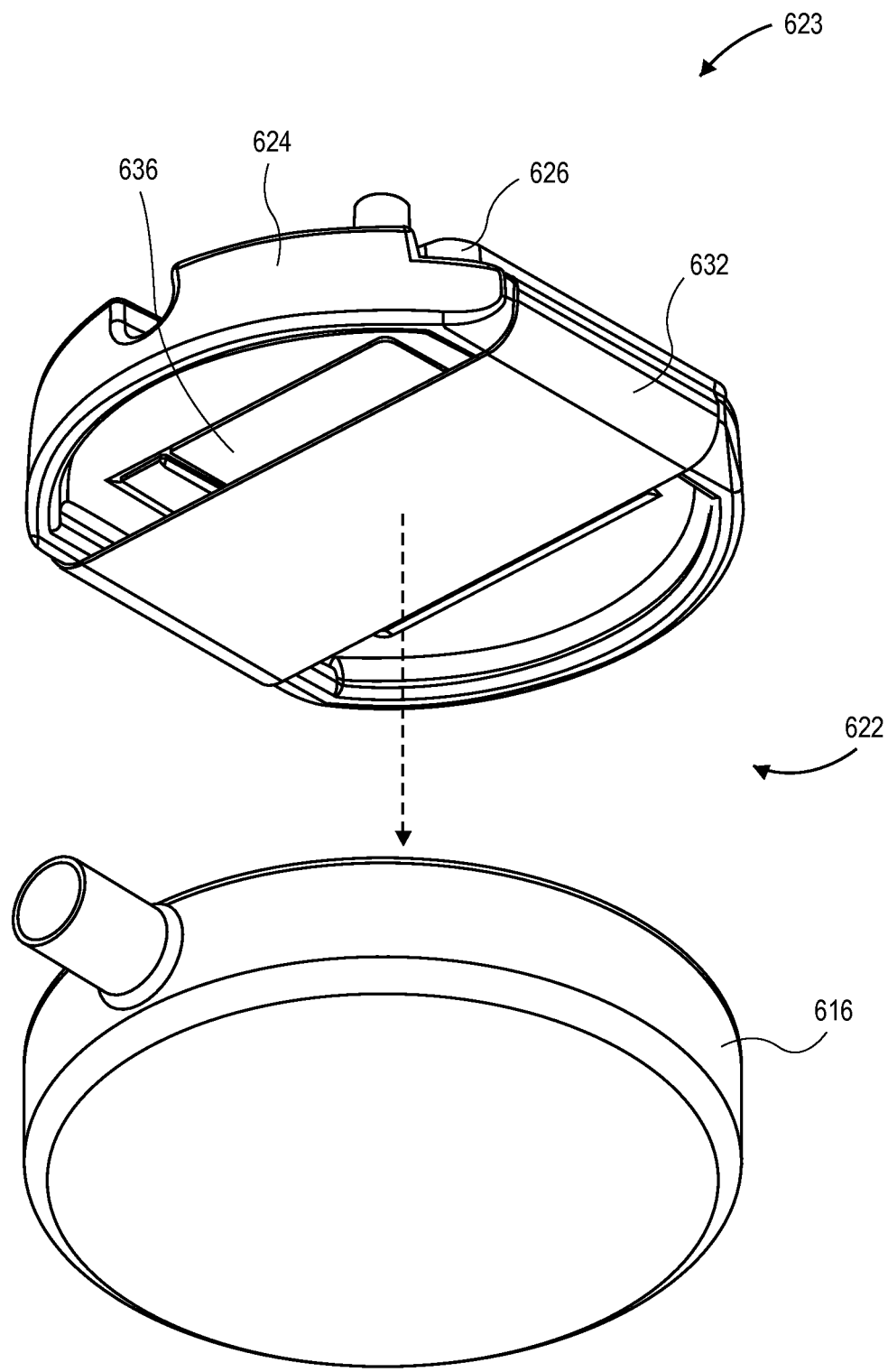

FIGS. 6H-6I are top and bottom partially-exploded, perspective views, respectively, of the sensor sub-assembly 622, according to embodiments of the present disclosure. The sensor sub-assembly 622 includes a frame sub-assembly 623 and the acoustic coupler 616. As mentioned above, the acoustic coupler 616 is generally comprised of a shell 616 that houses the frame sub-assembly 623, and which is generally configured to support various components of the frame sub-assembly 623 in an assembled state, including the PCB 626, the frame 624, and the stacked sensing elements 632. In an embodiment, the stacked sensing elements 632 are piezoelectric films (as illustrated), although other types of sensing elements can be used.

The components of the sensor sub-assembly 622 can be assembled similarly to the sensor 415 of FIG. 4A. For example, the stacked sensing elements 632 may be wrapped around a portion of the frame 624 and extend across an acoustic cavity 636 (FIG. 6I) of the frame 624 in tension. As discussed with respect to FIG. 4A, the active portions of the stacked sensing elements 632 that extend across the acoustic cavity 636 may be free to move in response to received vibrations, enabling detection of a physiological signal when the sensor 600 is attached to the patient. In certain embodiments, the acoustic cavity 636 or a portion thereof extends all the way through the frame 624. For example, the cavity may form one or more holes in the interior portion of the frame 624.

In the depicted embodiment, the PCB 626 is positioned on an upper side of the frame 624 such that the underside of the PCB 626 comes into contact with portions of the stacked sensing elements 632 that are wrapped around the frame 624. In an embodiment, the sensor cable 614 is electrically coupled to the sensor sub-assembly 622 via the PCB 626 (as mentioned above, by contact with the sensor cable-to-PCB connections 627). Through this contact, electrical signals may be communicated from the sensor 600 to the physiological monitor through the sensor cable 614.

The acoustic coupler 616 (also referred to as a coupler shell, coupler, and/or shell) can transmit vibrations received from the patient to stacked sensing elements 632. As described above, the acoustic coupler 616 may include a spherical cap portion configured to press against the patient's body when the acoustic sensor 600 is fastened into place on the patient. The spherical cap portion of the acoustic coupler 616 can come into contact with the patient to couple acoustic signals from the patient to the stacked sensing elements 632 of the sensor 600. Additionally, as shown in FIG. 6H, the acoustic coupler 616 may include a protrusion 634 designed to abut against the stacked sensing elements 632 and to bias them in tension across the acoustic cavity 636.

The coupler shell 616 may, in various embodiments, include any of many other shapes that are configured to couple acoustic signals from the patient to the stacked sensing elements 632. For example, the spherical cap portion of the acoustic coupler 616 may be more or less spherical than in shown in FIGS. 6A-6M. For example, the portion of acoustic coupler 616 that protrudes from the bottom portions of the sensor 600 may protrude further and/or less far from the sensor 600. In an embodiment, the protrusion 634 may have an at least partially flat surface that comes into contact with the stacked sensing elements 632. In various other embodiments, the protrusion 634 may have a generally curved or pointed surface that comes into contact with the stacked sensing elements 632.

In various embodiments, the stacked sensing elements 632 are configured to detect bodily sounds from a patient measurement site. The stacked sensing elements 632 may include piezoelectric membranes, for example, and are supported by the frame 624. The piezoelectric membranes are configured to move on the frame in response to acoustic vibrations, thereby generating electrical signals indicative of the bodily sounds of the patient, including respiration sounds, speech, heart sounds, wheezing, and so on (additional examples of which are described elsewhere herein).

Figure 6K:
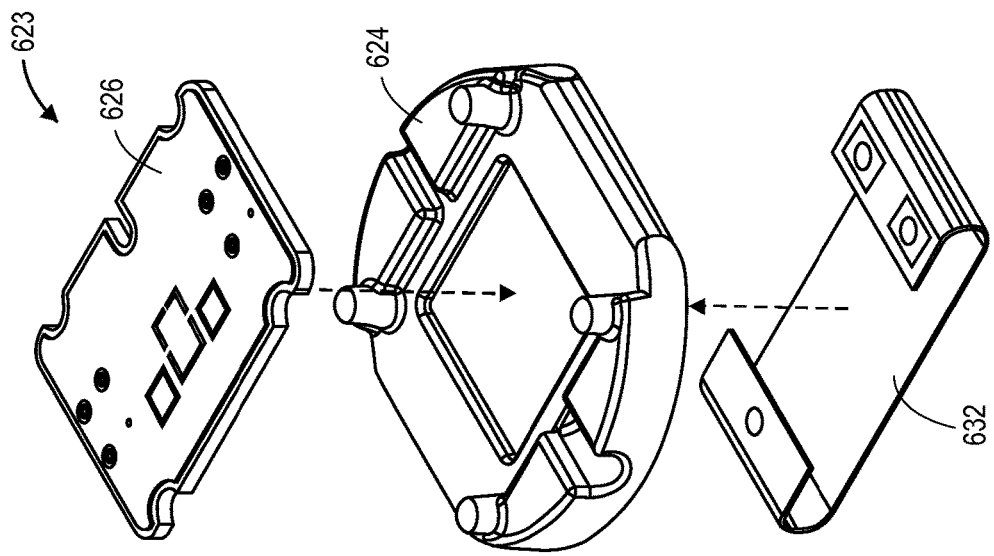
FIGS. 6J-6K are top and bottom exploded, perspective views, respectively, of a sensor sub-assembly of the sensor of FIGS. 6A-6B, in accordance with embodiments described herein.
Figure 6J:
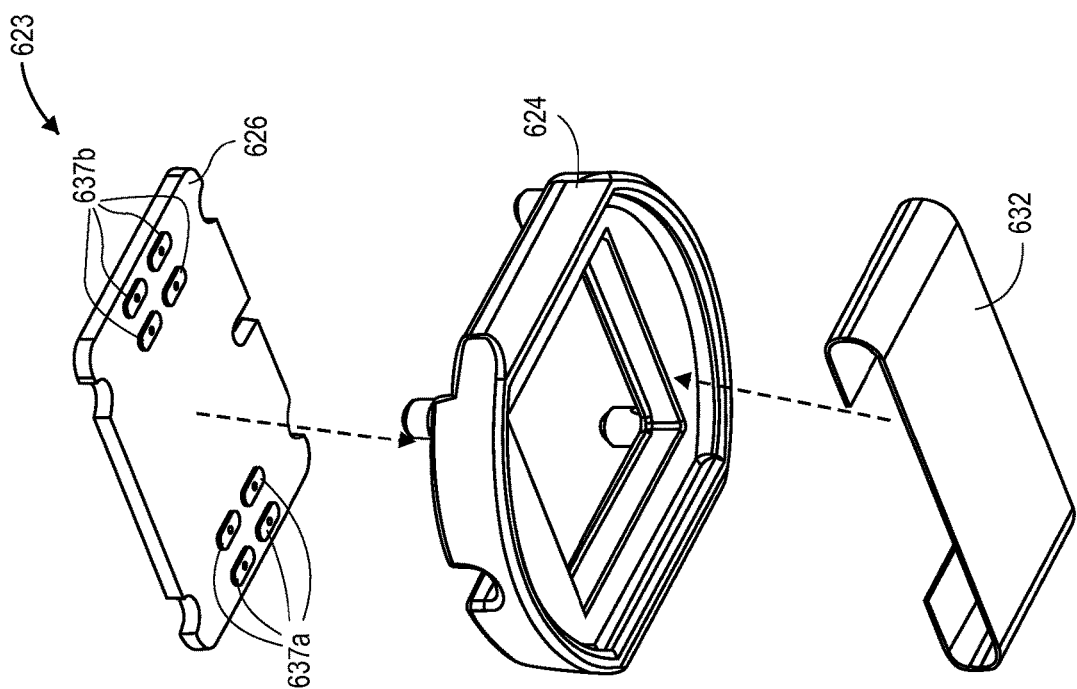

FIGS. 6J-6K are top and bottom exploded, perspective views, respectively, of the frame sub-assembly 623, in accordance with embodiments described herein. As shown, the underside of the PCB 626 can include one or more contacts 637a, 637b that may come into contact with one or more contacts on sides of the stacked sensing elements 632. The stacked sensing elements 632 can be any of those described herein. In the illustrated embodiment, for example, the stacked sensing elements 632 are the piezoelectric films described in FIGS. 5A-5E having flooded electrode surfaces, respectively, which form the outer surfaces of the piezoelectric stack. Moreover, the stacked sensing elements 632 include one or more vias or through holes extending an electrode from surfaces of the films to corresponding regions on the opposing surfaces of the respective films. As discussed above, this configuration enables coupling of the four electrodes (e.g., the anode and cathode for each film) to the appropriate contacts on the underside of the PCB 626.

For example, in one embodiment, the region 521b (FIG. 5D) of the flooded cathode coating on the outer surface of the second film 521 touches one or more of the contacts 637a, 637b on the underside of the PCB 626. Meanwhile, the through-holed regions 521a, 520b (FIG. 5D) of the outer surface of the second film 521 may touch one or more of the contacts 637a, 637b on the underside of the PCB 626.

According to the above-described connection scheme, the stacked sensing elements 632 can be coupled to circuitry (not shown) residing on and/or in the PCB 626 or other system component (e.g., the hub or monitor) to provide improved SNR and/or electrical shielding. For example, the electrodes of the stacked sensing elements 632 can each be coupled to an input of an attenuation circuit (e.g., a differential amplifier) or ground (or other common potential) in the manner illustrated schematically with respect to FIG. 3B above. Specifically, although other connections schemes are possible, in one embodiment, the contacts 637a on the PCB 626 couple the flooded, outer cathode of the second, exterior film 521 to ground, and the contacts 637b couple the inner, un-flooded anode of the second, exterior film 521, and the inner, un-flooded cathode of the first, interior film 520, to a first (e.g., positive) and second (e.g., negative) terminals, respectively, of a difference amplifier or other noise attenuation circuit.

In an embodiment, the PCB 626 and the frame 624 effectively sandwich the portion of the stacked sensing elements 632 wrapped around the frame 624 so as to provide a secure electrical connection with the contacts 637a, 637b and to protect the contact between the stacked sensing elements 632 and the contacts 637a, 637b, e.g., from shorts due to contact with moisture. Accordingly, in an embodiment the top side of the PCB 626 and associated electrical components (e.g., electronic components, electrical leads, and/or electrical contacts) disposed thereon may be isolated from the cavity 636. For example, the coupling of the PCB 626 to the frame 624, and insertion of the frame subassembly 623 into the acoustic coupler 616, may create a barrier between the cavity 636 and the top side of the PCB 626. In an embodiment, components of the sensor 600 additionally provide a barrier between the top side of the PCB 626 and any ambient air (as provided, for example, by one or more pressure equalization pathways between the cavity 636 and ambient air. Isolation of the top side of the PCB 626 may prevent exposure of any electronics and/or electrical contacts of the sensor 600 to, for example, moisture from the patient to which the sensor 600 is attached. Accordingly, the electronics and/or electrical contacts of the sensor 600 may be protected from deterioration and/or various harmful effects.

Figure 6L:
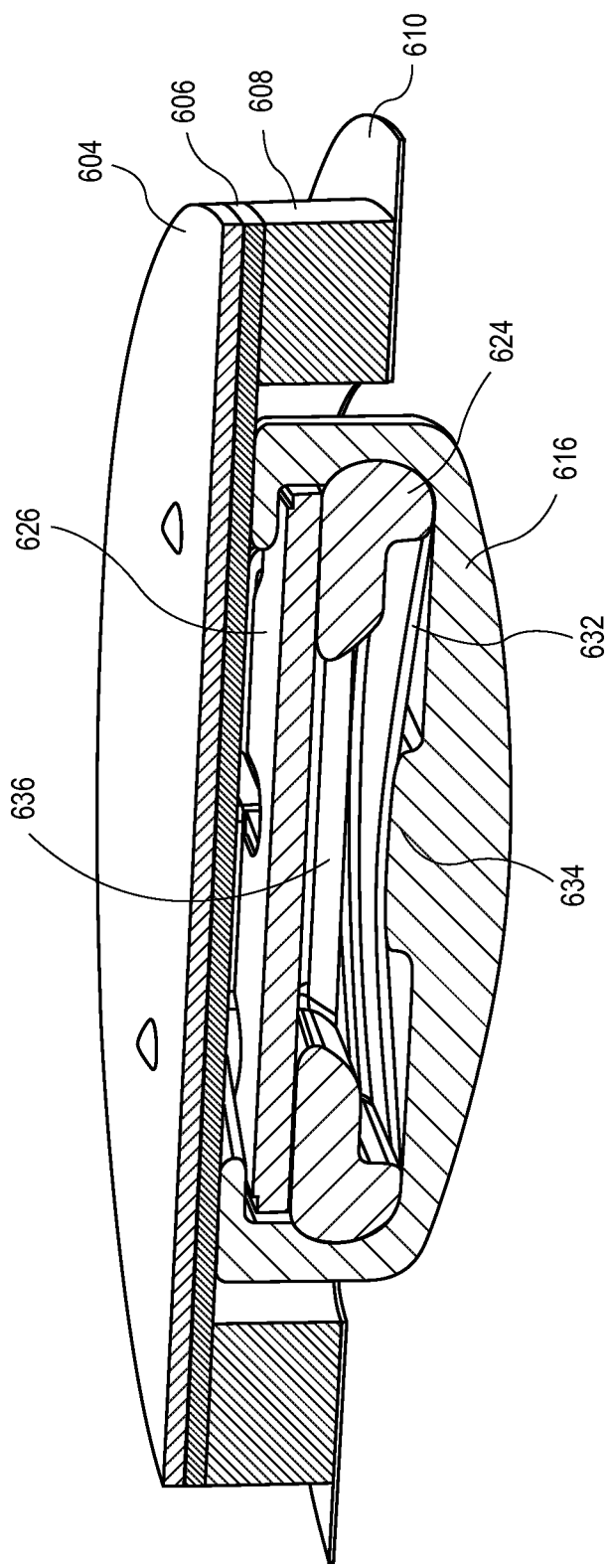
FIG. 6L shows a cross-sectional view of the sensor of FIGS. 6A-6B, in accordance with an embodiment described herein.

FIG. 6L shows a cross-sectional view of the sensor 600, in accordance with various embodiments described above with respect to FIGS. 6A-6K above.

Figure 6M:
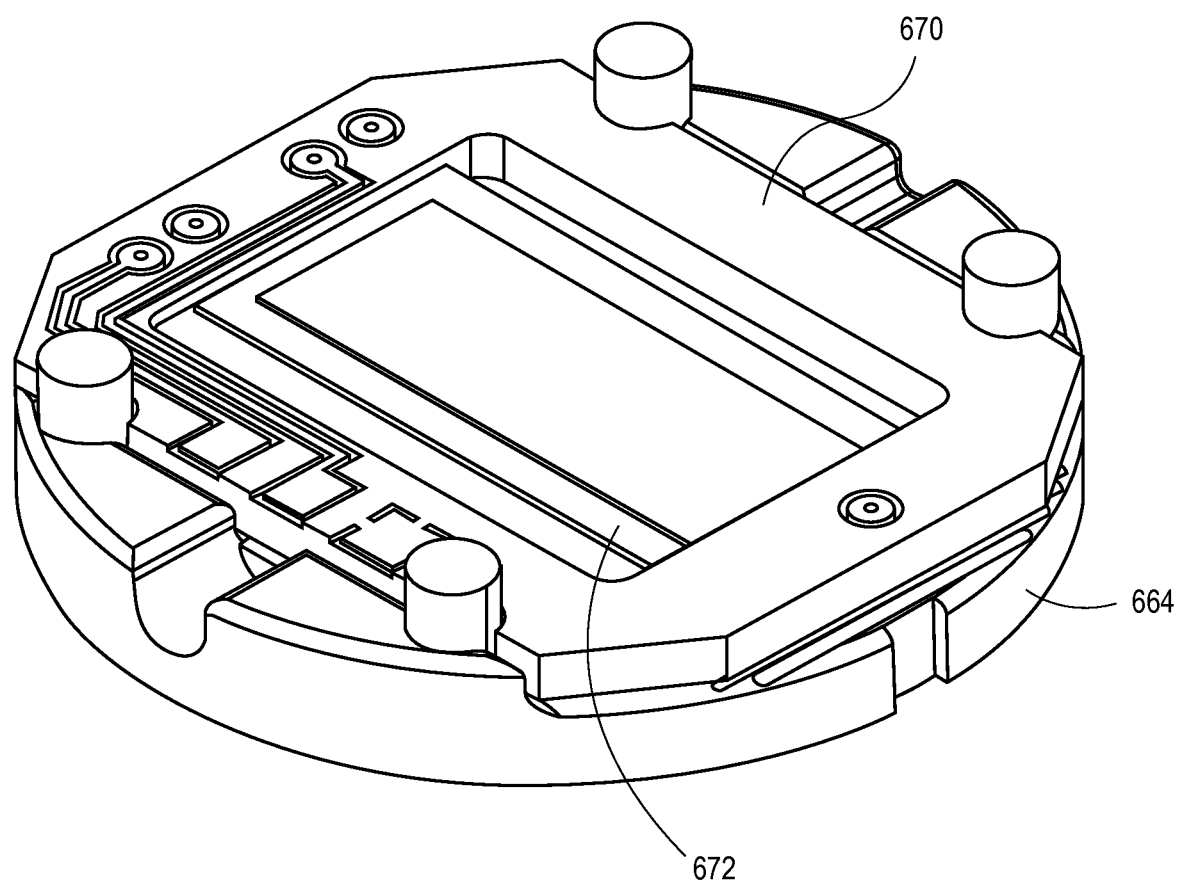
FIG. 6M shows a perspective view of another embodiment of a sensor incorporating multiple sensing elements in accordance with an embodiment described herein.

FIG. 6M shows a perspective view of another embodiment of the sensor 600 incorporating multiple sensing elements in accordance with an embodiment described herein. As described above, the embodiment of the sensor 600 shown in FIG. 6M includes a PCB 670 (similar to the PCB 626), a frame 664 (similar to the frame 624), and stacked sensing elements 672 (similar to stacked sensing elements 632). As shown in FIG. 6M, the stacked sensing elements 672 are generally sandwiched between the PCB 670 and the frame 664. In an embodiment, contacts on the stacked sensing elements 672 may come in contact with contacts on the underside of the PCB 670. For example, the stacked sensing elements 672 may be similar to the stacked sensing elements 632 of the figures described above, however the stacked sensing elements 672 are not wrapped around the frame 664.

FIG. 10 is a top perspective view illustrating an embodiment of a sensor 1002 including an additional adhesive portion. As shown, the sensor 1002 (similar to the sensor 600 described in reference to FIGS. 6A-6M above) includes an adhesive portion 1004 (similar to the adhesive portion 610, the sensor 600) for attaching the sensor 1002 to the skin of a patient. The sensor 1002 additionally includes an extended adhesive portion 1006 and an optional pull tab 1008. In an embodiment, the extended adhesive portion 1006 may provide an additional adhesive area for attaching the sensor to the skin of the patient. The extended adhesive portion 1006 may, in an embodiment, provide better, more compliant, coupling of the sensor to the patient. For example, the coupling provided by the extended adhesive portion 1006 may enable the sensor 1002 to stay in place on the patient's skin even as the patient moves about. The better coupling enabled by the extended adhesive portion 1006 may, for example, improve SNR of the sensor 600. In an embodiment, the extended adhesive portion 1006 is transparent or semi-transparent. As a result, the adhesive 1004, 1006 and/or sensor 1002 may appear to be smaller than they actually are. In an embodiment, the extended adhesive portion 1006 (and/or adhesive portion 1004) includes perforations and/or holes (not shown) to provide airflow to the skin of the patient so as to increase patient comfort. The material and adhesive used for the extended adhesive portion 1006 may include any of the materials and adhesives discussed above and below with reference to the adhesive portion 610.

In various embodiments described above, providing attachment of the sensor to the patient completely, or substantially completely, around the perimeter of the sensor (as provided by, for example, the adhesive portion 610 and/or the extended adhesive portion 1006) enables improved coupling of the sensor to the patient. Improved coupling of the sensor to the patient may further enable other advantages, for example, improved SNR. Additionally, when the adhesive portion of the sensor extends around the perimeter of the sensor, coupling of the sensor to the patient with substantially even force across the entire sensor (or a large portion thereof) may be applied. For example, the design of the sensor may enable the acoustic coupler of the sensor to be pressed against the skin of the patient with roughly even force around and across the acoustic coupler. In an embodiment, a bandage or tape may be used in addition to, or in place of, the adhesive portion to attach the sensor to the measurement site of the patient. Moreover, such bandages or tapes may be a variety of different shapes including generally elongate, circular and oval, for example.

In various embodiments, and also as described above, the deformable patient coupler (for example, the deformable patient coupler 608) provides a compliant, deformable, layer that enables improved coupling and/or attaching of the sensor to the patient. The deformable patient coupler can further improve patient coupling and may provide other advantages, such as improved SNR. In various embodiments, and as with the adhesive portion described above, providing attachment of the sensor to the patient completely, or at least partially, around the perimeter of the sensor via the deformable patient coupler enables improved coupling of the sensor to the patient. This improved coupling may result due to the coupling of the sensor to the patient with substantially even force as described above. The combination of the deformable patient coupler and the adhesive portion enables the acoustic coupler of the sensor to be pressed against the skin of the patient with substantially equal force around and across the acoustic coupler.

In various embodiments, and as described above, a large acoustic coupler is provided that spans and/or extends across substantially the entire bottom portion of the sensor and/or the sensor sub-assembly. The large patient contact area provided by the large acoustic coupler provides, in various embodiments, improved SNR and/or coupling of acoustic signals from the patient to the sensor. Additionally, the semi-spherical and/or spherical cap shape of the acoustic coupler may provide an even, or semi-even, propagation distance between the skin of the patient and the sensor elements, providing further improved sensor performance.

In various embodiments, the design of the sensor described above (for example sensor 600) reduces the likelihood of the sensor from becoming de-coupled from the patient due to, for example, patient movement. For example, the adhesive portion that surrounds the perimeter or circumference of the sensor provides substantially even attachment force around and/or across the sensor. Additionally, the deformable patient coupler may provide for further constant and/or homogeneous pressure of the sensor to the skin of the patient even as the patient moves or flexes.

In various embodiments, design of the sensor (for example, sensor 600) advantageously enables the sensor to be compact. For example, the relatively small size of the frame and sensor sub-assembly can allow the sensor to be attached comfortably to contoured, generally curved portions of the patient's body. For, example, the sensor can be comfortably attached to portions of the patient's neck whereas a larger frame may be awkwardly situated on the patient's neck or other contoured portion of the patient. The size of the sensor may allow the sensor to be attached to the patient in a manner allowing for improved sensor operation. For example, the relatively small sensor sub-assembly, when combined with the relatively large acoustic coupler and the attachment sub-assembly, allows the sensor to be applied with substantially uniform pressure across the patient contact area.

Second Example Sensor

Figure 12A:
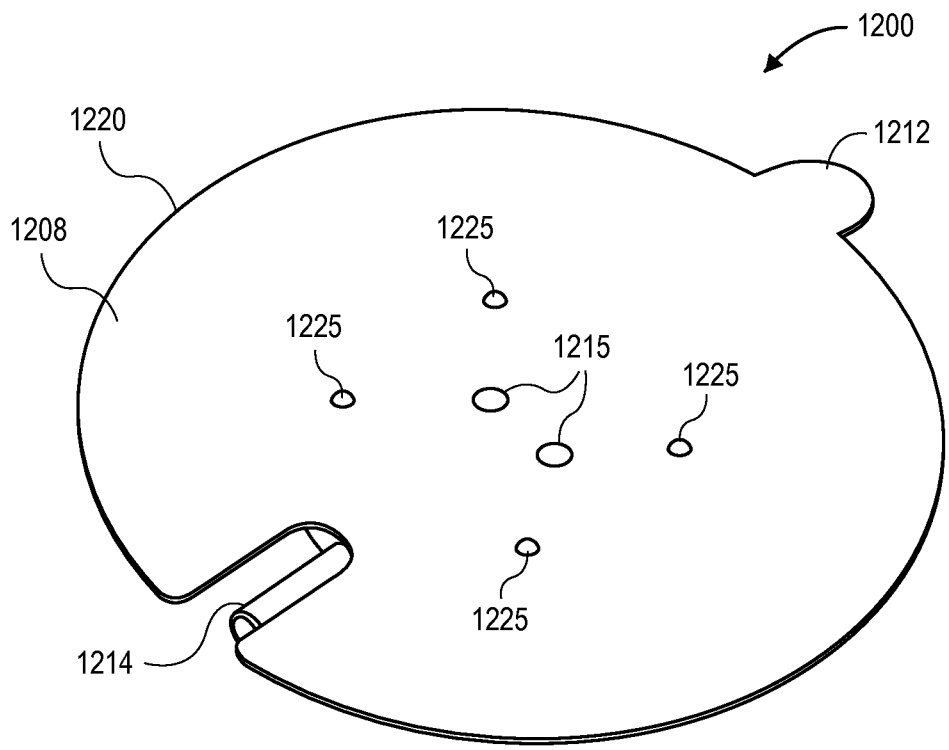
FIGS. 12A-12B are top and bottom views, respectively, of a sensor incorporating multiple sensing elements in accordance with embodiments described herein.
Figure 12B:
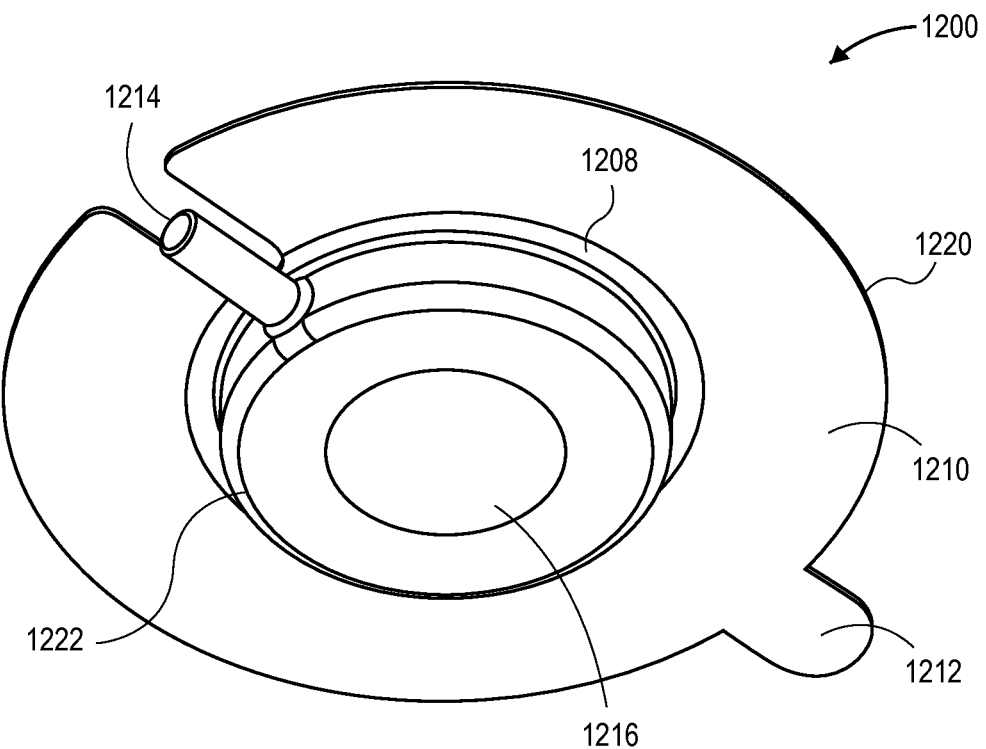

FIGS. 12A-12B are top and bottom views, respectively, of an embodiment of a sensor 1200, similar to the sensor 600 embodiment described above, that can detect acoustic physiological sounds from a patient and incorporating an attachment sub-assembly 1220, an acoustic coupler a including an at least partially spherical cap portion, multiple sensing elements, and certain other beneficial aspects described herein. For example, the sensor 1200 can provide improved SNR using the sensing elements according to techniques described above with respect to FIGS. 2A-4B. Moreover, the sensor 1200 can include a stacked, multiple sensing element configuration providing enhanced shielding, compatible with the techniques described above with respect to FIGS. 4A-5E. Additionally, as is described below in reference to FIGS. 12A-12L, the sensor 1200 can include an acoustic coupler 1216 with an at least partially spherical or rounded cap portion, and a deformable attachment sub-assembly 1220 that can provide enhanced patient and acoustic coupling that can provide improved SNR and coupling even when the patient moves, among other possible advantages. Although the cap portion of the coupler may be at least partially spherical or otherwise rounded (e.g., convex), for conciseness, the remainder of this specification shall refer to the cap portion as being a spherical cap portion.

The sensor 1200 is generally attachable to a patient and can be coupled to a patient monitor. For example, the sensor 1200 can be used with the system 10 of FIGS. 1A-1B. Additionally, the sensor 1200 may be compatible with the sensor system 100 of FIG. 10. For example, the sensor 1200 may be the sensor 101 of FIG. 10, and may be attached to the patient via an adhesive portion as described below. The sensor 1200 may also be referred to as an acoustic sensor.

As will be described in greater detail herein, in an embodiment, sensor 1200 includes one or more sensing elements, such as, for example, one or more piezoelectric devices or other acoustic sensing devices. The sensing elements generate voltages or currents that are responsive to vibrations generated by the patient, and the sensor 1200 includes circuitry to transmit the voltage generated by the sensing element to a processor for processing. In an embodiment, the sensor 1200 includes circuitry for detecting and transmitting information related to biological sounds to a physiological monitor. These biological sounds may include heart, breathing, and/or digestive system sounds, in addition to many other physiological phenomena. The sensor 1200 in certain embodiments is a biological sound sensor, such as the sensors described herein. In some embodiments, the biological sound sensor is one of the sensors such as those described in the '883 Application. In other embodiments, the sensor 1200 is a biological sound sensor such as those described in U.S. Pat. No. 6,661,161, which is incorporated by reference herein. Other embodiments include other suitable acoustic sensors Referring now specifically to the FIGS. 12A and 12B, the sensor 1200 fully assembled is shown, according to an embodiment. The sensor 1200 includes an attachment sub-assembly 1220 and a sensor sub-assembly 1222. The attachment sub-assembly 1220 includes a cap portion, or deformable patient coupler portion 1208 (generally referred to herein as the deformable patient coupler 1208 and/or the stretchable patient coupler 1208), and adhesive portion 1210. The deformable patient coupler 1208 further includes a pull tab 1212. In an embodiment, the deformable patient coupler 1208 may include pressure equalization pathways 1215. The sensor sub-assembly 1222 includes an acoustic coupler 1216 can include other components that are further described below. A sensor cable 1214 may be coupled to one or more components of the sensor 1200 and may, in an embodiment, attach to the sensor sub-assembly 1222 through an opening in the attachment sub-assembly 1220 as shown, and similarly as described above in reference to the embodiment of FIGS. 6A and 6B.

As shown, the sensor 1200 has a generally elliptical (for example, circular) cross-sectional profile, when viewed from a top of the sensor. As used herein, the term elliptical is used to also describe circular or generally circular. Further, each of the sensor sub-assembly 1222 and the attachment sub-assembly 1220 have generally elliptical (for example, circular) cross-sectional profiles, when viewed from a top of the respective sub-assemblies.

Figure 12C:
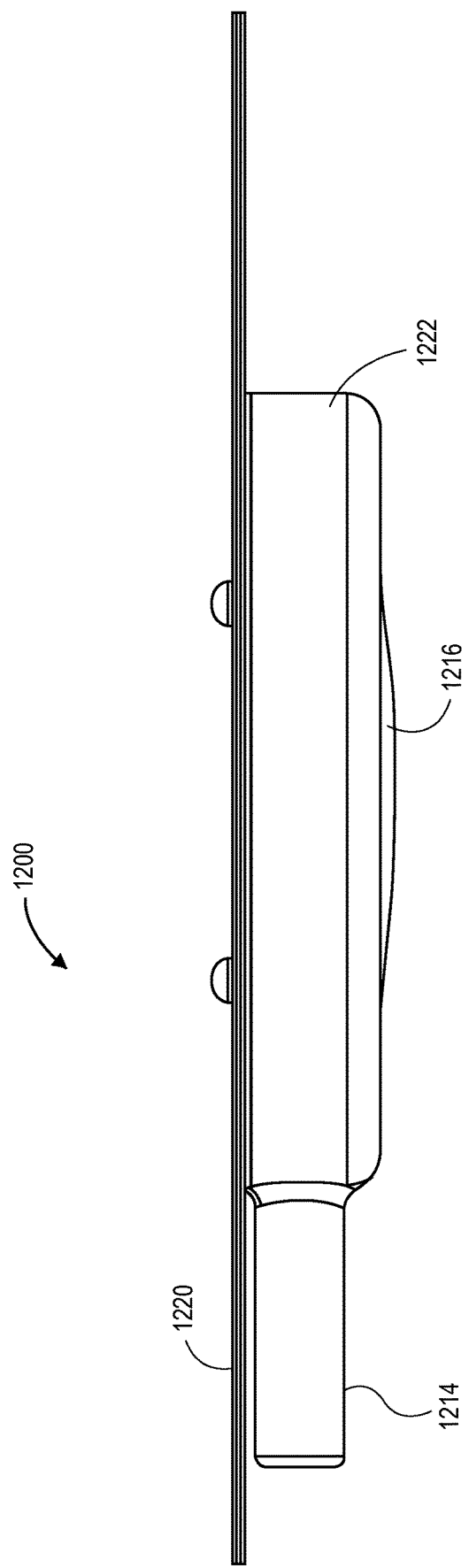
FIG. 12C shows a side view of the sensor of FIGS. 12A-12B.

FIG. 12C shows an example side view of the fully assembled sensor 1200 of FIGS. 12A and 12B. As shown, the spherical cap portion of the acoustic coupler 1216 of the sensor sub-assembly 1222 generally protrudes from a bottom side of the sensor 1200, and includes a spherical, semi-spherical, rounded, or otherwise convex shape (referred to hereinafter as semi-spherical for conciseness). The semi-spherical shape of the spherical cap portion of acoustic coupler 1216 may be referred to herein as a spherical cap or spherical cap portion. In general, and as is described in further detail below, when the sensor 1200 is applied to the patient, the adhesive portion 1210, via the deformable patient coupler 1208, attaches the sensor 1200 to the patient's skin and the acoustic coupler 1216 is at least partially compressed into the attachment sub-assembly 1220. The deformable patient coupler 1208 of the illustrated embodiment comprises a deformable, elastic, and/or foam or foam-like material that may stretch and deform so as to enable substantially even and constant coupling of the sensor 1200 to the patient. Additionally, the spherical cap portion of the acoustic coupler 1216 can advantageously enable improved coupling of acoustic signals from the patient to the sensor 1200.

Figure 12D:
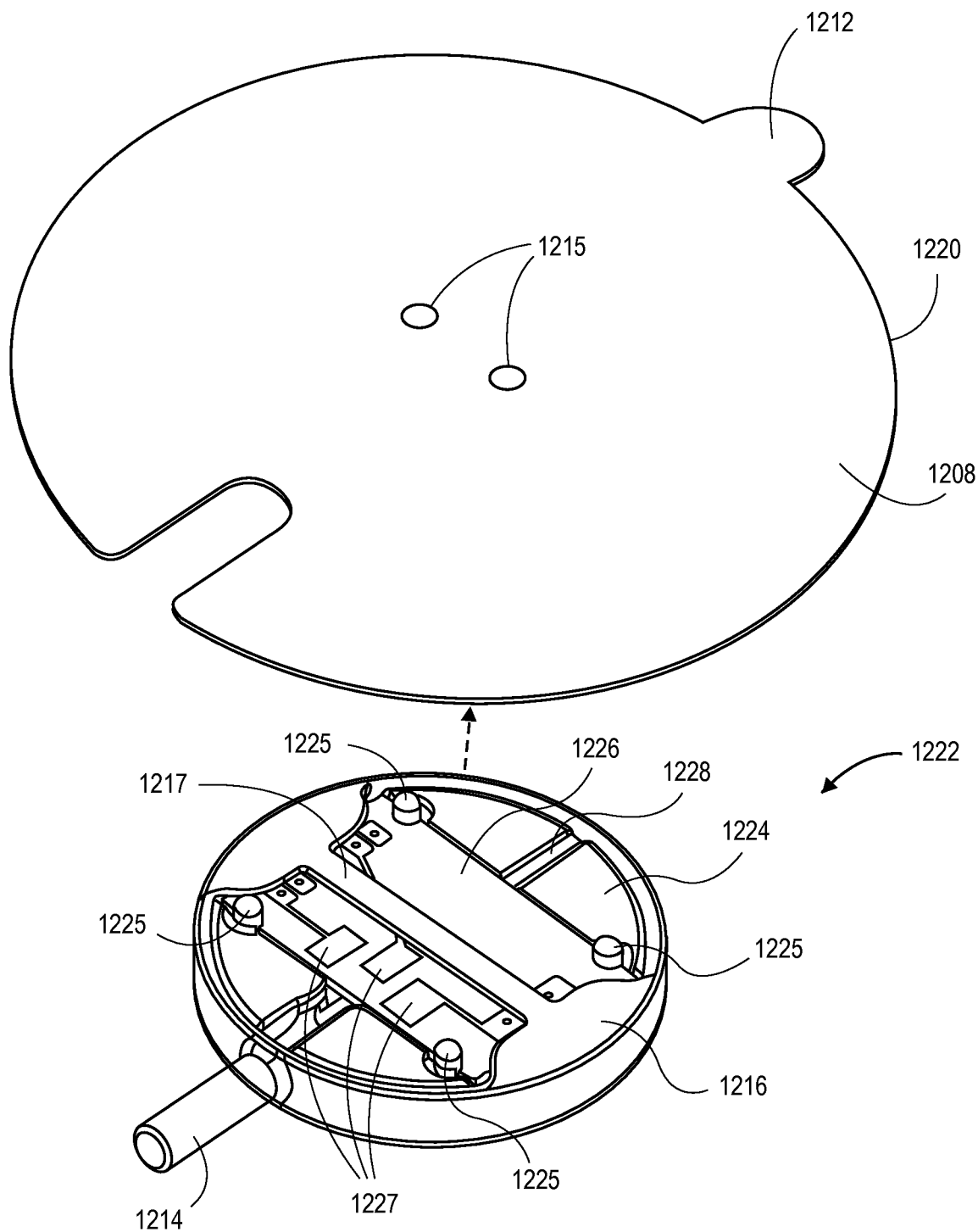
FIGS. 12D-12E are top and bottom partially-exploded, perspective views, respectively, of the sensor of FIGS. 12A-12B, in accordance with embodiments described herein.
Figure 12E:
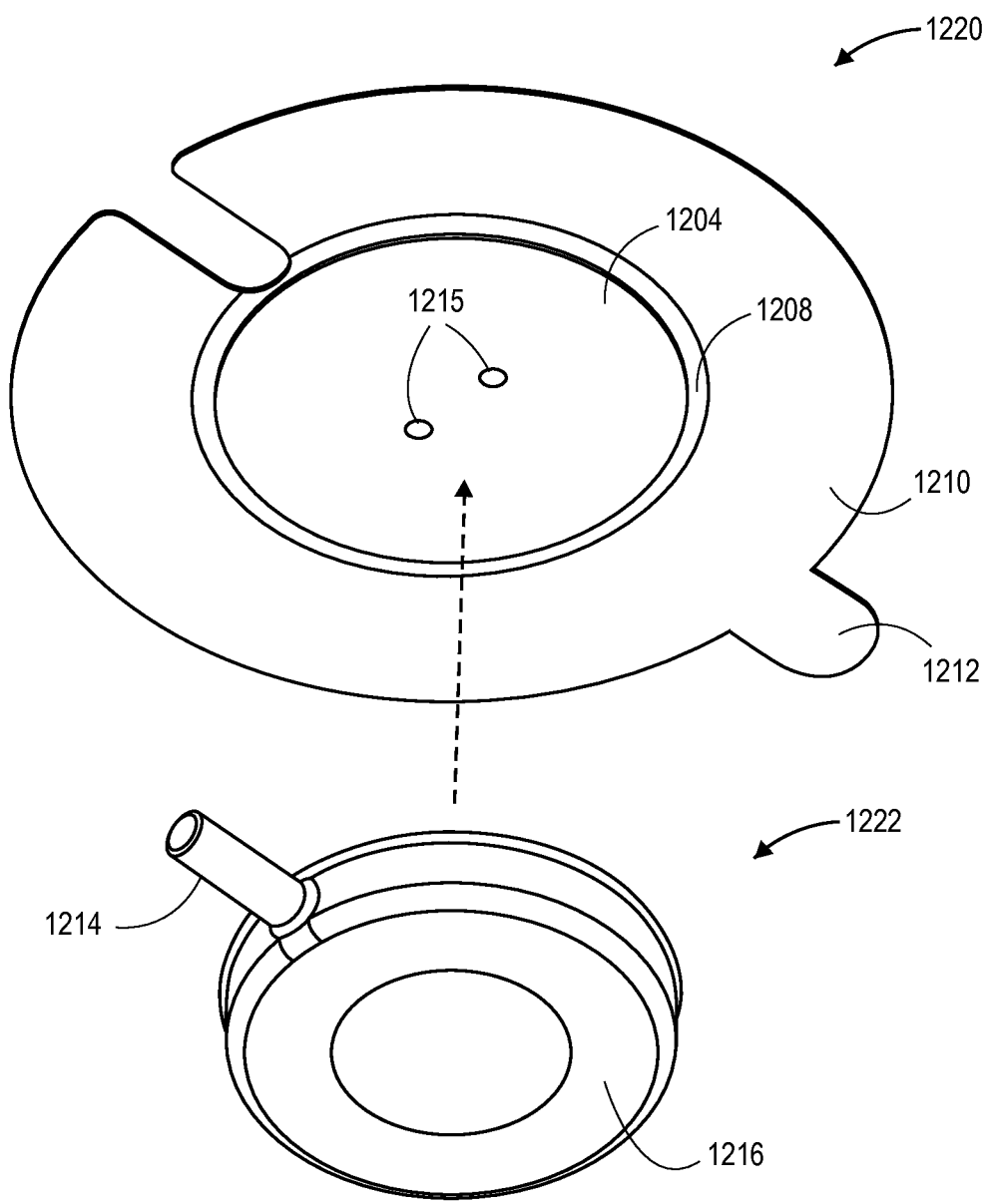

FIGS. 12D-12E show top and bottom partially-exploded, perspective views, respectively, of the sensor 1200, in accordance with an embodiment of the present disclosure. As shown, the sensor 1200 may be composed of two sub-components or sub-assemblies, the attachment sub-assembly 1220 and the sensor sub-assembly 1222. In FIGS. 12D-12E, each of the attachment sub-assembly 1220 and the sensor sub-assembly 1222 is shown in their individual, fully assembled states. The attachment sub-assembly 1220 includes each of the components mentioned above (including the deformable patient coupler 1208, adhesive portion 1210, optional pressure equalization pathways 1215, etc.) as well as a cap 1204. The sensor sub-assembly 1222 includes the acoustic coupler 1216, one or more locking posts 1225, a frame 1224, a printed circuit board (PCB) 1226, stacked sensing elements (not shown), and an optional pressure equalization pathway 1228 (among other components that are shown and described below).

Referring to FIG. 12E, as indicated by the dashed arrow, during assembly the sensor sub-assembly 1222 may attach to the attachment sub-assembly 1220 so that attachment sub-assembly 1220 is positioned on a top of the sensor sub-assembly 1222. As described below in reference to FIG. 12L, when the sensor 1200 is attached to a patient, the attachment sub-assembly 1220 may create a cavity defined by the underside of the of a cap adhesive 1206 (described below) and interior sidewalls comprising a stretched portion of the deformable patient coupler 1208. In the attached state, the sensor sub-assembly 1222 may be located within the cavity of the stretched deformable patient coupler 1208. Accordingly, in an attached state, the attachment sub-assembly 1220 at least partially surrounds, encompasses, encases, and/or forms a shell around and/or over the top and sides of the sensor sub-assembly 1222.

According to the illustrated embodiment, the top of the sensor sub-assembly 1222 contacts the cap 1204 of the attachment sub-assembly 1220, adheres to the cap 1204 via the cap adhesive 1206, and is positioned beneath the deformable patient coupler 1208 (as further described below in reference to FIG. 12F). Accordingly, the attachment sub-assembly 1220 is free to move with respect to the sensor sub-assembly 1222 during attachment and operation of the sensor 1200 to the patient, as the deformable patient coupler 1208 stretches. In particular, referring to FIG. 12C, a user may position the acoustic coupler 1216 against the patient's skin and press downwards on an outer circumference of the attachment sub-assembly 1220 towards the patient. The deformable patient coupler 1208 stretches in response to the pressing force, allowing the attachment sub-assembly 1220 to move downwards towards the patient until an adhesive 1210 (described below) comes into contact with the patient's skin, thereby adhering the sensor 1200 to the patient. Moreover, while the sensor 1200 is attached to the patient, the resilience of the deformable patient coupler 1208 causes the deformable patient coupler 1208 to exert a downward force (toward the patient) onto the top side of the sensor sub-assembly 1222 via the cap 1204, providing a secure attachment. The sensor sub-assembly 1222, including the acoustic coupler 1216, may be thereby pressed against the patient so as to allow improved coupling of the sensor sub-assembly 1222 to the patient's skin. This improved coupling or increased tightness between the sensor 1200 and the patient's skin can result in better acoustic coupling of the sensor 1200 with the skin and therefore stronger acoustic signal pickup by the sensor 1200. As a result, in certain embodiments, the sensor 1200 may have an improved SNR over other acoustic sensors.

As mentioned above, in an embodiment, the frame 1228 includes four locking posts 1225, for example, near each of the frame's 1224 four corners. The locking posts 1225 are generally cylindrical in shape, although in other embodiments they are tapered, conical, or frustoconical in shape. The locking posts 1225 may provide alignment and mating for corresponding guide holes (not shown) on the PCB 1226, the cap 1204 and the deformable patient coupler 1208. In some embodiments, the outside diameter of the locking posts 1225 are smaller than the inside diameter of the guide holes such that the guide holes do not contact the alignment pins when inserted. In other embodiments, the guide holes (of for example, the PCB 1226) form a press-fit connection with the locking posts 1225 of the frame 1224. In other embodiments, the frame 1224 includes one, two, three, or more locking posts 1225.

In an embodiment, the locking posts 1225 are formed from the same material as, and are integral with the frame 1224. When the locking posts 1225 are brought into contact with horns of an ultrasonic welder, they liquefy and flow to form a mushroom-shaped weld over the material directly beneath it. When the components of the sensor 1200 are in place, the locking posts 1225 may be flowed to lock all components into a fixed position. In other embodiments, the locking posts 1225 are not formed from the same material as the frame 1224. For example, in other embodiments, the locking posts 1225 include clips, welds, adhesives, and/or other locks to hold the components of the sensor 1200 in place when the locking posts 1225 are locked into place.

In another embodiment, the attachment sub-assembly 1220 is joined to the sensor sub-assembly 1222 with an adhesive, for example a cap adhesive 1206 (as further described below in reference to FIG. 12F). In this embodiment, the cap adhesive 1206 may serve to join the cap 1204 to each of the deformable patient coupler 1208 and the sensor sub-assembly 1222. In this embodiment, the locking posts 1225 may not extend to attach the attachment sub-assembly 1220 to the sensor sub-assembly 1222, but the attachment sub-assembly 1220 may be attached to the sensor sub-assembly 1222 solely by the adhesive.

As shown in FIG. 12D-12E, the acoustic coupler 1216 may include an integrally formed shell 1216 that houses the frame 1224, and which can support various components of the sensor 1200 in an assembled state, including the PCB 1226, and the stacked sensing elements (not shown). Further, the acoustic coupler/shell 1216 may include an integrally formed retaining portion 1217 that may retain the frame 1224 and PCB 1226 in the acoustic coupler/shell 1216.

As shown in FIG. 12D, the PCB 1226 may include various sensor cable-to-PCB connections 1227. Accordingly, the sensor cable 1214 may include one or more electrically conductive wires (not shown) that may be electrically coupled to the PCB 1226 to provide signals indicative of sensed acoustic information to, for example, a patient monitor.

Figure 12F:
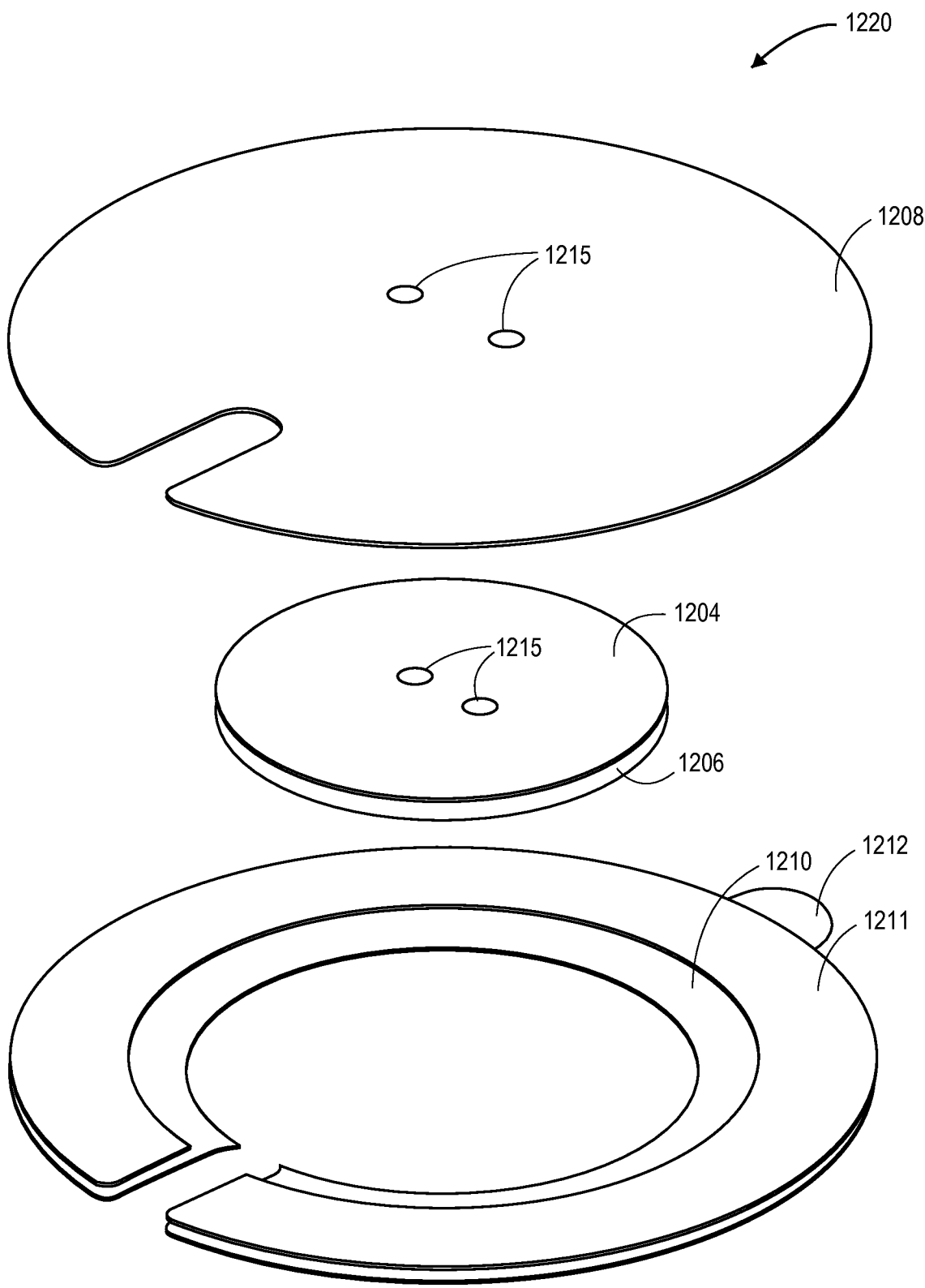
FIG. 12F is a top exploded, perspective view of an attachment sub-assembly of the sensor of FIGS. 12A-12B, in accordance with an embodiment described herein.

FIG. 12F is a top exploded, perspective view of the example attachment sub-assembly 1220 of the sensor 1200. As shown, and as previously described, the attachment sub-assembly 1220 can include the cap 1204, the cap adhesive 1206, the deformable patient coupler 1208, the adhesive portion 1210, and an adhesive attachment portion 1211. The adhesive portion 1210 can attach the sensor 1200 to a skin surface of a patient. In an embodiment, the adhesive portion 1210 includes a pull tab, such as the pull tab 1212 having a generally arc-shape to facilitate removal of the sensor 1200 from a patient. In various embodiments, the pull tab 1212 may have any other suitable shape, and/or other components of the attachment sub-assembly 1220 may include a pull tab. The pull tab 1212 may be omitted in other embodiments.

Some or all of the components of the attachment sub-assembly 1220 are generally coupled together using, for example, a suitable adhesive (as described below). For example, cap adhesive 1206 may be used to couple the cap 1204 to the sensor sub-assembly 1222, as previously described, while as similar adhesive layer may be used to couple the cap 1204 to the deformable patient coupler 1208. In an embodiment, the cap adhesive 1206 has a generally circular shape, similar to the shape of the cap 1204, so as to attach the cap 1204 to the sensor sub-assembly 1222. A similar adhesive attachment portion 1211 may be used to couple deformable patient coupler 1208 to the adhesive portion 1210. As shown, both the adhesive attachment portion 1211 and the adhesive portion 1210 may have a generally annular shape. However, in the embodiment shown the adhesive attachment portion 1211 has a width less than that of the adhesive portion 1210. Accordingly, a portion of the adhesive portion 1210 may be coupled to the deformable patient coupler 1208 (for example, a portion corresponding to the adhesive attachment portion 1211), while a portion of the adhesive portion 1210 may not be coupled to the deformable patient coupler 1208. As described below in reference to FIG. 12L, such an arrangement advantageously enables the deformable patient coupler 1208, when stretched to attach the sensor to the patient, to couple to the adhesive portion 1210 in a middle portion of the adhesive portion 1210. Coupling to the middle portion of the adhesive portion 1210 may advantageously provide a more secure coupling of the sensor to the patient as a side of the adhesive portion 1210 may not be easily pulled away from the skin of the patient.

In an embodiment, the cap 1204 is substantially rigid (and/or not easily deformable), while the deformable patient coupler 1208 is substantially deformable (or more deformable than the cap 1204). For example, in an embodiment the cap 1204 may be made of a substantially rigid plastic material, while that deformable patient coupler 1208 may be made of a deformable and/or stretchy plastic, rubber, and/or foam or foam-like material.

As mentioned above, and as further described below, the cap 1204, the cap adhesive 1206, and/or the deformable patient coupler 1208 may include one or more pressure equalization pathways 1215. In an embodiment, the pressure equalization pathways 1215 may be placed in generally symmetric positions on the cap 1204, the cap adhesive 1206, and/or the deformable patient coupler 1208. However, the pressure equalization pathways are optional in other embodiments.

The deformable patient coupler 1208 may, in an embodiment, comprise a complete disk and/or circle. In another embodiment, the deformable patient coupler 1208 may include an opening, such as the opening shown in FIG. 12F, to allow, for example, connection of the sensor cable 1214 to the sensor sub-assembly 1222.

Figure 12G:
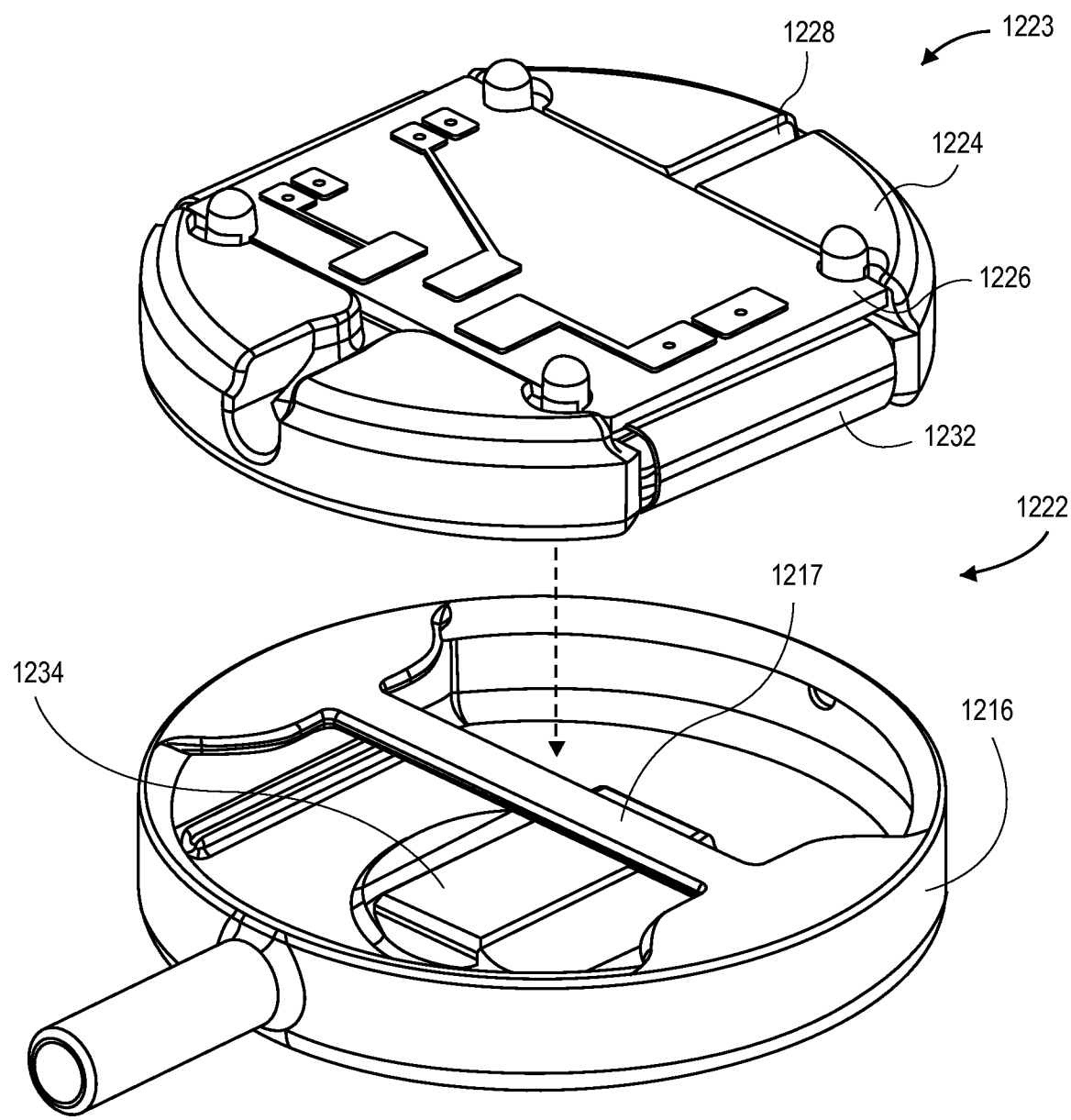
FIGS. 12G-12H are top and bottom partially-exploded, perspective views, respectively, of a sensor sub-assembly and coupler of the sensor of FIGS. 12A-12B, in accordance with embodiments described herein.
Figure 12H:
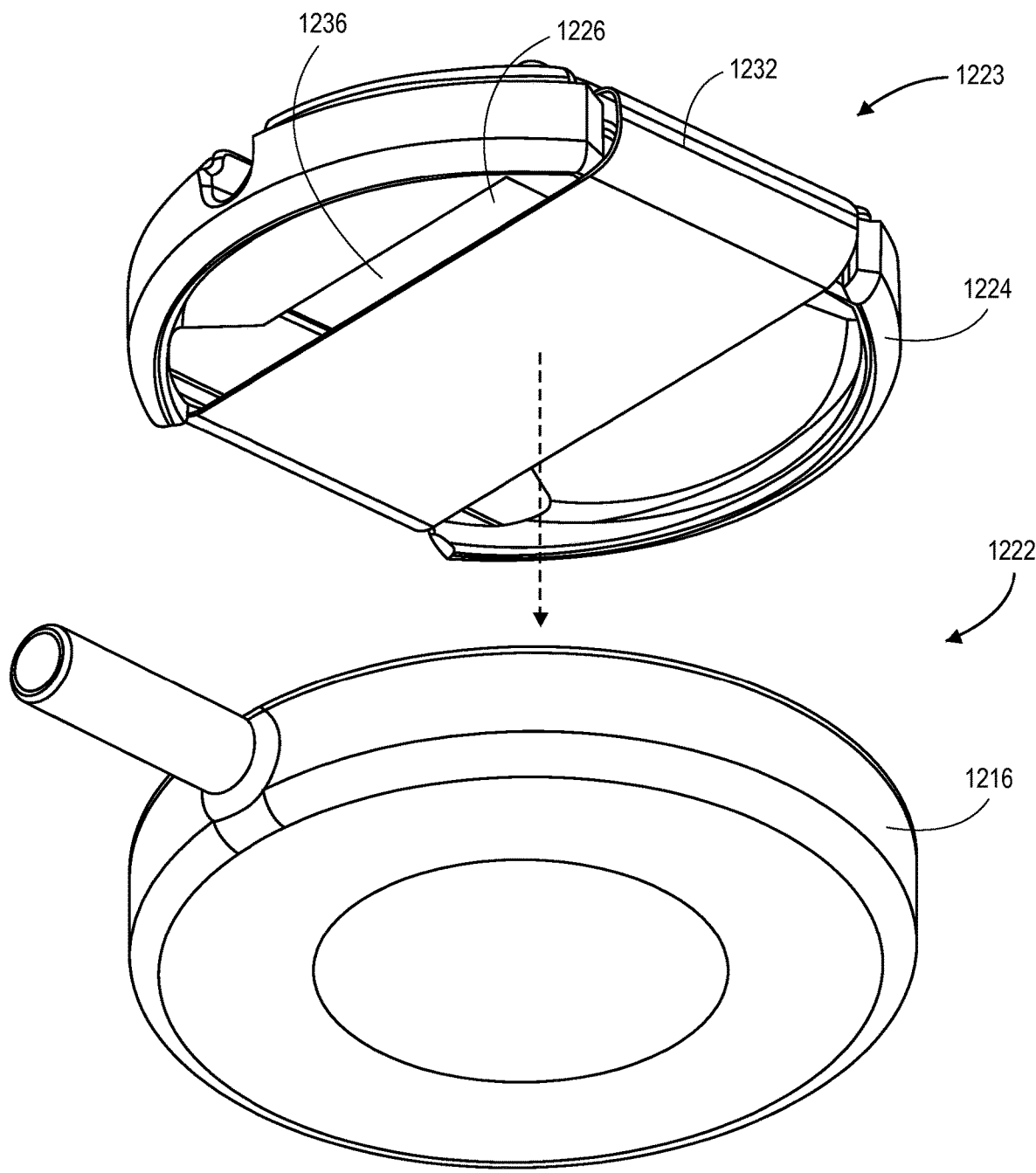

FIGS. 12G-12H are top and bottom partially-exploded, perspective views, respectively, of the sensor sub-assembly 1222, according to embodiments of the present disclosure. The sensor sub-assembly 1222 includes a frame sub-assembly 1223 and the acoustic coupler 1216. As mentioned above, the acoustic coupler 1216 is generally comprised of a shell 1216 that houses the frame sub-assembly 1223, and which is generally configured to support various components of the frame sub-assembly 1223 in an assembled state, including the PCB 1226, the frame 1224, and the stacked sensing elements 1232. In an embodiment, the stacked sensing elements 1232 are piezoelectric films (as illustrated), although other types of sensing elements can be used.

The components of the sensor sub-assembly 1222 can be assembled similarly to the sensor 415 of FIG. 4A. For example, the stacked sensing elements 1232 may be wrapped around a portion of the frame 1224 and extend across an acoustic cavity 1236 (FIG. 12H) of the frame 1224 in tension. As discussed with respect to FIG. 4A, the active portions of the stacked sensing elements 1232 that extend across the acoustic cavity 1236 may be free to move in response to received vibrations, enabling detection of a physiological signal when the sensor 1200 is attached to the patient. In certain embodiments, the acoustic cavity 1236 or a portion thereof extends all the way through the frame 1224. For example, the cavity may form one or more holes in the interior portion of the frame 1224.

In the depicted embodiment, the PCB 1226 is positioned on an upper side of the frame 1224 such that the underside of the PCB 1226 comes into contact with portions of the stacked sensing elements 1232 that are wrapped around the frame 1224. In an embodiment, the sensor cable 1214 is electrically coupled to the sensor sub-assembly 1222 via the PCB 1226 (as mentioned above, by contact with the sensor cable-to-PCB connections 1227). Through this contact, electrical signals may be communicated from the sensor 1200 to the physiological monitor through the sensor cable 1214.

The acoustic coupler 1216 (also referred to as a coupler shell, coupler, and/or shell) can transmit vibrations received from the patient to stacked sensing elements 1232. As shown, the acoustic coupler 1216 has a generally elliptical (for example, circular) cross-sectional profile, when viewed from a top of the coupler. In various embodiments the acoustic coupler 1216 may be shaped differently, for example, it may have an oval, rectangular, or other elliptical cross-sectional profile, when viewed from a top of the coupler. As described above, the acoustic coupler 1216 may include a spherical cap portion configured to press against the patient's body when the acoustic sensor 1200 is fastened into place on the patient. The spherical cap portion of the acoustic coupler 1216 can come into contact with the patient to couple acoustic signals from the patient to the stacked sensing elements 1232 of the sensor 1200. Additionally, as shown in FIG. 12G, the acoustic coupler 1216 may include a protrusion 1234 designed to abut against the stacked sensing elements 1232 and to bias them in tension across the acoustic cavity 1236.

The coupler shell 1216 may, in various embodiments, include any of many other shapes that are configured to couple acoustic signals from the patient to the stacked sensing elements 1232. For example, the spherical cap portion of the acoustic coupler 1216 may be more or less spherical than in shown in FIGS. 12A-12L. For example, the portion of acoustic coupler 1216 that protrudes from the bottom portions of the sensor 1200 may protrude further and/or less far from the sensor 1200, and/or may comprise a greater or smaller portion of the bottom of the acoustic coupler 1216. In an embodiment, the protrusion 1234 may have an at least partially flat surface that comes into contact with the stacked sensing elements 1232. In various other embodiments, the protrusion 1234 may have a generally curved or pointed surface that comes into contact with the stacked sensing elements 1232.

Additionally, as shown the acoustic coupler 1216 has a generally elliptical (for example, circular) cross-sectional profile, when viewed from a top of the coupler.

In various embodiments, the stacked sensing elements 1232 are configured to detect bodily sounds from a patient measurement site. The stacked sensing elements 1232 may include piezoelectric membranes, for example, and are supported by the frame 1224. The piezoelectric membranes are configured to move on the frame in response to acoustic vibrations, thereby generating electrical signals indicative of the bodily sounds of the patient, including respiration sounds, speech, heart sounds, wheezing, and so on (additional examples of which are described elsewhere herein).

As mentioned above, the acoustic coupler 1216 may include the integrally formed retaining portion 1217 that may retain the frame 1224 and PCB 1226 in the acoustic coupler/shell 1216. During assembly, for example, the frame sub-assembly 1223 may be inserted beneath the retaining portion 1217 and into the acoustic coupler/shell 1216.

Figure 12J:
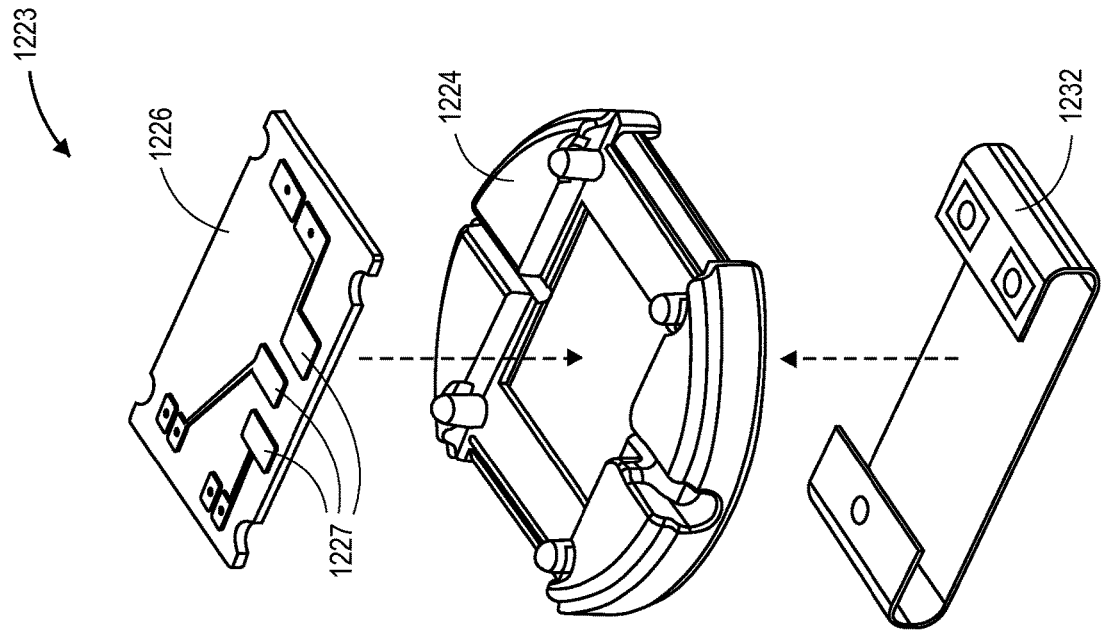
FIGS. 12I-12J are top and bottom exploded, perspective views, respectively, of a sensor sub-assembly of the sensor of FIGS. 12A-12B, in accordance with embodiments described herein.
Figure 12I:
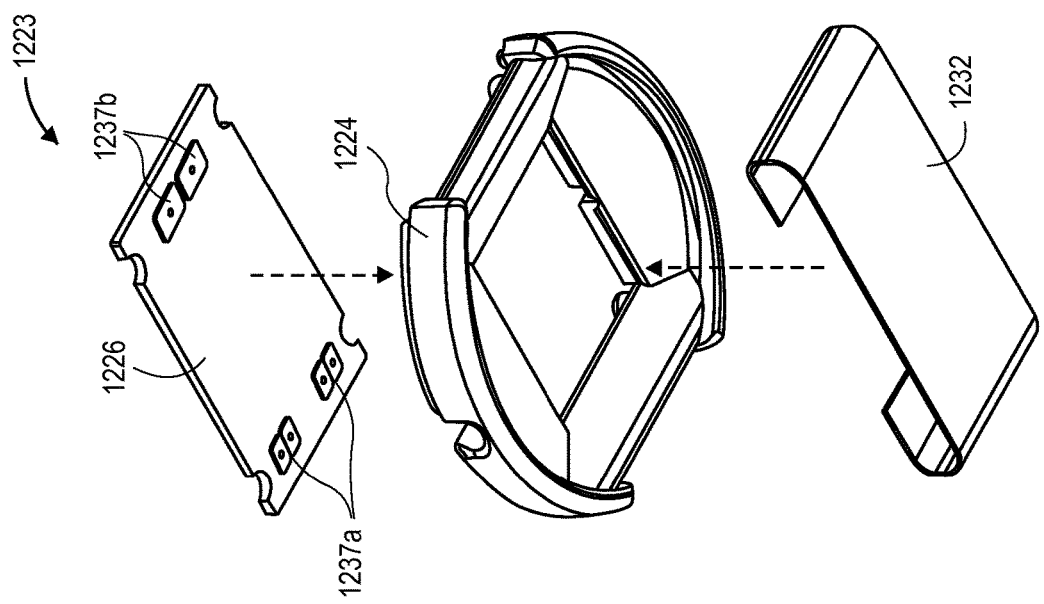

FIGS. 12I-12J are top and bottom exploded, perspective views, respectively, of the frame sub-assembly 1223, in accordance with embodiments described herein. As shown, the underside of the PCB 1226 can include one or more contacts 1237a, 1237b that may come into contact with one or more contacts on sides of the stacked sensing elements 1232. The stacked sensing elements 1232 can be any of those described herein. In the illustrated embodiment, for example, the stacked sensing elements 1232 are the piezoelectric films described in FIGS. 5A-5E having flooded electrode surfaces, respectively, which form the outer surfaces of the piezoelectric stack. Moreover, the stacked sensing elements 1232 include one or more vias or through holes extending an electrode from surfaces of the films to corresponding regions on the opposing surfaces of the respective films. As discussed above, this configuration enables coupling of the four electrodes (e.g., the anode and cathode for each film) to the appropriate contacts on the underside of the PCB 1226.

For example, in one embodiment, the region 521*b* (FIG. 5D) of the flooded cathode coating on the outer surface of the second film 521 touches one or more of the contacts 1237*a*, 1237*b* on the underside of the PCB 1226. Meanwhile, the through-holed regions 521*a*, 520*b* (FIG. 5D) of the outer surface of the second film 521 may touch one or more of the contacts 1237*a*, 1237*b* on the underside of the PCB 1226.

According to the above-described connection scheme, the stacked sensing elements 1232 can be coupled to circuitry (not shown) residing on and/or in the PCB 1226 or other system component (e.g., the hub or monitor) to provide improved SNR and/or electrical shielding. For example, the electrodes of the stacked sensing elements 1232 can each be coupled to an input of an attenuation circuit (e.g., a differential amplifier) or ground (or other common potential) in the manner illustrated schematically with respect to FIG. 3B above. Specifically, although other connections schemes are possible, in one embodiment, the contacts 1237*a* on the PCB 1226 couple the flooded, outer cathode of the second, exterior film 521 to ground, and the contacts 1237*b* couple the inner, un-flooded anode of the second, exterior film 521, and the inner, un-flooded cathode of the first, interior film 520, to a first (e.g., positive) and second (e.g., negative) terminals, respectively, of a difference amplifier or other noise attenuation circuit.

As described above, the sensor cable-to-PCB connections 1227 may provide connections to the sensor cable 1214, and thereby the patient monitor.

In an embodiment, the PCB 1226 and the frame 1224 effectively sandwich the portion of the stacked sensing elements 1232 wrapped around the frame 1224 so as to provide a secure electrical connection with the contacts 1237*a*, 1237*b* and to protect the contact between the stacked sensing elements 1232 and the contacts 1237*a*, 1237*b*, e.g., from shorts due to contact with moisture. Accordingly, in an embodiment the top side of the PCB 1226 and associated electrical components (e.g., electronic components, electrical leads, and/or electrical contacts) disposed thereon may be isolated from the cavity 1236. For example, the coupling of the PCB 1226 to the frame 1224, and insertion of the frame sub-assembly 1223 into the acoustic coupler 1216, may create a barrier between the cavity 1236 and the top side of the PCB 1226. In an embodiment, components of the sensor 1200 additionally provide a barrier between the top side of the PCB 1226 and any ambient air (as provided, for example, by one or more pressure equalization pathways between the cavity 1236 and ambient air. Isolation of the top side of the PCB 1226 may prevent exposure of any electronics and/or electrical contacts of the sensor 1200 to, for example, moisture from the patient to which the sensor 1200 is attached. Accordingly, the electronics and/or electrical contacts of the sensor 1200 may be protected from deterioration and/or various harmful effects.

As shown in FIGS. 12I and 12J, the frame 1224 includes cutout sections on either side of the frame where the stacked sensing elements 1232 wrap around the frame 1224. The cutout sections include cutouts on the sides of the frame 1224, as well as the bottom of the frame 1224, such that the stacked sensing elements 1232 fit within the cutout sections when wrapped around the frame. The cutout sections may advantageously provide a lower profile to the sensor 1200 than if the stacked sensing elements 1232 wrapped around the frame without cutout sections.

Figure 12K:
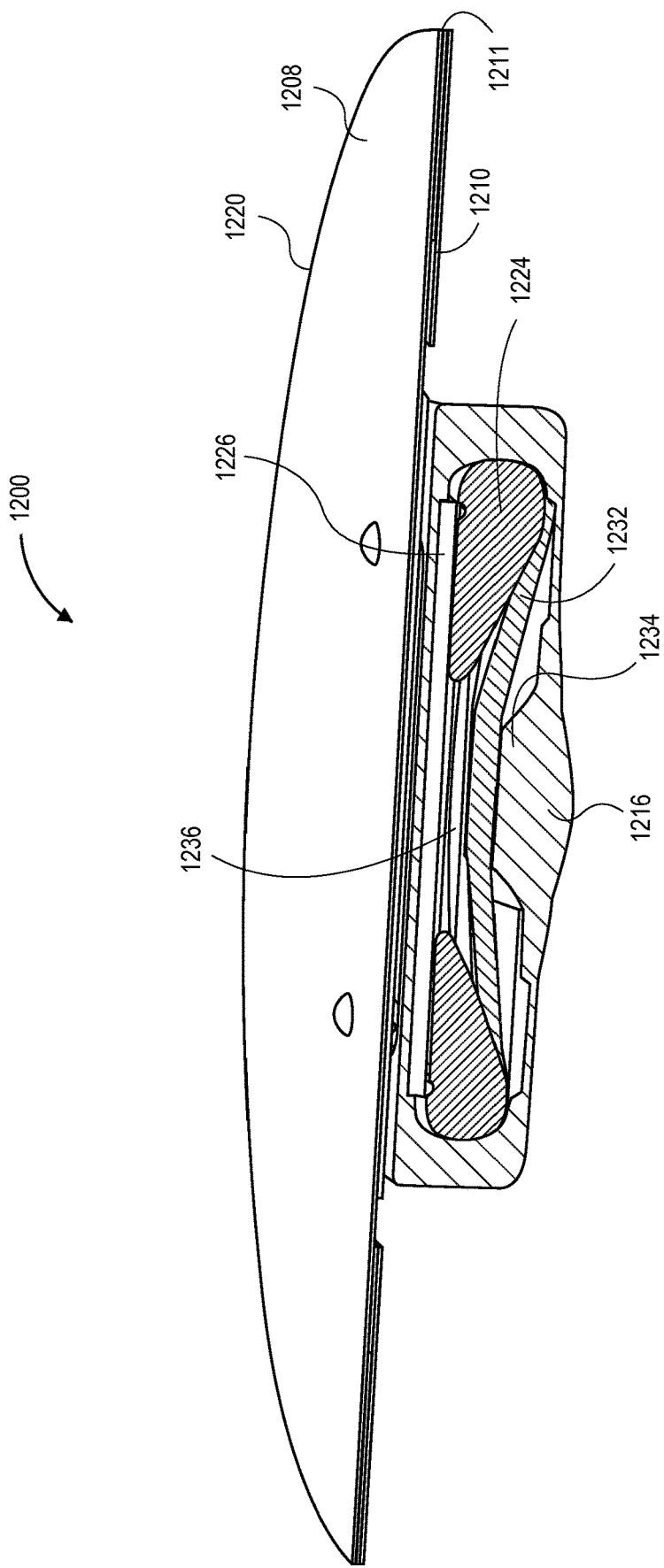
FIG. 12K shows a cross-sectional view of the sensor of FIGS. 12A-12B, in accordance with an embodiment described herein.

FIG. 12K shows a cross-sectional view of the sensor 1200, in accordance with various embodiments described above with respect to FIGS. 12A-12J above, in which the sensor is not attached to a patient.

Figure 12L:
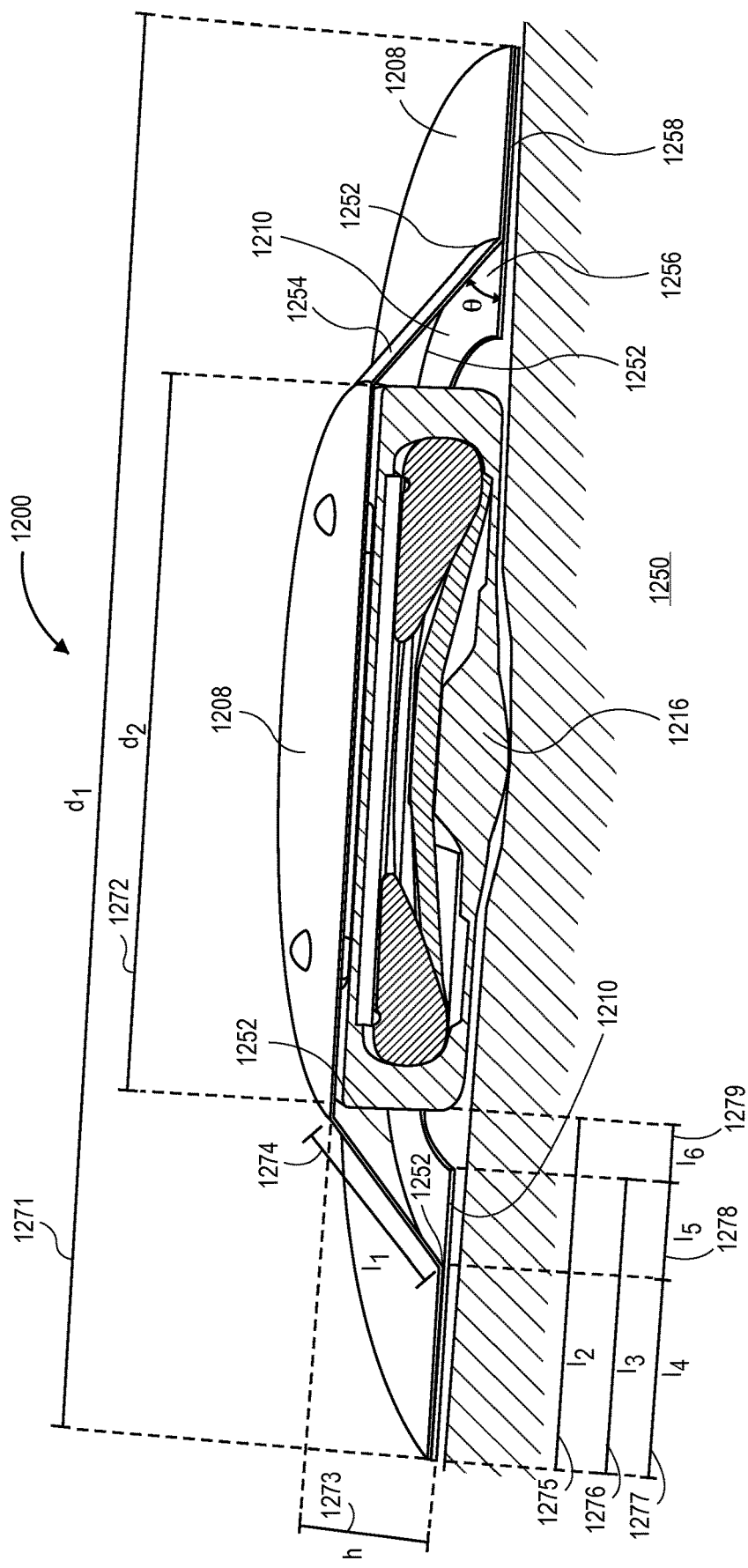
FIG. 12L shows another cross-sectional view of the sensor of FIGS. 12A-12B in which the sensor is attached to a patient, in accordance with an embodiment described herein.

FIG. 12L shows another cross-sectional view of the sensor 1200, in accordance with various embodiments described above with respect to FIGS. 12A-12J above, in which the sensor is attached to tissue site of a patient 1250. As shown, when the sensor 1200 is attached to a patient, a stretchable portion 1254 of the deformable patient coupler 1208, which may be formed from a resilient and/or elastic material, stretches from the top of the sensor sub-assembly 1222 down towards the patient's skin. The stretchable portion 1254 terminates at a location 1252, at the beginning of an adhesive interface between the stretchable portion 1254 and the adhesive portion 1210, thereby forming an angle θ between the stretchable portion 1254 and the adhesive portion 1210. In the illustrated embodiment, the interface 1252 between the stretchable portion 1254 and the adhesive portion 1210 extends circumferentially around the sensor 1200 when looking down on the top of the sensor 1200 towards the patient's skin. The adhesive portion 1210 is shown as attached to the patient at an area 1258. By locating the point of attachment 1252 between the stretchable portion 1254 and the adhesive portion 1210 away from one or more of the inner edge and the outer edge of the adhesive portion 1210 in the manner shown, a tendency of the adhesive portion 1210 to peel off the patient may be reduced. In various embodiments, the point 1252, where the deformable patient coupler 1208 couples to the adhesive portion 1210, may be located at any point along the surface of the adhesive portion 1210. Accordingly, the angle 1256 may be optimized so as to enable a secure coupling of the sensor 1200 to the patient, reduce the tendency of the adhesive portion 1210 to peel off the patient, and/or provide an appropriate amount of force applied by the deformable patient coupler 1208 on the sensor sub-assembly 1222 to couple acoustic energy efficiently to the sensing elements.

In one embodiment, an outer perimeter of the adhesive portion 1210 has a diameter 1271 (as indicated by length d1) of 45 millimeters, the outer perimeter of the acoustic coupler 1216 has a diameter 1272 (as indicated by length d2) of 24 millimeters and a height 1273 (as indicated by length h) of 4 millimeters, a distance 1275 (as indicated by length l2) from the outer perimeter of the acoustic coupler 1216 to the outer perimeter of the adhesive portion 1210 is 10.5 millimeters, the adhesive portion 1210 has a width 1276 (as indicated by length l3) of 9.25 millimeters, a distance 1279 (as indicated by length l6) from an inner perimeter of the adhesive portion 1210 and the outer perimeter of the acoustic coupler 1216 is 1.25 millimeters, the interface 1252 is located 7.2 millimeters (as indicated by length l4 1277) from an edge of the outer perimeter of the adhesive portion 1210 and 2.05 millimeters (as indicated by length l5 1278) from an edge of the inner perimeter of the adhesive portion 1210 such that the length of the stretched portion 1274 (as indicated by length l1) is about 5.2 millimeters and the angle θ is about 51 degrees. In various embodiments, the various dimensions and angles described above may vary together and/or independently from the values given. For example, in one embodiment the various dimensions and angles described above may vary (higher and/or lower) together and/or independently by 1%, 2%, 3%, 4%, 5%, 6%, 7%, 8%, 9%, 10%, and/or any higher percentage from the values given.

In one embodiment, the diameter 1271 is within a range of 30-60 millimeters, the diameter 1272 is within a range of 15-35 millimeters, the height 1273 is within a range of 3-7 millimeters, the width 1276 is within a range of 5-25 millimeters, and the distance 1279 is within a range of 0.25-10 millimeters.

In one embodiment, the interface 1252 may be located closer to either the inner or outer perimeter of the adhesive portion 1210 while maintaining the advantages described herein. For example, in one embodiment the interface 1252 is located within the range of 2-8 millimeters from the edge of the outer circumference of the adhesive portion 1210 such that the angle θ may be about 25-60 degrees when the sensor is attached to the patient. In various implementations the interface 1252 is located at least about 0.25, 0.50, 0.75, 1, 2, 3, 4, 5, 6, 7, 8, 9, 10, 15, or 20 millimeters from the edge of the outer circumference of the adhesive portion 1210, with greater distances generally resulting in greater reduction in peeling force. The interface 1252 in some embodiments is located within a range of 0.5 and 8 millimeters from the edge of the inner circumference of the adhesive portion 1210. In various implementations the interface 1252 is located at least about 0.25, 0.50, 0.75, 1, 2, 3, 4, 5, 6, 7, 8, 9, 10, 15, or 20 millimeters from the edge of the inner circumference of the adhesive portion 1210, with greater distances generally resulting in greater reduction in peeling force. Depending on the embodiment, any combination of the above values is possible. For instance, in one embodiment, the distance from the interface 1252 to the edge of the outer circumference of the adhesive portion 1210 is at least 5 millimeters, while the distance from the interface 1252 to the edge of the inner circumference of the adhesive portion is at least 1 millimeter.

Additionally, in one embodiment semi-spherical cap portion of the acoustic coupler may extend beyond the generally flat bottom portion of the acoustic coupler by about 1 millimeter, and may have a diameter of about 10 millimeters. In some other embodiments, the semi-spherical cap portion may extend 0.5-5 millimeters beyond the generally flat bottom portion of the acoustic coupler, and may have a diameter of 20-100% of the diameter 1272 of the acoustic coupler. For example, as described above in reference to FIGS. 6A-6L, the semi-spherical cap has a diameter equal to the diameter of the acoustic coupler. Further, in one embodiment the semi-spherical cap is centered on the bottom portion of the acoustic coupler when viewed from the bottom. In some other embodiments the semi-spherical cap may be off-center when viewed from the bottom, and/or may have a shape other than semi-spherical (as described above).

In an embodiment the sensor 1200 may incorporate stacked sensing elements and a PCB in various different configurations including, for example, as shown and described in reference FIG. 6M above. In an embodiment the sensor 1200 may incorporate an additional adhesive portion similar to the additional adhesive portion shown and described above in reference to FIG. 10.

In various embodiments described above, providing attachment of the sensor to the patient completely, or substantially completely, around the perimeter of the sensor (as provided by, for example, the adhesive portion 1210 and/or the extended adhesive portion 1006) enables improved coupling of the sensor to the patient. Improved coupling of the sensor to the patient may further enable other advantages, for example, improved SNR. Additionally, when the adhesive portion of the sensor extends around the perimeter of the sensor, coupling of the sensor to the patient with substantially even force across the entire sensor (or a large portion thereof) may be applied. For example, the design of the sensor may enable the acoustic coupler of the sensor to be pressed against the skin of the patient with roughly even force around and across the acoustic coupler. In an embodiment, a bandage or tape may be used in addition to, or in place of, the adhesive portion to attach the sensor to the measurement site of the patient. Moreover, such bandages or tapes may be a variety of different shapes including generally elongate, circular and oval, for example.

In various embodiments, and also as described above, the deformable patient coupler (for example, the deformable patient coupler 1208) provides a compliant, deformable, layer that enables improved coupling and/or attaching of the sensor to the patient. The deformable patient coupler can further improve patient coupling and may provide other advantages, such as improved SNR. In various embodiments, and as with the adhesive portion described above, providing attachment of the sensor to the patient completely, or at least partially, around the perimeter of the sensor via the deformable patient coupler enables improved coupling of the sensor to the patient. This improved coupling may result due to the coupling of the sensor to the patient with substantially even force as described above. The combination of the deformable patient coupler and the adhesive portion enables the acoustic coupler of the sensor to be pressed against the skin of the patient with substantially equal force around and across the acoustic coupler.

In various embodiments, and as described above, an acoustic coupler is provided in the sensor 1200 that spans and/or extends across a portion of the bottom portion of the sensor and/or the sensor sub-assembly. In an embodiment, the sensor 1200 may include an acoustic coupler, such as the acoustic coupler 616 of FIGS. 6A-6M that may span across an entire bottom portion of the sensor 1200. In any of the embodiments described above, the acoustic coupler 1216 provides a large patient contact area with may provide improved SNR and/or coupling of acoustic signals from the patient to the sensor. Additionally, the semi-spherical and/or spherical cap shape of the acoustic coupler may provide an even, or semi-even, propagation distance between the skin of the patient and the sensor elements, providing further improved sensor performance.

In various embodiments, the design of the sensor 1200 described above reduces the likelihood of the sensor from becoming de-coupled from the patient due to, for example, patient movement. For example, the adhesive portion that surrounds the perimeter or circumference of the sensor provides substantially even attachment force around and/or across the sensor. Additionally, the deformable patient coupler may provide for further constant and/or homogeneous pressure of the sensor to the skin of the patient even as the patient moves or flexes. Further, in the embodiments described above, as the deformable patient coupler 1208 couples to the adhesive portion 1210 at a middle portion of the adhesive portion 1210, the adhesive portion 1210 may be more securely attached to the patient as an edge of the adhesive portion 1210 may not be pulled from the patient's skin by an edge.

In various embodiments, design of the sensor 1200 advantageously enables the sensor to be compact. For example, the relatively small size of the frame and sensor subassembly can allow the sensor to be attached comfortably to contoured, generally curved portions of the patient's body. For, example, the sensor can be comfortably attached to portions of the patient's neck whereas a larger frame may be awkwardly situated on the patient's neck or other contoured portion of the patient. The size of the sensor may allow the sensor to be attached to the patient in a manner allowing for improved sensor operation. For example, the relatively small sensor sub-assembly, when combined with the relatively large acoustic coupler and the attachment sub-assembly, allows the sensor to be applied with substantially uniform pressure across the patient contact area. Further, the relatively small size of the sensor may enable use of the sensor in neonatal applications where, for example, it may fit on a portion of a newborn's body without being too obtrusive or uncomfortable.

Pressure Equalization Pathways

In various embodiments, the sensor 600 and/or the sensor 1200 may include one or more pressure equalization pathways, for example, pressure equalization pathways 615, 628, 1215, and/or 1228. The pressure equalization pathways 615, 628, 1215, and/or 1228 provide an air communication pathway between the cavities 636 or 1236 and ambient air pressure. The pressure equalization pathways 615, 628, 1215, and/or 1228 allow the sensor's membrane(s) or film(s) (for example, stacked sensing elements 632 and/or 1232) to vibrate within the cavities 636 and/or 1236 independent of skin elasticity or the force used to attach the sensor to a patient's skin.

Indeed, variability in skin elasticity or the force used to attach the acoustic sensor to the medical patient's skin can affect the volume and/or air pressure within the cavities 636 and/or 1236 defined by the sensing elements 632 and/or 1232, frames 624 and/or 1224, and PCBs 626 and/or 1226, respectively. Variability in skin elasticity or attachment force can lead to variability in cavity resonance, which can cause unwanted variability in sensor performance. For example, an acoustic sensor (for example, acoustic sensors sensor 600 and/or 1200) that is attached to very elastic skin may provide a different output signal than an acoustic sensor that is attached to firmer or tighter skin. Similarly, an acoustic sensor that is loosely attached to patient's skin may provide a different output signal than an acoustic sensor that is tightly attached to a patient's skin.

To compensate for attachment variability, in one embodiment the acoustic sensor frame (for example, acoustic sensor frames 624 and/or 1224) includes one or more pressure equalization pathways for example, pressure equalization pathways 615, 628, 1215, and/or 1228). The pressure equalization pathways provide an air-flow channel from the cavity (for example, the cavities 636 and/or 1236) to the ambient air pressure. By equalizing pressure within the cavity with ambient during sensing, variability in sensor performance may be reduced and/or eliminated. In some embodiments, the pressure equalization pathways include one or more holes, notches, ports, or channels that extend from within the sensor's cavity to a location in communication with ambient air pressure.

In one embodiment, the pressure equalization pathways are provided on opposite sides of the frame (for example, frames 624 and/or 1224) portion that defines an acoustic cavity, or in symmetric positions on a cap (for example, cap 604 and/or cap/deformable patient coupler 1208). Symmetrically arranging the pressure equalization pathways can further improve sensor performance. In another embodiment the pressure equalization pathways are provided in portions of the sensor frame which do not contact the sensor's sensing elements, membranes, and/or films. By preventing contact between the pressure equalization pathways and the sensor's sensing membrane, sensor performance may be further improved.

In one embodiment, the sensor frame and/or cap includes one, two, three, four, or five pressure equalization pathways on each of two opposite sides of the sensor frame. In another embodiment, the sensor frame includes at least one pressure equalization pathway on each of its sides. In one embodiment, one or more of the pressure equalization pathways are formed as notches. A frame that includes notches as its pressure equalization pathways may be easier to fabricate than a frame that includes other pressure equalization pathways (e.g., holes). For example, when the frame is made by molding plastic, creating notches in the frame's side wall may require less complicated tooling than forming holes.

Support Frame

The frame (for example, frame 624 and/or frame 1224 described above) generally supports the various components of the sensor. For example, the one or more piezoelectric elements, electrical shielding barriers, attachment element and other components may be attached to the frame. The frame can be configured to hold the various components in place with respect to the frame and with respect to one another, thereby beneficially providing continuous operation of the sensor under a variety of conditions, such as during movement of the sensor. For example, the frame can be configured to hold one or more of the components together with a predetermined force. Moreover, the frame can include one or more features which can improve the operation of the sensor. For example, the frame can include one or more cavities which allow for the piezoelectric element to move freely and/or which amplify acoustic vibrations from bodily sounds of the patient. In various embodiments, the frame may have a generally circular and/or rectangular shape, as viewed from the top or bottom, although the frame shape could be any shape, including square, oval, elliptical, elongated, etc. For example, in the embodiment shown in FIGS. 12A-12L the frame 1224 has a generally elliptical (for example, circular) cross-sectional profile, when viewed from a top of the frame.

In an embodiment, the frame and/or PCB define a cavity in an underside portion. In an assembled configuration, the sensing elements are wrapped around the frame in the direction of the transverse axis such that the lower planar portion of the sensing element stretches across the cavity. As such, the cavity can serve as an acoustic chamber of the multi-parameter sensor assembly. The sensing elements thus have freedom to move up into the acoustic chamber in response to acoustic vibrations, allowing for the mechanical deformation of the piezoelectric sensing material and generation of the corresponding electrical signal. In addition, the chamber of certain embodiments allows sound waves incident on the sensing element to reverberate in the chamber. As such, the sound waves from the patient may be amplified or more effectively directed to the sensing elements, thereby improving the sensitivity of the sensing elements. As such, the cavity allows for improved operation of the sensor.

The frame may include one or more contacts, such as locking posts, extending from the frame which press into corresponding contact strips of the PCB, helping to ensure a stable, relatively constant contact resistance between the PCB and the sensing elements. The construction of the frame and sensor sub-assembly helps ensure a stable, constant contact resistance between the PCB and the sensing elements.

Sensing Elements

The sensing elements of certain embodiments are configured to sense acoustic vibrations from a measurement site of a medical patient. In one embodiment, the sensing elements are piezoelectric films, such as described in U.S. Pat. No. 6,661,161, incorporated in its entirety by reference herein, and in the '883 Application. In some embodiments, the sensing elements include one or more of crystals of tourmaline, quartz, topaz, cane sugar, and/or Rochelle salt (sodium potassium tartrate tetrahydrate). In other embodiments, the sensing elements include quartz analogue crystals, such as berlinite ($AlPO_4$) or gallium orthophosphate ($GaPO_4$), or ceramics with perovskite or tungsten-bronze structures ($BaTiO_3$, $SrTiO_3$, $Pb(ZrTi)O_3$, $KNbO_3$, $LiNbO_3$, $LiTaO_3$, $BiFeO_3$, $Na_xWO_3$, $Ba_2NaNb_5O_5$, $Pb_2KNb_5O_{15}$).

In other embodiments, the sensing elements are made from a polyvinylidene fluoride plastic film, which develops piezoelectric properties by stretching the plastic while placed under a high pooling voltage. Stretching causes the film to polarize and the molecular structure of the plastic to align. For example, stretching the film under or within an electric field causes polarization of the material's molecules into alignment with the field. A thin layer of conductive metal, such as nickel-copper or silver is deposited on each side of the film as electrode coatings, forming electrical poles. The electrode coating provides an electrical interface between the film and a circuit.

In operation, the piezoelectric material becomes temporarily polarized when subjected to a mechanical stress, such as a vibration from an acoustic source. The direction and magnitude of the polarization depend upon the direction and magnitude of the mechanical stress with respect to the piezoelectric material. The piezoelectric material will produce a voltage and current, or will modify the magnitude of a current flowing through it, in response to a change in the mechanical stress applied to it. In one embodiment, the electrical charge generated by the piezoelectric material is proportional to the change in mechanical stress of the piezoelectric material.

Piezoelectric material generally includes first and second electrode coatings applied to the two opposite faces of the material, creating first and second electrical poles. The voltage and/or current through the piezoelectric material are measured across the first and second electrical poles. Therefore, stresses produced by acoustic waves in the piezoelectric material will produce a corresponding electric signal. Detection of this electric signal is generally performed by electrically coupling the first and second electrical poles to a detector circuit. In one embodiment, a detector circuit is provided with the PCB, as described in greater detail below.

By selecting the piezoelectric material's properties and geometries, a sensor having a particular frequency response and sensitivity can be provided. For example, the piezoelectric material's substrate and coatings, which generally act as a dielectric between two poles, can be selected to have a particular stiffness, geometry, thickness, width, length, dielectric strength, and/or conductance. For example, in some cases stiffer materials, such as gold, are used as the electrode. In other cases, less stiff materials, such as silver, are employed. Materials having different stiffness can be selectively used to provide control over sensor sensitivity and/or frequency response.

The piezoelectric material, or film, can be attached to, or wrapped around, a support structure, such as the frame described above. The geometry of the piezoelectric material can be selected to match the geometry of the frame. Overall, the sensor can optimized to pick up, or respond to, a particular desired sound frequency, and not other frequencies. The frequency of interest generally corresponds to a physiological condition or event that the sensor is intended to detect, such as internal bodily sounds, including, cardiac sounds (e.g., heart beats, valves opening and closing, fluid flow, fluid turbulence, etc.), respiratory sounds (e.g., breathing, inhalation, exhalation, wheezing, snoring, apnea events, coughing, choking, water in the lungs, etc.), or other bodily sounds (e.g., swallowing, digestive sounds, gas, muscle contraction, joint movement, bone and/or cartilage movement, muscle twitches, gastro-intestinal sounds, condition of bone and/or cartilage, etc.).

The surface area, geometry (e.g., shape), and thickness of the piezoelectric material generally defines a capacitance. The capacitance is selected to tune the sensor to the particular, desired frequency of interest. Furthermore, the frame is structured to utilize a desired portion and surface area of the piezoelectric material.

The capacitance of the sensor can generally be expressed by the following relationship: $C=\varepsilon S/D$, where C is the sensor's capacitance, $\varepsilon$ is the dielectric constant associated with the material type selected, S is the surface area of the material, and D is the material thickness (e.g., the distance between the material's conducive layers). In one embodiment, the piezoelectric material (having a predetermined capacitance) is coupled to an sensor impedance (or resistance) to effectively create a high-pass filter having a predetermined high-pass cutoff frequency. The high-pass cutoff frequency is generally the frequency at which filtering occurs. For example, in one embodiment, only frequencies above the cutoff frequency (or above approximately the cutoff frequency) are transmitted.

The amount of charge stored in the conductive layers of the piezoelectric material is generally determined by the thickness of its conductive portions. Therefore, controlling material thickness can control stored charge. One way to control material thickness is to use nanotechnology or MEMS techniques to precisely control the deposition of the electrode layers. Charge control also leads to control of signal intensity and sensor sensitivity. In addition, as discussed above, mechanical dampening can also be provided by controlling the material thickness to further control signal intensity and sensor sensitivity.

One embodiment of a piezoelectric sensing element is provided in FIGS. 11A-11C. The sensing element 1100 includes a substrate 1102 and coatings 1104, 1106 on each of its two planar faces 1108, 1110. The planar faces 1108, 1110 are substantially parallel to each other. At least one through hole 1112 extends between the two planar faces 1108, 1110. In one embodiment, the sensing element 1100 includes two or three through holes 1112.

In one embodiment, a first coating 1104 is applied to the first planar face 1108, the substrate 1102 wall of the through holes 1112, and a first conductive portion 1114 of the second planar face 1110, forming a first electrical pole. By applying a first coating 1104 to the through holes 1112, a conductive path is created between the first planar face 1108 and the first conductive portion 1114 of the sensing element 1100. A second coating 1106 is applied to a second conductive portion 1116 of the second planar face 1110 to form a second electrical pole. The first conductive portion 1114 and second conductive portion 1116 are separated by a gap 1118 such that the first conductive portion 1114 and second conductive portion 1116 are not in contact with each other. In one embodiment, the first conductive portion 1114 and second conductive portion 1116 are electrically isolated from one another.

In some embodiments, the first and second conductive portions 1114, 1116 are sometimes referred to as masked portions, or coated portions. The conductive portions 1114, 1116, can be either the portions exposed to, or blocked from, material deposited through a masking, or deposition process. However, in some embodiments, masks aren't used. Either screen printing, or silk screening process techniques can be used to create the first and second conductive portions 1114, 1116.

In another embodiment, the first coating 1104 is applied to the first planar face 1108, an edge portion of the substrate 1102, and a first conductive portion 1114. By applying the first coating 1104 to an edge portion of the substrate 1102, through holes 1112 can optionally be omitted.

In one embodiment, the first coating 1104 and second coating 1106 are conductive materials. For example, the coatings 1104, 1106 can include silver, such as from a silver deposition process. By using a conductive material as a coating 1104, 1106, the multi-parameter sensor assembly can function as an electrode as well.

Electrodes are devices well known to those of skill in the art for sensing or detecting the electrical activity, such as the electrical activity of the heart. Changes in heart tissue polarization result in changing voltages across the heart muscle. The changing voltages create an electric field, which induces a corresponding voltage change in an electrode positioned within the electric field. Electrodes are typically used with echo-cardiogram (EKG or ECG) machines, which provide a graphical image of the electrical activity of the heart based upon signal received from electrodes affixed to a patient's skin.

Therefore, in one embodiment, the voltage difference across the first planar face 1108 and second planar face 1110 of the sensing element 1100 can indicate both a piezoelectric response of the sensing element 1100, such as to physical aberration and strain induced onto the sensing element 1100 from acoustic energy released from within the body, as well as an electrical response, such as to the electrical activity of the heart. Circuitry within the sensor assembly and/or within a physiological monitor (not shown) coupled to the sensor assembly distinguish and separate the two information streams. One such circuitry system is described in the '883 Application which is expressly incorporated by reference herein.

Referring still to FIGS. 11A-11C, the sensing element 1100 is flexible and can be wrapped at its edges, as shown in FIG. 11C. In one embodiment, the sensing element 1100 is the sensing element 632 wrapped around the frame 624, as shown in FIGS. 6H and 6I. In addition, by providing both a first conductive portion 1114 and a second conductive portion 1116, both the first coating 1104 and second coating 1106 and therefore the first electrical pole of and the second electrical pole of the sensing element 1100 can be placed into direct electrical contact with the same surface of the PCB, such as the PCB 636 as shown FIGS. 6H-6K above. This advantageously provides symmetrical biasing of the sensing element 1100 under tension while avoiding uneven stress distribution through the sensing element 1100.

In addition, controlling the tension of the sensing elements in the region where the mechanical stress (e.g., mechanical stress due to acoustic vibration from a patient's skin) is incident upon the sensing elements can serve to improve the sensitivity of the sensing elements and/or the coupling between the source of the signal (e.g., the patient's skin) and the sensing elements. This feature facilitated by the coupler described above and below.

Bonding and/or Adhesive Layers

The various bonding layers and/or adhesive layers described herein (including, for example, adhesive layers of the sensor 600 and/or the sensor 1200 including adhesives joining the various components of the attachment sub-assemblies 620 and/or 1220 to one another, the attachment sub-assemblies 620 or 1220 to the sensor sub-assemblies 622 and/or 1222 (respectively), the sensors 600 and/or the 1200 to the patient, and/or the sensing element layers) may each comprise various materials according to various embodiments. In certain embodiments, the bonding and/or adhesive layers are elastomer, rubber, plastic, tape, such as a cloth tape, foam tape, or adhesive film, or other compressible material. For example, in one embodiment, one or more of the bonding and/or adhesive layers are conformable polyethylene film coated with a high tack, high peel acrylic adhesive. In an embodiment, one or more of the adhesive layers that contact the patient's skin include a diaphoretic adhesive, or a diaphoretic tape.

The bonding and/or adhesive layers advantageously form a physical insulation layer or seal between the components of the sensor preventing substances entering and/or traveling between certain portions of the sensor. In many embodiments, for example, the bonding and/or adhesive layers form a physical insulation layer that is water resistant or water proof, thereby providing a water-proof or water-resistant seal. The water-resistant properties of the bonding and/or adhesive layers provide the advantage of preventing moisture from entering various sections of the sensor. In certain embodiments, the bonding and/or adhesive layers can prevent moisture, such as perspiration, or other fluids, from entering portions of the sensor sub-assembly, such as the acoustic cavity when worn by a patient. This is particularly advantageous when the patient is wearing the sensor during physical activity. The water-resistant seal prevents current flow and/or a conductive path from forming from one surface of the sensing elements to another surface of the sensing elements as a result of patient perspiration or some other moisture entering and/or contacting the sensing elements.

The bonding and/or adhesive layers can also provide electrical insulation among the components of the sensor, preventing the flow of current among certain portions of the sensor.

Electrical Noise Shielding Barrier

An electrical noise shielding barrier can electrically shield the electrical poles of the sensing element from external electrical noises. In some embodiments the electrical shielding barrier can include one or more layers which form a Faraday cage around a piezoelectric sensing element, and which distribute external electrical noise substantially equally to the electrical poles of the piezoelectric sensing element. In addition, the shielding barrier flexibly conforms to the surface shape of the piezoelectric element as the surface shape of the piezoelectric element changes, thereby improving the shielding and sensor performance. In an embodiment, as described above, electrode layers deposited directly on the outsides of the two stacked sensing element membranes may form a shielding barrier, which acts acts to reduce the effect of noise on the sensing elements from sources such as external static electrical fields, electromagnetic fields, and the like.

The inner and outer shield layers may include conductive material. For example, the inner and outer shield layers may include copper in certain embodiments and are advantageously formed from a thin copper tape such that the layers can conform to the shape, contours and topology of the sensor element. In some configurations, other materials (e.g., other metals) or other combinations of materials can be used. Moreover, as described above, the electrical shielding barrier or portions thereof, can be formed from piezoelectric films.

In certain embodiments, the shield layers are coupled to a common potential (e.g., ground) or are otherwise operatively coupled, and each of the shield layers are also electrically (e.g., capacitively) coupled to one or more of the poles of the sensing elements.

As discussed, the electrical shielding barrier such as the Faraday cage formed by the inner and outer shield layers helps to reduce the effect of noise electrical noise on the sensing elements from sources such as external static electrical fields and electromagnetic fields, thereby lowering the noise floor, providing better noise immunity, or both. For example, the electrical shielding barrier allows for the removal of electrical interference or noise incident directed towards the sensing element while allowing the non-noise component of the sensed signal indicative of bodily sounds to be captured by the sensor. For example, in one embodiment the sensing element is a piezoelectric film such as one of the piezoelectric films described herein having positive and negative electrical poles and configured in a differential mode of operation. The electrical shielding barrier acts to balance the effect of the noise by distributing at least a portion of the noise substantially equally to the positive and negative electrical poles of the piezoelectric element. In some embodiments, the electrical shielding barrier distributes the noise equally to both the positive and negative poles. Moreover, the noise signals distributed to the positive and negative electrical poles are substantially in phase or actually in phase with each other. For example, the noise signals distributed to the positive and negative poles are substantially similar frequencies and/or amplitudes with substantially no phase shift between them.

For example, in certain embodiments, noise incident on the shielding barrier is substantially equally distributed to each of the shielding layers because these layers are at a common potential (e.g., ground). The substantially equally distributed noise may then be coupled (e.g., capacitively coupled) to the poles of the sensing elements. In certain embodiments, at least some of the external electrical noise is shunted or otherwise directed to ground by the shield layers instead of, or in addition to, being distributed to the poles of the sensing elements.

Because the noise signal components on the positive and negative poles are substantially in phase, the difference between the noise components on the respective poles is negligible or substantially negligible. On the other hand, the difference between the differential non-noise sensor signal components indicative of bodily sounds on the positive and negative poles will be non-zero because the sensing element is configured in a differential mode. As such, the noise signals can advantageously be removed or substantially removed through a common-mode rejection technique.

For example, a common-mode rejection element may receive a signal including the combined noise and non-noise sensor signal components of the positive and negative poles, respectively. The common-mode rejection element is configured to output a value indicative of the difference between the combined signal on the positive pole and the combined signal on the negative pole. Because the difference between the noise signals is negligible, the output of the common-mode rejection element will be substantially representative of the non-noise component of the sensor signal and not include a significant noise component. The common mode rejection element may include, for example, an operational amplifier. In one embodiment, for example, three operational amplifiers (not shown) are used and they are disposed on the PCB.

Because the shielding layers conform to the topology of the frame and the sensing elements, the shielding layers are physically closer to the electrical poles of the sensing elements and are more uniformly displaced from the sensing elements. Moreover, the outer shield layer of certain embodiments actively moves with and conforms to the contours of the sensing elements during use, such as when the sensor assembly is placed against the skin or when the sensing elements are moving due to acoustic vibrations. For example, when placed against the skin, the coupling element (or acoustic coupler) pushes against both the outer shielding layer of the outer sensing element and the inner shielding layer of the inner sensing element, causing them to curve along the inside surface of the coupler. Because the cage is flexible and can conform to the movement of the shielding elements, the shielding performance and sensor performance is improved. This arrangement provides advantages such as for example, for the noise signals to be more accurately and evenly distributed to the positive and negative electrical poles of the sensing elements by the shielding layers, thereby providing enhanced noise reduction. This arrangement can also provide for improved manufacturability and a more stream-lined design.

Acoustic Coupler

The sensor may also include an acoustic coupler or biasing element (as described above), which may advantageously improve the coupling between the source of the signal to be measured by the sensor (e.g., the patient's skin) and the sensing element. The acoustic coupler generally includes a coupling portion positioned to apply pressure to the sensing element so as to bias the sensing element in tension. For example, the acoustic coupler may include one or more bumps, posts, or raised portions which provide such tension. The bumps, posts or raised portions may be positioned on the inner surface of the coupler, the outer surface of the coupler, or both and may further act to evenly distribute pressure across the sensing elements. In addition, the acoustic coupler can be further configured to transmit bodily sound waves to the sensing elements. The acoustic coupler can also be configured to provide electrical isolation between the patient and the electrical components of the sensor.

In an embodiment, the acoustic coupler generally forms a dielectric barrier between the patient and the electrical components of the sensor assembly. As such, the acoustic coupler provides electrical isolation between the patient and the electrical components of the sensor subassembly. This is advantageous in avoiding potential harmful electrical pathways or ground loops forming between the patient and the sensor.

In certain embodiments, as described above, the acoustic coupler includes a bump, protrusion, or coupling element on the inner surface of the coupler configured to advantageously bias the sensing membrane in tension. The coupling element of the illustrated embodiment is a generally rectangular bump which extends by some height into the cavity which is formed on the interior of the sensor. Because the sensing elements may be generally taut in tension under the pressure of the coupling bump, the sensing elements will be mechanically coupled to the coupling bump and responsive to acoustic vibrations travelling through the coupler to the sensing elements, thereby providing improved coupling between the patient's skin and the sensing element. As such, the acoustic coupler provides for improved measurement sensitivity, accuracy, or both, among other advantages.

The acoustic coupler is further configured to transmit bodily sound waves to the sensing elements. The coupler can further include a portion disposed on the outer surface of the coupler and which is configured to contact the skin during use. For example, the acoustic coupler can include an outer protrusion, bump or raised portion on the outer surface. As described above, acoustic coupler may include a spherical cap-shaped protrusion which is configured to contact the skin of the patient and can provide contact between the skin and the acoustic coupler. Acoustic vibrations from the skin will be incident on the portion, travel through the acoustic coupler to the coupling bump and eventually be incident on the sensing elements held in tension by the bump. In addition, the contact portion may, in conjunction with the coupling elements or on its own, also help to improve the coupling between the skin and the sensing element. For example, when pressed against the skin, the contact portion may push a portion of the inner surface of the coupler, such as the coupling elements, into the sensing element, advantageously holding the sensing elements in tension. In an embodiment, the contact portion of the illustrated embodiment includes a semi-cylindrical bump mounted generally underneath the coupling element. The acoustic coupler may act to evenly distribute pressure to the sensing elements during use. For example, because the coupling element and the bump portion are generally positioned such that they are centered with respect to surface of the sensing element, pressure will be distributed symmetrically and/or evenly across the sensing element.

In certain embodiments, portions of the sensor assembly such as, for example, the acoustic coupler may include a gel or gel-like material. The gel may provide beneficial acoustic transmission, for example, serving to enhance the coupling between the acoustic vibrations from the patient's skin and the sensing element. The gel may provide acoustic impedance matching, for example, between the skin and the sensor. For example, the gel may serve to reduce the impedance mismatch from potential skin-to-air and air-to-sensing element discontinuity, thereby reducing potential reflections and signal loss. The gel may be embedded in a portion of the acoustic coupler. For example, one or more of the coupling elements and the contact portion may include a gel or gel-like material. The acoustic coupler may include an embedded gel in certain embodiments where one or more of the coupling element and the contact portion are not included. For example, the entire patient contact portion of the acoustic coupler may include gel material extending substantially from the patient contact surface to the interior of the coupler across the contact portion. One or more columns of gel material may extend from the patient contact surface of the coupler to the interior of the coupler in other embodiments. In yet further embodiments, the gel is not embedded in the acoustic coupler but is added to the skin directly. In one embodiment, the gel is embedded in the acoustic coupler and is configured to be released from the coupler when the sensor assembly is applied to the patient. For example, gel can be filled in one or more cavities of the acoustic coupler prior to use wherein the cavities are configured to open and release the gel when the coupler is pressed against the skin.

In various embodiments, the components of the sensor, and/or one or more sub-assemblies of the sensor, may be arranged differently. For example, the components may be combined such that the overall assembly includes fewer discrete components, simplifying manufacturability.

In an embodiment, the acoustic coupler is made of an elastomer and/or a thermoplastic elastomer.

Printed Circuit Board

The PCB includes various electronic components mounted to either or both faces of the PCB. When sensor assembly is assembled and the PCB is disposed in the upper portion of the sensor sub-assembly. To reduce space requirements and to prevent the electronic components from adversely affecting operation of the sensor assembly, the electronic components can be low-profile, surface mounted devices. The electronic components are often connected to the PCB using conventional soldering techniques, for example the flip-chip soldering technique. Flip-chip soldering uses small solder bumps such of predictable depth to control the profile of the soldered electronic components.

In some embodiments, the electronic components include filters, amplifiers, etc. for pre-processing or processing a low amplitude electric signal received from the sensing elements (e.g., the operational amplifiers discussed above with respect to the Faraday cage) prior to transmission through a cable to a physiological monitor. In other embodiments, the electronic components include a processor or pre-processor to process electric signals. Such electronic components may include, for example, analog-to-digital converters for converting the electric signal to a digital signal and a central processing unit for analyzing the resulting digital signal.

In other embodiments, the PCB includes a frequency modulation circuit having an inductor, capacitor and oscillator, such as that disclosed in U.S. Pat. No. 6,661,161, which is incorporated by reference herein. In another embodiment, the PCB includes an FET transistor and a DC-DC converter or isolation transformer and phototransistor. Diodes and capacitors may also be provided. In yet another embodiment, the PCB includes a pulse width modulation circuit.

In one embodiment, the PCB also includes a wireless transmitter, thereby eliminating mechanical connectors and cables. For example, optical transmission via at least one optic fiber or radio frequency (RF) transmission is implemented in other embodiments. In other embodiments, the sensor assembly includes an information element which can determine compatibility between the sensor assembly and the physiological monitor to which it is attached and provide other functions, as described below.

Information Element

In addition, the sensor assembly can include any of a variety of information elements, such as readable and/or writable memories. Information elements can be used to keep track of device usage, manufacturing information, duration of sensor usage, compatibility information, calibration information, identification information, other sensor, physiological monitor, and/or patient statistics, etc. The information element can communicate such information to a physiological monitor. For example, in one embodiment, the information element identifies the manufacturer, lot number, expiration date, and/or other manufacturing information. In another embodiment, the information element includes calibration information regarding the multi-parameter sensor. Information from the information element is provided to the physiological monitor according to any communication protocol known to those of skill in the art. For example, in one embodiment, information is communicated according to an I$^2$C protocol. The information element may be provided on or be in electrical communication with the PCB. In various embodiments, the information element can be located in another portion of the sensor assembly. For example, in one embodiment, the information element is provided on a cable connected to the PCB. The information element may further be located on the sensor connector, the attachment sub-assembly, the sensor sub-assembly, or some other part of the sensor assembly.

The information element can include one or more of a wide variety of memory devices known to an artisan from the disclosure herein, including an EPROM, an EEPROM, a flash memory, a combination of the same or the like. The information element can include a read-only device such as a ROM, a read and write device such as a RAM, combinations of the same, or the like. The remainder of the present disclosure will refer to such combination as simply EPROM for ease of disclosure; however, an artisan will recognize from the disclosure herein that the information element can include the ROM, the RAM, single wire memories, combinations, or the like.

The information element can advantageously store some or all of a wide variety data and information, including, for example, information on the type or operation of the sensor, type of patient or body tissue, buyer or manufacturer information, sensor characteristics including calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In some embodiments, the information element can be used to provide a quality control function. For example, the information element may provide sensor identification information to the system which the system uses to determine whether the sensor is compatible with the system.

In an advantageous embodiment, the monitor reads the information element on the sensor to determine one, some or all of a wide variety of data and information, including, for example, information on the type or operation of the sensor, a type of patient, type or identification of sensor buyer, sensor manufacturer information, sensor characteristics including history of the sensor temperature, the parameters it is intended to measure, calibration data, software such as scripts, executable code, or the like, sensor electronic elements, whether it is a disposable, reusable, or multi-site partially reusable, partially disposable sensor, whether it is an adhesive or non-adhesive sensor, sensor life data indicating whether some or all sensor components have expired and should be replaced, encryption information, keys, indexes to keys or has functions, or the like monitor or algorithm upgrade instructions or data, some or all of parameter equations, information about the patient, age, sex, medications, and other information that can be useful for the accuracy or alarm settings and sensitivities, trend history, alarm history, sensor life, or the like.

Various other examples and details of the monitor and cable connections, the sensor frame, the cavity, the locking posts, the sensing elements, the bonding and/or adhesive layers, the electrical noise shielding barrier, the acoustic coupler, and/or the printed circuit board may be found in, for example, the '939 application, including, without limitation, FIGS. 19A-19F (and the associated description) of the '939 application which are incorporated by reference herein.

Noise Compensation Overview

Embodiments of systems generally including at least first and second acoustic sensing elements and configured to provide noise compensation will now be described with respect to FIGS. 7-9D. As is described, according to some aspects, one of the sensing elements is used as a physiological signal sensing element, and another is used as a noise sensing element for generating a noise reference signal. The noise reference signal can be used to generate a physiological signal having a reduced noise component according to a variety of techniques described in further detail herein (e.g., adaptive filtering techniques). Moreover, according yet other embodiments, the sensing elements are selectively configurable for use as either physiological signal sensing elements or noise sensing elements, as desired, as described in further detail herein.

According to various aspects, the multiple acoustic sensing elements can be beneficially arranged in a variety of configurations. For example, the first and second sensing elements can be incorporated into the same sensor package, for example, as shown in the embodiment illustrated in FIG. 8. In some embodiments, the first and second sensing elements are included in separate sensor packages, or can otherwise be strategically positioned at a variety of locations in the monitoring environment. For example, such sensors can be positioned at multiple locations on the patient, as is shown in and described with respect to FIG. 9A. Moreover, one or more sensing elements can be positioned at the physiological monitor or some other appropriate location in monitoring environment, as is disclosed in FIG. 9B and the accompanying text.

Generally speaking, the interfering noise signals described herein (e.g., with respect to FIGS. 7-9D) can include any acoustic signal, and can include vibrational, sonic, infrasonic, or ultrasonic waves. Such signals can be transmitted in gases, liquids and/or solids. For example, depending on the physiological signal being monitored, the interfering noise can include patient sounds generated from physiological processes, such as breathing sounds, heart sounds, digestive sounds, combinations of the same and the like. Interfering noise can further include speech sounds, snoring, coughing, gasping, etc., and can emanate from the patient or other individuals in the monitoring environment. Further sources of noise can also include humming or other acoustic noise coming from computers or other electronic equipment in the operating environment, ambient traffic or airplane noise, combinations thereof and the like.

Interfering noise can additionally emanate from one or more noisy devices that are coupled to the patient, such as medical devices that are coupled to the patient during use. Examples of such devices can include, without limitation, powered surgical equipment (e.g., electrosurgical tools for cauterizing, coagulating, welding, cutting, etc.), ventilation equipment (e.g., continuous positive airway pressure (CPAP) machines), nebulizers, combinations of the same and the like.

Particularly where a noise source is readily identifiable, the noise sensing element according to certain aspects may be positioned in physical proximity to the noise source, so as to obtain a signal including a relatively clean noise reference signal, allowing for improved noise compensation according to techniques described herein. Specific example cases are provided below with respect to FIGS. 9A-9B, for example.

According to yet other described embodiments, it can be expected that the components of their output signals resulting from one source (e.g., the patient's body) will be generally similar while signal components from other sources (e.g., noise components) can be expected to have certain dissimilarities (e.g., phase or time shift). In these cases, the output signals from the first and second acoustic sensing elements can be advantageously combined in ways that accentuate commonalities between the two signals while attenuating differences between the two output signals, or vice versa, producing a reduced noise output signal.

Moreover, while shown and described as first and second sensing elements with respect to many of the embodiments described below, there may be more than two (e.g., 3, 4, 5 or more) sensing elements in certain embodiments. Additionally, while described as individual sensing elements for the purposes of illustration, in certain embodiments one or more of the first and second sensing elements each include multiple acoustic transducers or other types of sensing elements. In some embodiments, for example, the first and/or second sensing elements each include at least two piezoelectric films arranged in a stacked configuration, and may be wrapped around a support frame, as described above with respect to FIGS. 3B-5E, 6J-6M, and 12I-12K.

Figure 7:
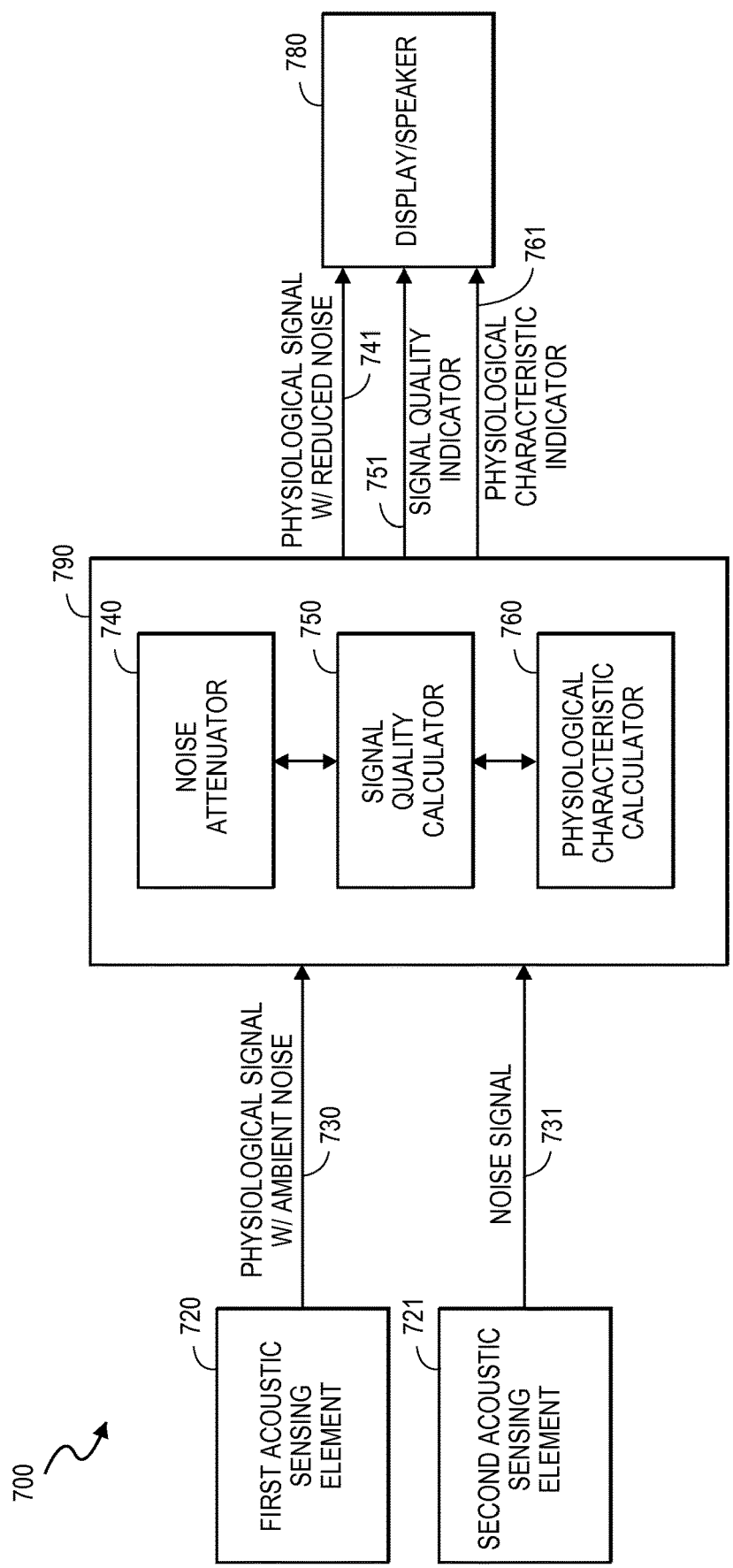
FIG. 7 is a block diagram of an example acoustic physiological monitoring system having noise compensation features.

FIG. 7 is a block diagram of an embodiment of an acoustic physiological monitoring system 700 having noise compensation features. The noise compensation features can be useful for reducing any deleterious effect of acoustic noise on the accuracy of physiological characteristics determined using the monitoring system 700.

The acoustic physiological monitoring system 700 includes a first acoustic sensing element 720 and a second acoustic sensing element 721. In some embodiments, these acoustic sensing elements are passive devices. In some embodiments, the first acoustic sensing element 720 is used to produce a physiological signal 730 that is indicative of one or more physiological sounds (e.g., sounds resulting from physiological processes) emanating from a patient's body. For example, the first acoustic sensing element 720 may be used to produce a physiological signal 730 that is indicative of a particular type of physiological sound, which is sometimes referred to herein as the target physiological sound. A variety of target physiological sounds are possible, including breathing sounds, heart sounds, digestive sounds, and the like. For example, the sensing elements 720, 721 can be piezoelectric films. In general, this physiological signal 730 can include unwanted noise as a result of interfering noise in the patient's surroundings being picked up by the first acoustic sensing element 720. The physiological component and the noise component of the signal 730 can overlap in time and/or frequency content. Devices for detecting primarily physiological sounds emanating from the patient's body are disclosed more fully herein.

In some embodiments, the second acoustic sensing element 721 is used to produce a noise signal that is substantially representative of, or otherwise meaningfully correlated with, any noise picked up by the first acoustic sensing element 720. The noise signal 731 may not necessarily duplicate the noise component of the physiological signal 730. For example, the signal strength of the noise in the two signals 730, 731 can differ. Other differences between the noise signal 731 and the noise component of the physiological signal 730 are also possible. However, it can be advantageous for the second acoustic sensing element to be positioned and designed such that the noise signal 731 has some degree of commonality with the noise present in the physiological signal 730. In this way, the noise signal 731 can provide useful information to meaningfully reduce, remove, filter, cancel, separate out, etc. the noise from the physiological signal 730. Devices for detecting primarily noise sounds are disclosed more fully herein.

In addition, the second acoustic sensing element 721 can also be positioned and designed such that the noise signal 731 is substantially free of the physiological sounds picked up by the first acoustic sensing element 720, or such that such physiological sounds are a less-significant component of the noise signal 731 than they are of the physiological signal 730. While illustrated as producing a noise signal 731, in other embodiments discussed more fully herein the second acoustic sensing element is positioned and designed to provide a second physiological signal rather than a noise reference signal. For example, like the first sensing element 720, the second acoustic sensing element 721 may include both a significant physiological signal component and an interfering noise component. In such embodiments, the first and second physiological signals can be combined in certain ways so as to reinforce the physiological components of the two signals while reducing any noise components that can exist in the two physiological components. In other embodiments, this can be carried out using more than two acoustic sensing elements.

In some embodiments, the physiological signal mixed with noise 730 and the noise signal 731 are input to a processing unit 790. In some embodiments, the processing unit 790 includes a noise attenuator 740, a signal quality calculator 750, and a physiological characteristic calculator 760. The processing unit 790 can be implemented as one or more digital signal processors, one or more analog electric processing components, combinations of the same or the like, etc.

In some embodiments, the noise attenuator 740 reduces the amount of noise present in the physiological signal 730 based on information gleaned from the noise signal 731, as discussed in more detail herein. For example, the noise attenuator 740 can reduce the signal energy of the noise component of the physiological signal 730. Alternatively, or in addition, the noise attenuator 740 can reduce or remove a portion of the noise component of the physiological signal 730 over a particular frequency range. In some embodiments, the processing unit 790 outputs a physiological signal with reduced noise 741 using the noise attenuator 740. The signal 741 can also be provided to other sub-blocks of the processing unit 790 (e.g., the physiological characteristic calculator 760).

The signal quality calculator 750 is a device that is used to determine, for example, an objective indicator of the quality of the physiological information obtained from one or more acoustic sensing elements. This can be done, for example, by comparing the physiological signal 730 with the noise signal 731, as discussed further herein. The signal quality calculator 750 can also output an objective indicator of the degree of confidence in the accuracy of a physiological characteristic (e.g., respiratory rate) determined based on the physiological information collected from one or more acoustic sensors. The signal quality calculator 750 can also output a binary confidence indicator that selectively indicates low confidence and/or high confidence in the accuracy of the physiological characteristic. The processing unit 790 then outputs one or more signal quality indicators 751.

The physiological characteristic calculator 760 is used to determine, for example, one or more values or signals that are indicative of a physiological characteristic of the patient. For example, the physiological characteristic can be respiratory rate, expiratory flow, tidal volume, minute volume, apnea duration, breath sounds, riles, ronchi, stridor, and changes in breath sounds such as decreased volume or change in airflow. In some embodiments, a physiological characteristic is calculated using a processing algorithm applied to the physiological signal with reduced noise 741 that is outputted by the noise attenuator 740.

The physiological signal with reduced noise 741, the signal quality indicator 751, and the physiological characteristic indicator can be output to a display and/or speaker 780 to be viewed or heard by a caregiver. For example, in some embodiments, the physiological signal with reduced noise 741 is converted back to an audible sound by way of a speaker or other acoustic transducer so that it can be heard by a doctor and used for diagnosis of the patient. In some embodiments, the signal quality indicator 751 and the physiological characteristic indicator 761 are displayed on a screen. This information can take the form of a numerical value, a plotted signal, an icon, etc.

Although both the noise attenuator 740 and the signal quality calculator 750 are included in the example processing unit 790 shown, the processing unit 790 could include either the noise attenuator 740 or the signal quality calculator 750 in some embodiments.

In various embodiments, the first and second acoustic sensing elements 720, 721 can be either the same or different types of acoustic sensing elements. For example, in one embodiment, both of the sensing elements are piezoelectric films such as any of the films described herein. In such a configuration, each of the sensing elements 720, 721 may be housed in a separate sensor packaging. As an example where different types of sensing elements are used, the first sensing element 720 in one embodiment is a piezoelectric film, while the second sensing element is a microphone, vibrational sensor or other type of acoustic pickup device. Such an embodiment is described with respect to FIG. 15 below.

Additionally, the sensing elements 720, 721 may be physically separate from one another. For example, the sensing elements 720, 721 can be physically separated within a single wearable sensor package. In other embodiments, the first sensing element 720 may be located on a wearable sensor package, such as any of those described herein, while the second sensing element 721 may be located at some other location, such as, for example, on a cable, hub, monitor, or in another wearable sensor package at a different location on the patient, etc. Further embodiments of sensors including physically separate sensing elements are discussed herein, with respect to FIGS. 8-9B, for example.

While embodiments described herein advantageously employ multiple sensing elements to achieve noise compensation, in certain embodiments, noise compensation is achieved using a single sensing element. For example, the sensing element may be coupled to the patient and thus produce a signal including both physiological and noise components. However, in such embodiments, the noise reference signal may be extracted during periods when the physiological signal is inactive (e.g., in between patient breaths, heart beats, etc.). The extracted reference signal can then be used in accordance with techniques described herein to provide noise compensation.

Figure 8:
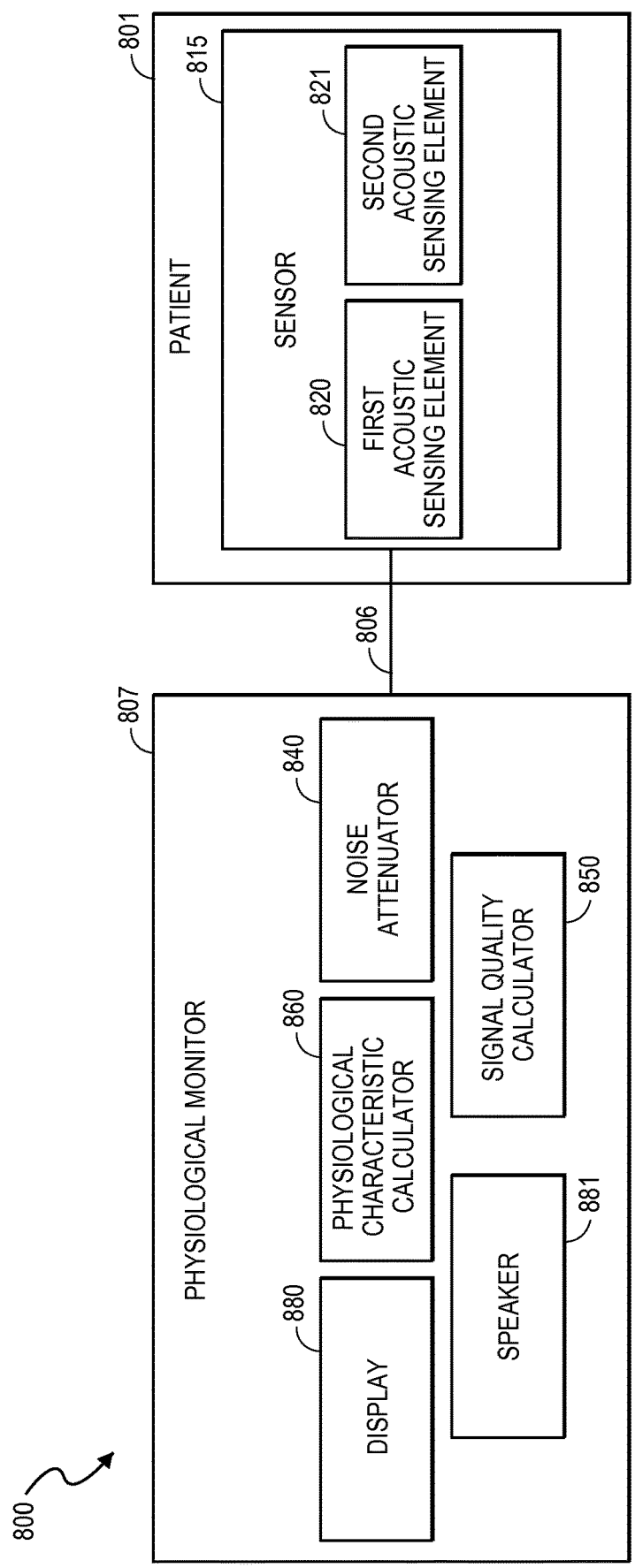
FIG. 8 is a block diagram of an embodiment of an acoustic physiological monitoring system with an acoustic sensor that includes first and second acoustic sensing elements.

FIG. 8 is a block diagram of an embodiment of an acoustic physiological monitoring system 800 with a wearable acoustic sensor 815 that includes first and second acoustic sensing elements 820, 821. The first and second acoustic sensing elements 820, 821 are, for example, transducers for converting sound waves into some other form of energy (e.g., electrical voltage or current signals) to be processed, measured, etc. The first and second acoustic sensing elements 820, 821 can be packaged in a common housing as shown in FIG. 8, or in separate housings, as shown in FIG. 9A, described below. In some embodiments, the first and second acoustic sensing elements 820, 821 are both the same type of acoustic transducer. For example, in some embodiments, the first and second acoustic sensing elements 820, 821 are both piezoelectric films.

Even in cases where the first and second acoustic sensing elements 820, 821 are generally the same type of acoustic transducer, they need not be identical. For example, in the case where both of the first and second acoustic sensing elements 820, 821 are piezoelectric films, the material properties of the two films can be separately adapted based on known characteristics of the aural signals they are intended to sense. The first and second acoustic sensing elements 820, 821 can be made of different piezoelectric materials, they can have different shapes and thicknesses, they can have different support/mounting structures, and they can have different packaging. For example, in a given application (e.g., a medical sensing application), system designers can have foreknowledge regarding the characteristics of the sought-after acoustic signals.

As described herein, in some embodiments, the first acoustic sensing element 820 is used to primarily sense physiological signals, while the second acoustic sensing element 821 is used primarily to sense noise. In such cases, the type of piezoelectric material, and its shape, thickness, its mounting and packaging, etc. can be adapted for each of the acoustic sensing elements 820, 821 based on unique characteristics (e.g., frequency range, amplitude, etc.) of the physiological signals and the expected noise, respectively, if such unique characteristics exist and are identifiable.

In other embodiments, it is advantageous for the properties (e.g., material properties, mounting, packaging, etc.) of the first and second acoustic sensing elements 820, 821 to be substantially similar or even identical. This can be the case, for example, where the acoustic signals to be sensed by the two acoustic sensing elements 820, 821 have no important pre-identifiable differing characteristics.

It can also be advantageous for the first and second acoustic sensing elements 820, 821 to be substantially similar or even identical in terms of material properties, mounting, and packaging so that their signal outputs will likewise have shared characteristics in response to excitation of the acoustic sensing elements by a common source. This can be the case where the outputs of the first and second acoustic sensing elements 820, 821 are to be combined using techniques for selecting or rejecting signal components from the two sensing element outputs based on their common or distinguishing features. Examples of such techniques are described in further detail herein.

In other embodiments, the first and second acoustic sensing elements 820, 821 are different types of acoustic transducers. For example, the first and second acoustic sensing elements 820, 821 can be independently selected from a group including, but not limited to, piezoelectric acoustic transducers, condenser acoustic transducers, MEMS acoustic transducers, and electromagnetic induction acoustic transducers. Other types of acoustic transducers can also be used.

The first and second acoustic sensing elements 820, 821 can exhibit directionality or not. In cases where both of the first and second acoustic sensing elements 820, 821 exhibit directionality, they can be aimed at a common location (e.g., the patient's skin) or a different location (e.g., the first acoustic sensing element 820 could be aimed at the patient's skin to detect physiological sounds, while the second acoustic sensing element could be directed away from the patient's skin so as to detect ambient noise). In addition, in some embodiments, one of the acoustic sensing elements can exhibit directionality while the other does not. For example, in some embodiments the first acoustic sensing element 820 can exhibit directionality and be aimed at the patient's skin for detecting physiological sounds, while the second acoustic sensing element 821 does not exhibit directionality so as to detect noise from all directions.

As described herein (e.g., with respect to acoustic sensor 201), the acoustic sensor 815 can include a cable 806, or other communication link, for communicating with a physiological monitor 807. For example, one or more connectors, hubs, or other cables may be included as described herein. The acoustic sensor can also include one or more devices (e.g., electrical circuits) for detecting, processing, and transmitting the outputs from the first and second acoustic sensing elements 820, 821. The sensor can also include a fastener for fastening the sensor to the body of a patient. In some embodiments, the fastener is specially adapted to attach to the patient's neck or chest region in order to sense breathing sounds. The acoustic sensor 815 can also include other features described with respect to acoustic sensor 201.

In some embodiments, the acoustic sensor 815 is adapted to be communicatively coupled with a separate physiological monitor 807 that is not worn by the patient 801. (The physiological monitor 807 can include, for example, a display 880, a physiological characteristic calculator 860, a noise attenuator 840, a speaker 881, and a signal quality calculator 850, as described herein.) Thus, in some embodiments, the first and second acoustic sensing elements 820, 821 are disposed on or in an acoustic sensor 815 that is adapted to be worn by the patient 801, while the signal outputs from the first and second acoustic sensing elements 820, 821, which can include the raw signals directly from the acoustic sensing elements 820, 821 as well as processed signals derived therefrom, are transmitted to a separate physiological monitor 807 that is not worn by the patient 801. In other embodiments, however, the acoustic sensor 815 and the physiological monitor 807 can both be wearable by the patient 801.

As discussed herein, in some embodiments the first acoustic sensing element 820 is designed and used primarily to sense an acoustic physiological signal emanating from a patient's body, while the second acoustic sensing element 821 is used primarily to sense the acoustic noise. The first acoustic sensing element 820 can, however, also detect acoustic noise. In this case, the noise signal from the second acoustic sensing element 821 can be used as a noise reference to yield information that can be used to reduce or remove the presence of the acoustic noise from the physiological signal at the output of the first acoustic sensing element 820.

In cases where the second acoustic sensing element 821 is used to produce a noise reference signal, it can be advantageous for the first and second acoustic sensing elements 820, 821 to be designed and positioned with respect to one another such that the noise reference signal produced by the second acoustic sensing element 821 shares one or more characteristics with the noise component of the physiological signal output by the first acoustic sensing element. For example, the noise reference signal can be meaningfully correlated with the noise component of the physiological signal. In some embodiments, the noise reference signal from the second acoustic sensing element 821 and the noise component of the physiological signal from the first acoustic sensing element 820 are related by, for example, a scalar factor, a time shift, a phase shift, or combinations of the same. Other relationships between the noise reference signal and the noise component of the physiological signal are also possible.

In some embodiments, clinically meaningful correlation between the noise reference signal and the noise component of the physiological signal is achieved, at least in part, by placing the first and second acoustic sensing elements 820, 821 in proximity to one another. For example, as illustrated in FIG. 8, the first and second acoustic sensing elements 820, 821 can be commonly located on a wearable acoustic sensor 815. Disposing the first and second acoustic sensing elements 820, 821 in proximity to one another can improve correlation between the noise reference signal and the noise component of the physiological signal by reducing differences in, for example, the amplitude, frequency content, and phase between the noise sensed at the first acoustic sensing element 820 as compared to the noise sensed at the second acoustic sensing element 821.

The physical distance between the first and second acoustic sensing elements 820, 821 can vary from embodiment to embodiment depending upon, for example, the expected frequency content of the noise, the presence of acoustically dispersive materials, acoustic reflectors or absorbers, or the like, that are located, for example, between the two sensing elements. For example, a physiological monitoring system 800 operated in an environment with relatively lower frequency noise (e.g., ambient noise) can be able to tolerate larger physical distances between the first and second acoustic sensing elements since such distances will be smaller relative to the wavelength of the noise than in the case of noise with higher frequency content. Thus, even despite a relatively larger physical separation between the first and second acoustic sensing elements, the noise sensed by the second acoustic sensing element can still be reasonably indicative of, or related to, the noise sensed by the first acoustic sensing element.

In some embodiments, the actual tolerable physical distance between the first and second acoustic sensing elements 820, 821 can depend upon the particular application and/or noise-reducing requirements imposed by the application. In some embodiments, the first and second acoustic sensing elements 820, 821 can be physically disposed in close enough proximity to one another such that an noise reference signal detected by the second acoustic sensing element 821 contains a sufficient amount of information regarding the noise component of the physiological signal detected by the first acoustic sensing element 820 so as to provide a clinically significant reduction in the noise component of the physiological signal. This can be manifested, for example, by a clinically significant improvement in the accuracy of a physiological characteristic (e.g., respiratory rate) determined by the physiological monitoring system from a noise-reduced version of the physiological signal detected by the first acoustic sensing element 820.

In some embodiments, the first and second acoustic sensing elements are physically located within a 1 m radius of one another. In some embodiments the first and second acoustic sensing elements are physically located within a 0.1 m radius of one another. In some embodiments the first and second acoustic sensing elements are physically located within a 0.01 m radius of one another. In some embodiments the first and second acoustic sensing elements are physically located within a 0.001 m radius of one another.

In some embodiments, the first and second sensing elements 820, 821 can be disposed in separate sensor packages or otherwise be disposed at different locations throughout the operating environment. For example, FIG. 9A is a block diagram of an embodiment of an acoustic physiological monitoring system 900 with first and second acoustic sensing elements 920, 921 disposed in or otherwise being associated with separate first and second sensors 916, 917. While shown as being coupled to the physiological monitor 907 via a single communication link 906, a separate communication link 906 may be used for each sensor 916, 917 in certain embodiments. In some embodiments, each communication link 906 includes one or more cables, hubs, and/or connectors as described herein. FIG. 9B is a block diagram including a first sensing element 920 disposed on a patient and a second sensing elements 920, 921 disposed on a physiological monitor 907.

Referring to FIG. 9A, the first and second sensors 816, 817 can be positioned at a variety of locations on the patient 901. For example, in certain embodiments, one or both of the sensing elements 920, 921 (and their associated sensors 916, 917) can be positioned on or around sources of sounds generated by physiological processes. Such areas can include those associated respiratory or vocal sounds including for example, the throat, back of the neck, mouth, or some other portion of the head or neck, on the back or chest around the lungs, combinations of the same and the like. Other sensing element locations can include those generally associated with heart sounds, such as on the chest around the heart, on the throat, on the wrist, etc. Yet other locations can include those typically associated with digestive sounds such as near the stomach or on some other portion of the abdomen. Moreover, while the above examples are provided for the purposes of illustration, depending on the application, the sensors 916, 917 can additionally be positioned at generally any location on the patient's body 901 including, for example, a hand, finger, arm, foot, leg, etc.

Figures 9C, 9D:
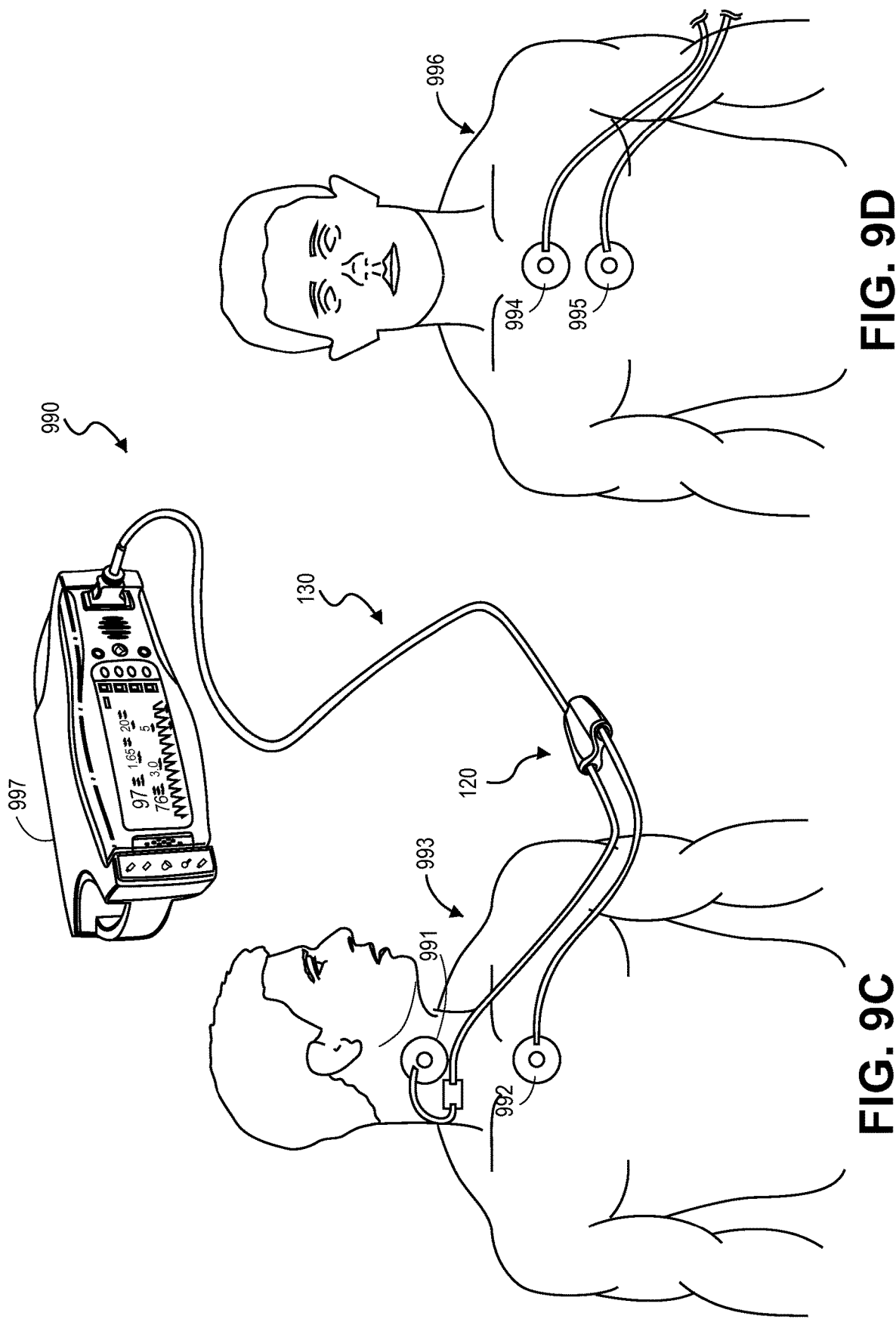
FIGS. 9C-9D illustrate example systems including dual acoustic sensors applied to a patient according to certain embodiments.

FIG. 9C illustrates an example system 990 including dual acoustic sensors 991, 992 applied to a patient's 993 throat and chest, respectively. FIG. 9D illustrates a second example where sensors 994, 995 are applied to different regions of a patient's 996 chest. The dual acoustic sensors 991, 992, 994, 995 can be coupled to a physiological monitor 997 via a hub and a plurality of cables, as shown. The sensors 991, 992, 994, 995, monitor 997, cables, hub, etc., can be any of those described herein or incorporated by reference, or can be some other acoustic sensors. The system 990 of FIG. 9C depicts one example embodiment where the dual sensor cable 130 can connect to multiple sensors using the junction 120. Where multiple sensors are attached to the patient or are otherwise spatially separated throughout the operating environment, such an arrangement may be referred to as a stereo monitoring environment that allows for stereo body sound monitoring.

The sensing elements 920, 921 and, where present, associated sensor packages, can additionally be positioned at one or more locations in the operating environment not on the patient's body. For example, FIG. 9B is a block diagram of an embodiment of an acoustic physiological monitoring system 902 with a wearable acoustic sensor 915 that includes a first acoustic sensing element 920, and a physiological monitor unit 907 that includes a second acoustic sensing element 921. The physiological monitor unit 907 is adapted to be communicatively coupled with the wearable acoustic sensor 915 via, for example, a cable 906. In some embodiments, the physiological monitor unit 907 is a non-wearable unit with one or more devices for processing signal outputs from the first and second acoustic sensing elements 920, 921. The physiological monitoring system 902 of FIG. 9B is similar to the physiological monitoring systems 800, 900 except that the second acoustic sensing element 921 is physically located at the non-wearable physiological monitor 907 instead of at the wearable acoustic sensor 915.

While shown on the monitor 907, the second sensing element 921 can be positioned at a variety of other locations. For example, in cases where the physiological monitor 907 and the acoustic sensor 915 are communicatively coupled using a physical cable 906, the cable 906 can be useful in placing a limit on the distance between the first and second acoustic sensing elements 920, 921 to ensure that they remain in close enough proximity with one another to provide for meaningful noise reduction for a given medical sensing application. In other embodiments, the second acoustic sensing element 921 can be at any intermediate location between the monitor and the sensor, such as on or in the cable 906, a connector, a junction, or a hub (not shown) such as the junction 120 of FIG. 1C, or generally at any separate location independent of the physiological monitor 907 or the acoustic sensor 915. Where the second sensing element 921 is used to generate a noise reference, positioning the second sensing element 921 on or in the monitor 907, junction, or at another intermediate location, rather than on the sensor 915 can advantageously reduce the wiring overhead in the system. On the other hand, it can be beneficial to locate the second sensing element 921 near the first sensing element 920 so as to generate a noise reference signal that is substantially correlated with the noise component of the signal detected by the first sensing element 920. Thus, in certain cases, a trade off generally exists between locating the second sensing element 921 in proximity to the first sensing element 920 to improve noise rejection on the one hand, and locating the second sensing element remote from the first sensing element 920 to reduce wiring overhead on the other. Thus, in circumstances, locating the second sensing element 921 at the junction or at another intermediate location between the monitor 907 and the first sensing element 920 provides the desired balance between reduced wiring overhead and adequate noise rejection.

As mentioned, where a noise source is readily identifiable, the second sensing element 921 can be positioned in physical proximity to the noise source. In this manner, the second sensing element 921 can be used to produce a signal including a relatively clean noise reference signal, allowing for improved noise compensation. Such noise sources can be those generating any of the interfering noise described herein such as non-target physiological sounds emanating from the patient (e.g., heart, breathing or digestive sounds), ambient noise (e.g., traffic, ambient speech sounds, computer humming, and the like), or vibrations or other noise emanating from skin-coupled devices (e.g., electrosurgical devices, CPAP machines, nebulizers, etc.).

Several example scenarios incorporating multiple sensing elements 920, 921 strategically located at separate locations in the operating environment will now be described. These examples are provided for the purposes of illustration, and are not intended to be limiting. As a first illustrative example, referring to FIG. 9A, the first sensor 916 is a physiological signal sensor and is positioned on or around a source of breathing sounds (e.g., the neck), while the second sensor 917 is a noise sensor and is positioned on or around the heart to detect heart sounds and/or other noise components. Thus, the signal from the second sensor 917 can be used to cancel or otherwise attenuate any residual heart sounds (and/or ambient or other noise) that may bleed into the signal produced by the first sensor 916.

In another example scenario, a CPAP machine or other medical device is coupled to the patient. The first sensor 916 is a physiological signal sensor positioned on the patient's heart to detect heart sounds, and the second sensor 917 is a noise sensor positioned on the CPAP machine or other medical device. Thus, the signal produced by the second sensor 917 can be used to cancel any residual noise from the CPAP machine (and/or ambient or other noise) that bleeds into the signal detected by the first sensor 916.

In yet another illustrative example, the first sensor 916 is a physiological signal sensor positioned to detect breathing sounds, and the second sensor 917 is a noise sensor positioned on the patient near a planned electrosurgical site (or on an electrosurgical device itself). The second sensor 917 can be used in such a situation to cancel noise generated by the electrosurgical device (and/or ambient or other noise) that bleeds into the signal detected by the first sensor 916.

Selective Configuration of Multiple Sensing Elements

Depending on the desired application, the multiple sensing elements can be selectively configured in a plurality of modes. For example, referring still to FIGS. 9A-9B, the sensing elements 920, 921 can be configured as either physiological signal sensors or noise sensors in some embodiments. In addition to physiological sensing and noise modes, the sensing elements can be configured in a variety of other modes. For example, in one embodiment, one or more of the sensing elements 920, 921 is configurable in an auscultation mode. For example, the sensing elements 920, 921 can be configured in a listening mode in which an operator can generally continuously listen to audio output indicative of patient bodily or voice sounds. In yet another embodiment, the sensing elements 920, 921 can be configured to sense and process ultrasonic signals (e.g., for ultrasonic imaging). Examples of sensors capable of various types of audio output, ultrasonic sensing, and other compatible functionality are provided in U.S. patent application Ser. No. 12/905,036, entitled PHYSIOLOGICAL ACOUSTIC MONITORING SYSTEM, filed on Oct. 14, 2010, incorporated by reference herein in its entirety.

As one example, the first sensor 916 is positioned on or around a source of breathing sounds (e.g., on the throat), while the second sensor 917 is positioned on or around the heart to detect heart sounds. In a first mode, the first sensor 916 is configured in a physiological sensing mode and the second sensor 917 is configured in a noise sensing mode, while in a second mode, the roles of the sensors are generally switched. In this manner, breathing sounds are monitored and the effect of heart sounds (and/or other noise) is reduced according to noise cancelling techniques described herein. Moreover, in the second mode, heart sounds are monitored, and the effect of any residual breathing sounds (and/or other noise) is reduced. Thus, according to such techniques, a user can flexibly and efficiently switch between monitoring reduced noise versions of a wide variety of physiological signals.

Moreover, the sensing elements can be configured for use in more than one mode at a time in certain embodiments. For example, each of the sensing elements 920, 921 can be configured simultaneously as both physiological signal sensing elements and noise sensing elements. In the above example scenario, the first sensing element 920 can be used to monitor breathing sounds and also generally simultaneously provide a noise reference to the second sensing element 921. Conversely, the second sensing element 921 can be used to monitor heart sounds and also generally simultaneously provide a noise reference to the first sensing element 920. While other modes are possible, in various embodiments, the sensing elements 920, 921 can be configured generally simultaneously for two or more of physiological signal sensing, noise sensing, auscultation, and ultrasonic sensing.

The configuration of the sensing elements 920, 921 may be manually selectable by a user, or can be automatically configurable by the system. For example, one or more user-actuatable inputs (e.g., buttons, switches, keypad inputs, etc.) may be provided to the user for setting the sensing element 920, 921 modes. Such inputs may be located on the monitor 907, in proximity to the sensing elements 920, 921 themselves, such as on the respective sensor packaging, or at some other appropriate location.

Moreover, the modes of the sensing elements 920, 921 can be configurable either as a group or individually in various embodiments. For example, referring to the above example where the first sensing element 920 is positioned to detect breathing sounds and a second sensing element 921 is positioned to detect heart sounds, the system may allow the user to select either of a breathing sound monitoring mode or a heart sound monitoring mode. Based on the selection, the system will appropriately automatically configure each sensing element 920, 921 mode. In another embodiment, the user sets each of the respective sensing element 920, 921 modes separately.

Where multiple sensing elements are present and are configured or selectively configurable for use as noise sensing elements, the system according to some embodiments automatically selects which sensing element or group thereof to use in the noise cancellation algorithm. Moreover, the outputs from multiple noise sensing elements or a selected combination thereof can be combined so as to provide improved noise rejection.

As one example, a first sensing element 920 is disposed on a wearable acoustic sensor 915 positioned on the patient's neck and is configured to receive a signal including physiological signal components and noise components. Second, third and fourth acoustic sensing elements are disposed on the cable, at the hub, and in the monitor, respectively, and are configured to receive noise signals.

In such embodiments, the physiological monitor 907 or other system component can generally use signals received from at least one of the noise acoustic sensing elements to perform noise reduction. For example, in the above example, each of the signals from the second, third and fourth sensing elements can be combined or otherwise used to perform noise compensation. In other cases, only a subset of one or more of the signals may be used as desired.

The system 900 can allow for manual selection of the noise acoustic sensing element(s) to use during monitoring, or can alternatively automatically select which of the noise acoustic sensors (e.g., the second third, or fourth sensing elements or a combination thereof) to use. Automatic selection can be performed in a variety of ways.

For example, in one embodiment, the system 900 evaluates the signals from each of the noise acoustic sensors, such as by assessing the magnitude or quality of the respective noise signals, and selects one or more of the signals to use based on the evaluation. For example, in some embodiments, the noise sensing element or combination of noise sensing elements that provides one or more of the highest amplitude noise reference signal or the cleanest noise reference signal is selected. In another embodiment, the system 900 assesses the degree of noise compensation achieved using the different noise acoustic sensing elements and/or combinations thereof, and selects the noise acoustic sensing element or combination thereof that provides the highest (or otherwise desirable) level of noise compensation to use during monitoring.

Noise Compensation Using Signal or Noise Correlation Between Sensing Elements

As described, it can be advantageous in certain embodiments for the first and second acoustic sensing elements to be substantially similar or even identical in terms of material properties, mounting, and packaging so that their signal outputs will likewise have shared characteristics in response to excitation of the acoustic sensing elements by a common source. This can be the case where the outputs of the first and second acoustic sensing elements are to be combined using techniques for selecting or rejecting signal components from the two sensing element outputs based on their common or distinguishing features.

For example, referring to FIGS. 9A-9B for the purposes of illustration, in some applications it can be expected that, owing to similarities in the design and placement of the first and second acoustic sensing elements 920, 921 or other factors, the components of their output signals resulting from a common source (e.g., the patient's body) will be generally similar while signal components from other sources (e.g., noise components) can be expected to have certain dissimilarities (e.g., phase or time shift). In these cases, the output signals from the first and second acoustic sensing elements 920, 921 can be combined in ways that accentuate commonalities between the two signals while attenuating differences between the two output signals.

In one example scenario, referring to FIG. 9A, the first and second acoustic sensing elements 920, 921 are substantially the same type and are included in separate sensor packages each placed on the patient. As described, the physiological signal components produced by the sensing elements 920, 921 are substantially correlated with respect to one another. In some cases, the correlation can be enhanced via strategic placement of the sensing elements 920, 921 with respect to one another. For example, the sensor packages can be placed generally symmetrically about the signal source (e.g., the throat or chest). In contrast, the noise signal components produced by the sensing elements 920, 921 are substantially uncorrelated with respect to one another.

In such a scenario, the components can be uncorrelated for a variety of reasons. For example, noise signals emanating from external sources may reflect off of the skin or sensor package before reaching the respective sensing element 920, 921. The signal may also propagate through a portion of the sensor package before reaching the respective sensing element 920, 921, causing additional distortions. Moreover, the degree and quality of distortion in the noise signal received by the sensing elements 920, 921 can differ significantly between the sensing elements 920, 921. For example, in addition to other possible reasons, the variation in distortion can be caused by a variation in the respective angle of arrival of the noise signal at each of the sensor packages. This can be due to the difference in the orientation of the noise source from one sensor package to another.

The output signals from the first and second acoustic sensing elements 920, 921 in such a scenario can be combined to accentuate the correlated physiological signal components and attenuate the uncorrelated noise components between the two output signals. For example, while a variety of techniques can be used, the outputs from the sensing elements are summed together in one embodiment. The correlated components will tend to additively combine, while the uncorrelated components will not, resulting in an overall improved SNR. In other embodiments, more than two (e.g., three, four, five or more) sensing elements 820, 821 are used.

In some other embodiments, certain noise components (e.g., ambient noise components) of the signals produced by the first and second sensing elements 920, 921 may be correlated, while the physiological signal components may be uncorrelated. In such cases, additional appropriate techniques can be used to generate a reduced noise signal. Examples of such techniques, including cross-correlation, are described in U.S. application Ser. No. 12/904,789, entitled ACOUSTIC RESPIRATORY MONITORING SYSTEMS AND METHODS, filed on Oct. 14, 2010, the entirety of which is incorporated by reference herein.

Various other example noise compensation embodiments that may be applied to the sensor embodiments of the present disclosure are described throughout the '939 application, including, without limitation, FIGS. 12-18 (and the associated description) of the '939 application which are incorporated by reference herein.

Electromagnetic Interference (EMI) Compensation

In some embodiments, the physiological monitoring systems and patient sensors described herein include electromagnetic interference compensation features. The electromagnetic interference compensation features can be useful for reducing any deleterious effect of EMI on the accuracy of physiological characteristics determined using the monitoring systems. One possible source of such EMI could be, for example, 50-60 Hz RF waves generated by the electric power distribution system in a patient care facility.

In some embodiments, the physiological monitoring systems include an electrical conductor for detecting an EMI reference signal that is indicative of EMI that may have corrupted electrical signals used by the physiological monitoring systems (e.g., a physiological signal generated by an acoustic sensing element). The EMI reference signal detector can be, for example, a dedicated antenna that is positioned at a location where the EMI that it detects is in some way representative of, or meaningfully correlated with, the EMI to which an electrical signal within the patient sensor is exposed. The EMI reference signal detector can be located, for example, on or in one or more wearable patient sensors (e.g., 215, 815, 915, etc.), though it may also be located in a separate physiological monitor unit, intermediate location (e.g., cable, connector, junction, or hub), at any location described above with respect to acoustic noise reference sensing elements, or at some other location.

In some embodiments, the EMI reference signal detector is a conductive plate or wire, or some other conductive structure. In some embodiments, the EMI reference signal detector is left electrically floating. While in some embodiments, the EMI reference signal detector is a dedicated component, in other embodiments other existing components of, for example, a patient sensor described herein can be used as the EMI reference signal detector. For example, one or more electrical shielding layers in a patient sensor can be used to detect EMI and to generate an EMI reference signal. Generally, according to certain aspects, any of the shielding barriers described herein (e.g., with respect to FIGS. 4A-5E, etc.) can be used to detect EMI and generate an EMI reference signal.

In some embodiments, the EMI reference signal generated by the EMI reference signal detector is transmitted to a noise attenuator or other sensing circuitry. The noise attenuator can also be communicatively coupled to, for example, one or more physiological electrical signals output from the acoustic sensing elements described herein. Such physiological electrical signals can be corrupted by any EMI to which they are exposed.

The noise attenuator or other sensing circuitry reduces or removes the EMI component from the physiological signal based on information regarding the EMI that is gleaned from the EMI reference signal. The noise attenuator or other sensing circuitry can use any of numerous methods and components for reducing, removing, filtering, canceling, subtracting, or separating out EMI in a signal based on the EMI reference signal, or combinations of the same or the like. For example, the noise attenuator may be an adaptive noise filter or an adaptive noise canceller. The noise attenuator can perform time domain and/or frequency domain operations. The noise attenuator can include time shift modules, phase shift modules, scalar and/or complex multiplier modules, filter modules, etc., each of which can be implemented using, for example, hardware (e.g., electrical components, FPGAs, ASICs, general-purpose digital signal processors, etc.) or a combination of hardware and software.

In some embodiments, the noise attenuator or other sensing circuitry includes a self-adjusting component whose effect on the physiological signal corrupted by EMI continuously varies in response to information derived from the EMI reference signal. For example, the self-adjusting component can be an adaptive filter whose transfer function, or some other characteristic, is iteratively updated based on analysis of the EMI reference signal. The adaptive filter can be implemented, for example, using a digital signal processor with iteratively updated filter coefficients. Other methods of implementing the adaptive filter can also be used. Filter coefficients can be updated using, for example, a least mean squares algorithm (LMS), or a least squares algorithm, a recursive least squares algorithm (RLS). The noise attenuator can also use, for example, a Kalman filter, a joint process estimator, an adaptive joint process estimator, a least-squares lattice joint process estimator, a least-squares lattice predictor, a noise canceler, a correlation canceller, optimized time or frequency domain implementations of any of the above, combinations of the same, and the like.

Terminology/Additional Embodiments

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A non-invasive acoustic sensor for outputting signals responsive to acoustic vibrations indicative of one or more physiological parameters of a patient, the acoustic sensor comprising:

a sensor support frame defining an acoustic cavity;

a piezoelectric acoustic sensing element at least partially supported by the sensor support frame, wherein at least a portion of the piezoelectric acoustic sensing is stretched in tension across the acoustic cavity, and wherein the piezoelectric acoustic sensing element is configured to output a first electrical signal responsive to acoustic vibrations of a patient;

a one piece integral shell that houses the sensor support frame and comprises:
- a bottom portion configured to contact the patient when the acoustic sensor is attached to the patient, the bottom portion having no openings and forming a barrier between the patient and the piezoelectric acoustic sensing element;
- a top portion opposite the bottom portion including at least one opening dimensioned to allow the sensor support frame to be inserted into the shell; and
- a biasing element configured to apply pressure to the piezoelectric acoustic sensing element;

a tape including an adhesive formed on an underside of the tape; and a stretchable portion attached to the shell, the stretchable portion attached to the tape and extending between the top portion of the shell and the tape, and which is configured, when the adhesive is coupled to the patient, to stretch towards the patient's skin and pull the shell and the sensor support frame toward the patient's skin so as to couple the bottom portion of the shell with the patient's skin, wherein:
- a point of attachment of the stretchable portion to the tape is between an inner adhesive perimeter and an outer adhesive perimeter of the tape,
- the point of attachment extends around an outer perimeter of the shell, defining a point of attachment perimeter, and
- the adhesive is formed over a single continuous adhesive area on the underside of the tape, the single continuous adhesive area extending between the outer adhesive perimeter and the inner adhesive perimeter, and crossing the point of attachment perimeter.

2. The acoustic sensor of claim 1, wherein the stretchable portion and the tape at least partially surround an outer perimeter of the shell as viewed from above the shell, looking down on the top portion of the shell.

3. The acoustic sensor of claim 1, wherein the tape is located approximately in a plane defined by an underside of the shell when the acoustic sensor is attached to the patient, and wherein the stretchable portion extends from the top portion of the shell to a top portion of the tape.

4. The acoustic sensor of claim 1, wherein the sensor support frame has a generally circular cross-sectional profile when viewed from a top of the sensor support frame, and wherein the shell has a generally circular cross-sectional profile when viewed from the top portion of the shell.

5. The acoustic sensor of claim 4, wherein the sensor support frame includes cutouts on either end of the sensor support frame such that the piezoelectric acoustic sensing element wraps around the sensor support frame and fits in the cutouts.

6. The acoustic sensor of claim 1, wherein the shell comprises an elastomeric material.

7. The acoustic sensor of claim 1, wherein the contact bottom portion comprises at least one of a spherical cap or a semi-spherical portion.

8. The acoustic sensor of claim 7, wherein the shell includes at least one pressure equalization pathway extending from the acoustic cavity to ambient air pressure.

* * * * *

UNITED STATES PATENT AND TRADEMARK OFFICE
CERTIFICATE OF CORRECTION

PATENT NO. : 10,828,007 B1  
APPLICATION NO. : 14/512286  
DATED : November 10, 2020  
INVENTOR(S) : Valery G. Telfort Page 1 of 1

It is certified that error appears in the above-identified patent and that said Letters Patent is hereby corrected as shown below:

In the Specification

In Column 6 at Line 28, Change "10" to --1C--.

In Column 9 at Line 63, Change "10" to --1C--.

In Column 19 at Line 39, Change "10" to --1C--.

In Column 19 at Line 40, Change "10" to --1C--.

In Column 19 at Line 42, Change "10" to --1C--.

In Column 19 at Line 64, Change "sensors" to --sensors.--.

In Column 20 at Line 53, Change "indicated" to --as indicated--.

In Column 27 at Line 35, Change "10" to --1C--.

In Column 27 at Line 36, Change "10" to --1C--.

In Column 27 at Line 59, Change "sensors" to --sensors.--.

In Column 29 at Line 1, Change "the of" to --the--.

In Column 37 at Line 49, Change "1228)" to --1228--.

In the Claims

In Column 64 at Line 29, In Claim 7, change "the contact" to --the--.

Signed and Sealed this  
Twenty-sixth Day of January, 2021

Drew Hirshfeld  
*Performing the Functions and Duties of the*  
*Under Secretary of Commerce for Intellectual Property and*  
*Director of the United States Patent and Trademark Office*